(12) United States Patent
Loset et al.

(10) Patent No.: US 9,056,920 B2
(45) Date of Patent: Jun. 16, 2015

(54) DISULPHIDE BOND-STABILIZED FUNCTIONAL SOLUBLE MHC CLASS II HETERODIMERS

(71) Applicants: Geir Age Loset, Drøbak (NO); Terje Frigstad, Oslo (NO); Inger Sandlie, Oslo (NO); Bjarne Bogen, Snaroya (NO)

(72) Inventors: Geir Age Loset, Drøbak (NO); Terje Frigstad, Oslo (NO); Inger Sandlie, Oslo (NO); Bjarne Bogen, Snaroya (NO)

(73) Assignee: Universitetet I Oslo, Oslo (NO)

( * ) Notice: Subject to any disclaimer, the term of this patent is extended or adjusted under 35 U.S.C. 154(b) by 0 days.

(21) Appl. No.: 14/331,014

(22) Filed: Jul. 14, 2014

(65) Prior Publication Data

US 2014/0349315 A1 Nov. 27, 2014

Related U.S. Application Data

(62) Division of application No. 13/579,887, filed as application No. PCT/GB2011/050325 on Feb. 18, 2011, now Pat. No. 8,828,379.

(60) Provisional application No. 61/305,728, filed on Feb. 18, 2010, provisional application No. 61/316,576, filed on Mar. 23, 2010.

(30) Foreign Application Priority Data

Feb. 18, 2010 (GB) .................................. 1002730.8

(51) Int. Cl.
| | |
|---|---|
| G01N 33/00 | (2006.01) |
| C12P 21/06 | (2006.01) |
| C07K 14/00 | (2006.01) |
| C07K 16/00 | (2006.01) |
| C07K 14/47 | (2006.01) |
| C07K 14/74 | (2006.01) |
| C07K 14/46 | (2006.01) |
| C07K 19/00 | (2006.01) |
| G01N 33/68 | (2006.01) |
| C07K 14/705 | (2006.01) |

(52) U.S. Cl.
CPC ............ *C07K 14/47* (2013.01); *C07K 14/70539* (2013.01); *C07K 2319/00* (2013.01); *C07K 14/46* (2013.01); *C07K 19/00* (2013.01); *C07K 2319/30* (2013.01); *G01N 33/6869* (2013.01)

(58) Field of Classification Search
None
See application file for complete search history.

(56) References Cited

U.S. PATENT DOCUMENTS

2008/0064859 A1 3/2008 Vandenbark et al.

FOREIGN PATENT DOCUMENTS

| WO | WO-9806749 | 2/1998 |
| WO | WO-2005044982 | 5/2005 |
| WO | WO-2006102170 | 9/2006 |
| WO | WO-2009024591 | 2/2009 |

OTHER PUBLICATIONS

Arimilli, Subhashini, et al., "Refolding and reconstitution of functionally active complexes of human leukocyte antigen DR2 and myelin basic protein peptide from recombinant α and β polypeptide chains", *J. Biol. Chem.*, 270, (1995), 971-977.
Bratkovič, Tomaž, "Progress in phage display: evolution of the technique and its applications", *Cell Mol Life Sci*, 67, (2010), 749-767.
Burrows, G G., et al., "Design engineering and production of functional single-chain T cell receptor ligands", *Protein Eng.*, 12, (1999), 771-778.
Casares, Sofia, et al., "Engineering and characterization of a murine MCH class II-immunoglobulin chimera expressing an immunodominant CD4 T viral epitope", *Protein Eng.*, 10, (1997), 1295-1301.
Constantin, Carolyn M., et al., "Major Histocompatibility Complex (MHC) Tetramer Technology: An Evaluation", *Bio. Res. Nurs.*, 4:, (2002), 115-27.
Crawford, Frances, et al., "Mimotopes for alloreactive and conventional T cells in a peptide—MHC display library", *PLos Biology*, 2, (2004), 523-533.
Crawford, Frances, et al., "Use of baculovirus MHC/peptide display libraries to characterize T-cell receptor ligands", *Immunol. Rev.*, 210, (2006), 156-170.
Halaby, D M., et al., "The immunoglobulin fold family: sequence analysis and 3D structure comparisons", *Protein Eng.*, 12, (1999), 563-571.
Jones, E Y., et al., "MHC class II proteins and disease: a structural perspective", *Nat. Rev. Immunol.*, 6, (2006), 271-282.
Kersh, Gilbert J., et al., "Structural and functional consequences of altering a peptide MHC anchor residue", *Journal of Immunology*, 166, (2001), 3345-3354.

(Continued)

*Primary Examiner* — Michael Szperka
*Assistant Examiner* — Marianne Dibrino
(74) *Attorney, Agent, or Firm* — Blakely Sokoloff Taylor & Zafman LLP

(57) ABSTRACT

The present invention relates to disulphide bond stabilized recombinant MHC class II molecules. In particular, the present invention provides a recombinant MHC class II molecule, which comprises: (i) all or part of the extracellular portion of an MHC class II α chain; (ii) all or part of the extracellular portion of an MHC class II β chain; wherein (i) and (ii) provide a functional peptide binding domain and wherein (i) and (ii) are linked by a disulphide bond between cysteine residues located in the α2 domain of said α chain and the β2 domain of said β chain, wherein said cysteine residues are not present in native MHC class II α2 and β2 domains. Methods of producing these molecules in prokaryotic systems and various uses of these molecules form further aspects.

16 Claims, 11 Drawing Sheets

(56) References Cited

OTHER PUBLICATIONS

Kozono, Haruo, et al., "Production of soluble MHC class II proteins with covalently bound single peptides", *Nature*, 147, (1994), 151-154.

Kurokawa, Manae S., et al., "Expression of MHC class I molecules together with antigenic peptides on filamentous phages", *Immunol. Lett.*, 80, (2002), 163-168.

Landais, Elise, et al., "New design of MHC class II tetramers to accommodate fundamental principles of antigen presentation", *J. Immunol.*, 183, (2009), 7949-7957.

Le Doussal, Jean-Marc, et al., "Phage display of peptide/major histocompatibility complex", *J Immunol Methods*, 241, (2000), 147-158.

Lefranc, Marie-Paule, et al., "IMGT, the Internation ImMunoGeneTics information system", *Nuc. Acids Res.*, 37 (database issue), (2009), D1006-D1012.

Leisner, Christian, et al., "One-pot, mix-and-read peptide-MHC tetramers", *PLoS One*, 3, (2008), e1678.

Løset, G Å., et al., "Functional phage display of two murine α/β T-cell receptors is strongly dependent on fusion format, mode and periplasmic folding assistance", *Protein Enc Des Sel.*, 20, (2007), 461-472.

Pack, Peter, et al., "Tetravalent miniantibodies with high avidity assembling in *Escherichia coli.*", *J. Mol. Biol.*, 246, (1995), 28-34.

Quarsten, Hanne, et al., "Staining of celiac disease-relevant T cells by peptide DQ2 multimers", *J. Immunol.*, 167, (2001), 4861-4868.

Universitetet I Oslo, et al., International Search Report and Written Opinion dated Oct. 14, 2011 for PCT/GB2011/050325.

Universitetet I Oslo, International Preliminary Report on Patentability dated Jun. 4, 2012 for PCT/GB2011/050325.

Vest Hansen, Nils J., et al., "Phage display of peptide / major histocompatibility class 1 complexes", *Eur. J. Immunol.* 31, (2001), 32-38.

Vollers, Sabrina S., et al., "Class II major histocompatibility complex tetramer staining: progress, problems, and prospects", *Immunology*, 123, (2008), 305-313.

Wallny, Hans-Joachim, et al., "Soluble mouse major histocompatibility complex class II molecules produced in Drosophila cells", *Eur. J. Immunol.*, 25, (1995), 1262-1266.

Wettstein, Daniel A., et al., "Expression of a class II major histocompatibility complex (MHC) heterodimer in a lipid-linked form with enhanced peptide/soluble MHC complex formation at low pH", *J. Exp. Med.*, 174, (1991), 219-228.

```
             |<-- signal peptide ---->|<---------------- α1 domain ------
H-2EA*02     MATIGALLLRFFFIAVLMSSQKSWA-IKEEHT-IIQAEFYLLPDKRGEFMFDFDGDEIFH  58
H-2EA_1FNG   -------------------------IKEEHT-IIQAEFYLLPDKRGEFMFDFDGDEIFH  33
H-2EA_EL     -------------------------IKEEHT-IIQAEFYLLPDKRGEFMFDFDGDEIFH  33
H-2AA*02     MPRSRALILGVLALTTMLSLCGGEDDIEADHVGSYGITVYQSPGDIGQYTFEFDGDELFY  60
                                      *: :*.     .* *.. *:: *;*****:*:

---------------------------------------------------->|<-------
H-2EA*02     VDIEKSETIWRLEEFAKFASFEAQGALANIAVDKANLDVMKERSNNTPDANVAPEVTVLS 118
H-2EA_1FNG   VDIEKSETIWRLEEFAKFASFEAQGALANIAVDKANLDVMKERSNNTPDANVAPEVTVLS  93
H-2EA_EL     VDIEKSETIWRLEEFAKFASFEAQGALANIAVDKANLDVMKERSNNTPDANVAPEVTVLS  93
H-2AA*02     VDLDKKETVWMLPEFAQLRRFEPQGGLQNIATGKHNLEILTKRSNSTPATNEAPQATVFP 120
             **:;*.**;*  *  ***::   **.**.* ***..* **:::.:***.** :* **::**:.

--------------- α2 domain ------------------------>|<-------
H-2EA*02     RSPVNLGEPNILICFIDKFSPPVVNVTWFRNGRPVTEGVSETVFLPRDDHLFRKFHYLTF 178
H-2EA_1FNG   RSPVNLGEPNILICFIDKFSPPVVNVTWLRNGRPVTEGVSETVFLPRDDHLFRKFHYLTF 153
H-2EA_EL     RSPVNLGEPNILICFIDKFSPPVVNVTWLRNGRPVTEGVSETVFLPRDDHLFRKFHYLTF 153
H-2AA*02     KSPVLLGQPNTLICFVDNIFPPVINITWLRNSKSVTDGVYETSFFVNRDYSFHKLSYLTF 180
             :*** **:** ****:*:: ***:*:**;**.:.**:** ** *:   *: *:*: ****

------------------------>|<- spacer ->|<----- TM ----------
H-2EA*02     LPSTDDFYDCEVDHWGLEEPLRKHWEFEEKTLLPETTENVVCALGLFVGLVGIVVGIILI 238
H-2EA_1FNG   LPSTDDFYDCEVDHWGLEEPLRKHWEFEE------------------------------ 182
H-2EA_EL     LPSTDDFYDCEVDHWGLEEPLRKTWE--------------------------------- 179
H-2AA*02     IPSDDDIYDCKVEHWGLEEPVLKHWEPEIPAPMSELTETVVCALGLSVGLVGIVVGTIFI 240
             :** **;***.*;:******: * **

|<--- cytoplasmic
H-2EA*02     MKGIKKRNVVERRQGAL 255
H-2EA_1FNG   -----------------
H-2EA_EL     -----------------
H-2AA*02     IQGLRSGG-TSRHPGPL 256
```

B.

```
             |<-- signal peptide ---->|<--------------- β1 domain -------
H-2EB1*01    MVWLPRVPCVAAVILLLTVLSPPVALVRDSRPWFLEYCKSECHFYNGTQRVRLLERYFYN  60
H-2EB_1FNG   ----------------------------SRPWFLEYCKSECHFYNGTQRVRLLVRYFYN  31
H-2EB_EL     ---------------------------VRDTRPRFLEYVTSECHFYNGTQHVRFLERFIYN  34
H-2AB*02     MALQIPSLLLLAAVVVLTVLSSPGTEGGNSERHFVHQFQPFCYFTNGTQRIRLVIRYIYN  60
                                          :.  *:.   . *:* ****::*:: *::**

--------------------------------------------------------
H-2EB1*01    LEENLRFDSDVGEFRAVTELGRPDAENWNSQPEFLEQKRAEVDTVCRHNYEISDKFLVRR 120
H-2EB_1FNG   LEENLRFDSDVGEFRAVTELGRPDAENWNSQPEFLEQKRAEVDTVCRHNYEIFDNFLVER  91
H-2EB_EL     REENLRFDSDVGEYRAVTELGRPDAENWNSQPEILEDARASVDTYCRHNYEISDKFLVRR  94
H-2AB*02     REEYVRFDSDVGEYRAVTELGRPDAEYWNKQ--YLERTRAELDTVCRHNYEKTETPTSLR 118
              **  :********:*********** **.*    ** **:.** ****** :.   *

->|<---------------- β2 domain ---------------------------
H-2EB1*01    RVE-PTVTVYPTKTQPLEHHNLLVCSVSDFYPGNIEVRWFRNGKEEKTGIVSTGLVRNGD 179
H-2EB_1FNG   RVE-PTVTVYPTKTQPLEHHNLLVCSVSDFYPGNIEVRWFRNGKEEKTGIVSTGLVRNGD 150
H-2EB_EL     RVE-PTVTVYPTKTQPLEHHNLLVCSVSDFYPGNIEVRWFRNGKEEETGIVSTGLVRNGD 153
H-2AB*02     RLEQPSVVISLSRTEALNHHNTLVCSVTDFYPAKIKVRWFRNGQEETVGVSSTQLIRNGD 178
             *:* *:*.:  ::*::.:*** ***********.::*;******:***:** *:;****

----------------------------------->|< spacer>|<----- TM ---
H-2EB1*01    WTFQTLVMLETVPQSGEVYTCQVEHPSLTDPVTVEWKAQSTSAQNKMLSGVGGFVLGLLF 239
H-2EB_1FNG   WTFQTLVMLETVPQSGEVYTCQVEHPSLTDPVTVEW------------------------ 186
H-2EB_EL     WTFQTLVMLETVPQSGEVYTCQVEHPSLTDPVTVEWKAQSTSAQNK-------------- 199
H-2AB*02     WTFQVLVMLEMTPRRGEVYTCHVEHPSLKSPITVEWRAQSESARSKMLSGIGGCVLGVIF 238
             ****.***** .*: ******;****** ..;*:****

------->|<--- cytoplasmic
H-2EB1*01    LGAGLFIYFRNQKGQSGLQPTGLLS 264
H-2EB_1FNG   -------------------------
H-2EB_EL     -------------------------
H-2AB*02     LGLGLFIRHRSQKGPRGPPPAGLLQ 263
```

```
H-2AA    ------MPRSRALILGVLALTTMLSLCGGEDDIEADHVGSYGITVYQSPGDIGQYTFEFD  54
HLA-DQA  ------MILNKALMLGALALTTVMSPCGGED-IVADHVASYGVNLYQSYGPSGQYTHEFD  53
HLA-DPA  MRPEDRMFHIRAVILRALSLAFLLSLR-GAGAIKADHVSTY-AAFVQTHRPTGEFMFEFD  58
H-2EA    ------MATIGALLLRFFFIAVLMSSQ-KSWAIKEEHTIIQ-AEFYLLPDKRGEFMFDFD  52
HLA-DRA  ------MAISGVPVLGFFIIAVLMSAQ-ESWAIKEEHVIIQ-AEFYLNPDQSGEFMFDFD  52
               *    .:*   :  :: :*     *  :*.       *::  .:**

H-2AA    GDELFYVDLDKKETVWMLPEFAQLRRFEPQGGLQNIATGKHNLEILTKRSNSTPATNEAP  114
HLA-DQA  GDEQFYVDLGRKETVWCLPVLRQFR-FDPQFALTNIAVLKHNLNSLIKRSNSTAATNEVP  112
HLA-DPA  EDEMFYVDLDKKETVWHLEEFGQAFSFEAQGGLANIAILNNNLNTLIQRSNHTQATNDPP  118
H-2EA    GDEIFHVDIEKSETIWRLEEFAKFASFEAQGALANIAVDKANLDVMKERSNNTPDANVAP  112
HLA-DRA  GDEIFHVDMAKKETVWRLEEFGRFASFEAQGALANIAVDKANLEIMTKRSNYTPITNVPP  112
           ** *:** :.**:*   *  : :   *:. * ***  : **: ; :*** * :*   *

H-2AA    QATVFPKSPVLLGQPNTLICFVDNIFPPVINITWLRNSKSVTDGVYETSFFVNRDYSFHK  174
HLA-DQA  EVTVFSKSPVTLGQPNILICLVDNIFPPVVNITWLSNGHSVTEGVSETSFLSKSDHSFFK  172
HLA-DPA  EVTVFPKEPVELGQPNTLICHIDKFFPPVLNVTWLCNGELVTEGVAESLFLPRTDYSFHK  178
H-2EA    EVTVLSRSPVNLGEPNILICFIDKFSPPVVNVTWFRNGRPVTEGVSETVFLPRDDHLFRK  172
HLA-DRA  EVTVLTNSPVELREPNVLICFIDKFTPPVVNVTWLRNGKPVTTGVSETVFLPREDHLFRK  172
          :.**:...** *:** *** :*:: ***:*:**: *,. ** ** *: *: . *: * *

H-2AA    LSYLTFIPSDDDIYDCKVEHWGLEEPVLKHWEPEIPAPMSELTETVVCALGLSVGLVGIV  234
HLA-DQA  ISYLTLLPSAEESYDCKVEHWGLDKPLLKHWEPEIPAPMSELTETVVLCALGLSVGLVGIV 232
HLA-DPA  FHYLTFVPSAEDFYDCRVEHWGLDQPLLKHWEAQEPIQMPETTETVLCALGLVLGLVGII  238
H-2EA    FHYLTFLPSTDDFYDCEVDHWGLEEPLRKHWEFEEKILLPETTENVVCALGLFVGLVGIV  232
HLA-DRA  FHYLPFLPSTEDVYDCRVEHWGLDEPLLKHWEFDAPSPLPETTENVVCALGLTVGLVGII  232
         : **.:** :: ***.*:****:*:  ****  :    :.* **.*:***** :*****:

H-2AA    VGTIFIIQGLR-SGGTSRHPGPL  256
HLA-DQA  VGTVFIIRGLR-SVGASRHQGPL  254
HLA-DPA  VGTVLIIKSLR-SGHDPRAQGTL  260
H-2EA    VGIILIMKGIKKRNVVERRQGAL  255
HLA-DRA  IGTIFIIKGVRKSNAAERR-GPL  254
         :*  ::*::. ::         *  *.*
```

B.

```
H-2AB    ----MALQIP-SLLLLAAVVVLTVLSSPGTEGGNSERHFVHQFQPFCYFTNGTQRIRLVI  55
HLA-DQB  MSWKKALRIPGGLRAATVTLMLSMLSTPVAEGRDSPEDFVYQFKGMCYFTNGTERVRLVS  60
HLA-DPB  ---MMVLQVSAAPRTVALTALLMVLLTSVVQGRATPENYLFQGRQECYAFNGTQ--RFLE  55
H-2EB    -----MVWLPRVPCVAAVILLLTVLSPPVALVRDSRPWFLEYCKSECHFYNGTQRVRLLE  55
HLA_DRB  ---MVCLRLPGGSCMAVLTVTLMVLSSPLALAGDTRPRFLEYSTSECHFFNGTERVRFLE  57
             : :.        . * :*  .. . :  :: *: ***: *::

H-2AB    RYIYNREEYVRFDSDVGEYRAVTELGRPDAEYWN--KQYLERTRAELDTVCRHNYEKTET  113
HLA-DQB  RSIYNREEIVRFDSDVGEFRAVTLLGLPAAEYWNSQKDILERKRAAVDRVCRHNYQ-LEL  119
HLA-DPB  RYIYNREEFARFDSDVGEFRATELGRPAAEYWNSQKDILEEKRAVPDRMCRHNYE-LGG  114
H-2EB    RYFYNLEENLRFDSDVGEFRAVTELGRPDAENWNSQPEFLEQKRAEVDTYCRHNYE-ISD  114
HLA_DRB  RYFHNQEENVRFDSDVGEYRAVTELGRPDAEYWNSQKDLLEQRRAAVDTYCRHNYG-VGE  116
         * ::*  ** ******:****  ** ** **       : **. **    *  ****

H-2AB    PTSLRRLEQPSVVISLSRTEALNHHNTLVCSVTDFYPAKIKVRWFRNGQEETVGVSSTQL  173
HLA-DQB  RTTLQRRVEPTVTISPSRTEALNHHNLLVCSVTDFYPAQIKVRWFRNDQEETAGVVSTPL  179
HLA-DPB  PMTLQRRVQPRVNVSPSKKGPLQHHNLLVCHVTDFYPGSIQVRWFLNGQEETAGVVSTNL  174
H-2EB    KFLVRRRVEPTVTVYPTKTQPLEHHNLLVCSVSDFYPGNIEVRWFRNGKEEKTGIVSTGL  174
HLA_DRB  SFTVQRRVHPKVTVYPSKTQPLQHHNLLVCSVSGFYPGSIEVRWFRNGQEEKTGVVSTGL  176
         :::*  .* * :   ::..*:*** *** *: *** .:**** * :**:.:: ** *

H-2AB    IRNGDWTFQVLVMLEMTPRRGEVYTCHVEHPSLKSPITVEWRAQSESARSKMLSGIGGCV  233
HLA-DQB  IRNGDWTFQILVMLEMTPQRGDVYTCHVEHPSLQSPITVEWRAQSEQSAQSKMLSGIGGFV  239
HLA-DPB  IRNGDWTFQILVMLEMTPQQGDVYTCQVEHTSLDSPVTVEWKAQSDSARSKTLTGAGGFV  234
H-2EB    VRNGDWTFQTLVMLETVPQSGEVYTCQVEHPSLTDPVTVEWKAQSTSAQNKMLSGVGGFV  234
HLA_DRB  IHNGDWTFQTLVMLETVPRSGEVYTCQVEHPSVTSPLTVEWRARSESAQSKMLSGVGGFV  236
         ::******* ***** .*: *:****:*** *:  .*****:* *: ** *:*  ** *

H-2AB    LGVIFLGLGLFIRHRSQKGPRGPPPAGLLQ  263
HLA-DQB  LGLIFLGLGLIIHHRSQKG--------LLH  261
HLA-DPB  LGLIICGVGIFMHRRSKKVQRGSA------ 258
H-2EB    LGLLFLGAGLFIYFRNQKGQSGLQPTGLLS  264
HLA_DRB  LGLLFLGAGLFIYFRNQKGHSGLQPRGF-- 264
         **::: * *:::   *.:*
```

Figure 8.
A.
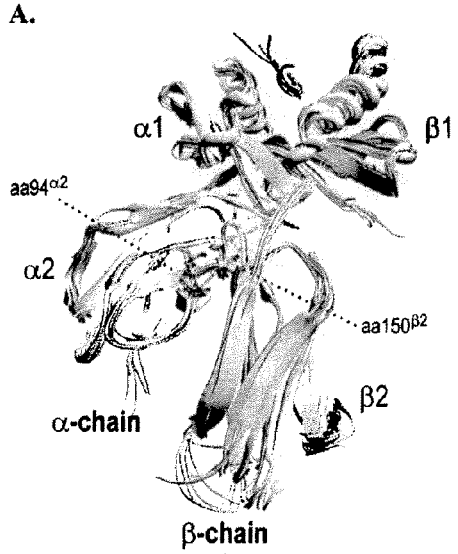
B.
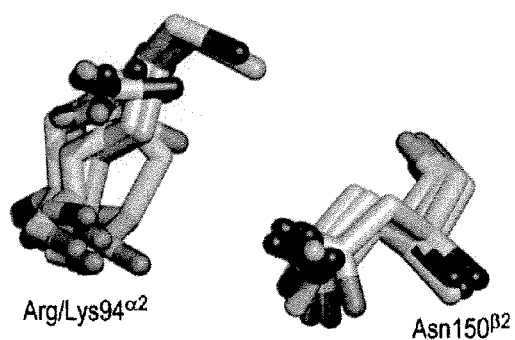

SEQUENCE LISTING

```
<160> NUMBER OF SEQ ID NOS: 66

<210> SEQ ID NO 1
<211> LENGTH: 255
<212> TYPE: PRT
<213> ORGANISM: Mus musculus

<400> SEQUENCE: 1

Met Ala Thr Ile Gly Ala Leu Leu Leu Arg Phe Phe Phe Ile Ala Val
1               5                   10                  15

Leu Met Ser Ser Gln Lys Ser Trp Ala Ile Lys Glu Glu His Thr Ile
            20                  25                  30

Ile Gln Ala Glu Phe Tyr Leu Leu Pro Asp Lys Arg Gly Glu Phe Met
        35                  40                  45

Phe Asp Phe Asp Gly Asp Glu Ile Phe His Val Asp Ile Glu Lys Ser
    50                  55                  60

Glu Thr Ile Trp Arg Leu Glu Glu Phe Ala Lys Phe Ala Ser Phe Glu
65                  70                  75                  80
```

```
Ala Gln Gly Ala Leu Ala Asn Ile Ala Val Asp Lys Ala Asn Leu Asp
                85                  90                  95

Val Met Lys Glu Arg Ser Asn Asn Thr Pro Asp Ala Asn Val Ala Pro
            100                 105                 110

Glu Val Thr Val Leu Ser Arg Ser Pro Val Asn Leu Gly Glu Pro Asn
        115                 120                 125

Ile Leu Ile Cys Phe Ile Asp Lys Phe Ser Pro Val Val Asn Val
    130                 135                 140

Thr Trp Phe Arg Asn Gly Arg Pro Val Thr Glu Gly Val Ser Glu Thr
145                 150                 155                 160

Val Phe Leu Pro Arg Asp Asp His Leu Phe Arg Lys Phe His Tyr Leu
                165                 170                 175

Thr Phe Leu Pro Ser Thr Asp Asp Phe Tyr Asp Cys Glu Val Asp His
            180                 185                 190

Trp Gly Leu Glu Glu Pro Leu Arg Lys His Trp Glu Phe Glu Glu Lys
        195                 200                 205

Thr Leu Leu Pro Glu Thr Thr Glu Asn Val Val Cys Ala Leu Gly Leu
    210                 215                 220

Phe Val Gly Leu Val Gly Ile Val Val Gly Ile Ile Leu Ile Met Lys
225                 230                 235                 240

Gly Ile Lys Lys Arg Asn Val Val Glu Arg Arg Gln Gly Ala Leu
                245                 250                 255

<210> SEQ ID NO 2
<211> LENGTH: 264
<212> TYPE: PRT
<213> ORGANISM: Mus musculus

<400> SEQUENCE: 2

Met Val Trp Leu Pro Arg Val Pro Cys Val Ala Ala Val Ile Leu Leu
1               5                   10                  15

Leu Thr Val Leu Ser Pro Pro Val Ala Leu Val Arg Asp Ser Arg Pro
            20                  25                  30

Trp Phe Leu Glu Tyr Cys Lys Ser Glu Cys His Phe Tyr Asn Gly Thr
        35                  40                  45

Gln Arg Val Arg Leu Leu Glu Arg Tyr Phe Tyr Asn Leu Glu Glu Asn
    50                  55                  60

Leu Arg Phe Asp Ser Asp Val Gly Glu Phe Arg Ala Val Thr Glu Leu
65                  70                  75                  80

Gly Arg Pro Asp Ala Glu Asn Trp Asn Ser Gln Pro Glu Phe Leu Glu
                85                  90                  95

Gln Lys Arg Ala Glu Val Asp Thr Val Cys Arg His Asn Tyr Glu Ile
            100                 105                 110

Ser Asp Lys Phe Leu Val Arg Arg Val Glu Pro Thr Val Thr Val
    115                 120                 125

Tyr Pro Thr Lys Thr Gln Pro Leu Glu His His Asn Leu Leu Val Cys
130                 135                 140

Ser Val Ser Asp Phe Tyr Pro Gly Asn Ile Glu Val Arg Trp Phe Arg
145                 150                 155                 160

Asn Gly Lys Glu Glu Lys Thr Gly Ile Val Ser Thr Gly Leu Val Arg
                165                 170                 175

Asn Gly Asp Trp Thr Phe Gln Thr Leu Val Met Leu Glu Thr Val Pro
            180                 185                 190

Gln Ser Gly Glu Val Tyr Thr Cys Gln Val Glu His Pro Ser Leu Thr
```

```
            195                 200                 205

Asp Pro Val Thr Val Glu Trp Lys Ala Gln Ser Thr Ser Ala Gln Asn
    210                 215                 220

Lys Met Leu Ser Gly Val Gly Phe Val Leu Gly Leu Leu Phe Leu
225                 230                 235                 240

Gly Ala Gly Leu Phe Ile Tyr Phe Arg Asn Gln Lys Gly Gln Ser Gly
                245                 250                 255

Leu Gln Pro Thr Gly Leu Leu Ser
            260

<210> SEQ ID NO 3
<211> LENGTH: 230
<212> TYPE: PRT
<213> ORGANISM: Mus musculus

<400> SEQUENCE: 3

Ile Lys Glu Glu His Thr Ile Ile Gln Ala Glu Phe Tyr Leu Leu Pro
1               5                   10                  15

Asp Lys Arg Gly Glu Phe Met Phe Asp Phe Asp Gly Asp Glu Ile Phe
                20                  25                  30

His Val Asp Ile Glu Lys Ser Glu Thr Ile Trp Arg Leu Glu Glu Phe
            35                  40                  45

Ala Lys Phe Ala Ser Phe Glu Ala Gln Gly Ala Leu Ala Asn Ile Ala
        50                  55                  60

Val Asp Lys Ala Asn Leu Asp Val Met Lys Glu Arg Ser Asn Asn Thr
65                  70                  75                  80

Pro Asp Ala Asn Val Ala Pro Glu Val Thr Val Leu Ser Arg Ser Pro
                85                  90                  95

Val Asn Leu Gly Glu Pro Asn Ile Leu Ile Cys Phe Ile Asp Lys Phe
            100                 105                 110

Ser Pro Pro Val Val Asn Val Thr Trp Phe Arg Asn Gly Arg Pro Val
        115                 120                 125

Thr Glu Gly Val Ser Glu Thr Val Phe Leu Pro Arg Asp Asp His Leu
130                 135                 140

Phe Arg Lys Phe His Tyr Leu Thr Phe Leu Pro Ser Thr Asp Asp Phe
145                 150                 155                 160

Tyr Asp Cys Glu Val Asp His Trp Gly Leu Glu Glu Pro Leu Arg Lys
                165                 170                 175

His Trp Glu Phe Glu Glu Lys Thr Leu Leu Pro Glu Thr Thr Glu Asn
            180                 185                 190

Val Val Cys Ala Leu Gly Leu Phe Val Gly Leu Val Gly Ile Val Val
        195                 200                 205

Gly Ile Ile Leu Ile Met Lys Gly Ile Lys Lys Arg Asn Val Val Glu
    210                 215                 220

Arg Arg Gln Gly Ala Leu
225                 230

<210> SEQ ID NO 4
<211> LENGTH: 238
<212> TYPE: PRT
<213> ORGANISM: Mus musculus

<400> SEQUENCE: 4

Val Arg Asp Ser Arg Pro Trp Phe Leu Glu Tyr Cys Lys Ser Glu Cys
1               5                   10                  15

His Phe Tyr Asn Gly Thr Gln Arg Val Arg Leu Leu Glu Arg Tyr Phe
```

-continued

```
                20                  25                  30
Tyr Asn Leu Glu Glu Asn Leu Arg Phe Asp Ser Asp Val Gly Glu Phe
         35                  40                  45
Arg Ala Val Thr Glu Leu Gly Arg Pro Asp Ala Glu Asn Trp Asn Ser
 50                  55                  60
Gln Pro Glu Phe Leu Glu Gln Lys Arg Ala Glu Val Asp Thr Val Cys
 65                  70                  75                  80
Arg His Asn Tyr Glu Ile Ser Asp Lys Phe Leu Val Arg Arg Arg Val
                 85                  90                  95
Glu Pro Thr Val Thr Val Tyr Pro Thr Lys Thr Gln Pro Leu Glu His
                100                 105                 110
His Asn Leu Leu Val Cys Ser Val Ser Asp Phe Tyr Pro Gly Asn Ile
                115                 120                 125
Glu Val Arg Trp Phe Arg Asn Gly Lys Glu Lys Thr Gly Ile Val
                130                 135                 140
Ser Thr Gly Leu Val Arg Asn Gly Asp Trp Thr Phe Gln Thr Leu Val
145                 150                 155                 160
Met Leu Glu Thr Val Pro Gln Ser Gly Glu Val Tyr Thr Cys Gln Val
                165                 170                 175
Glu His Pro Ser Leu Thr Asp Pro Val Thr Val Glu Trp Lys Ala Gln
                180                 185                 190
Ser Thr Ser Ala Gln Asn Lys Met Leu Ser Gly Val Gly Gly Phe Val
                195                 200                 205
Leu Gly Leu Leu Phe Leu Gly Ala Gly Leu Phe Ile Tyr Phe Arg Asn
                210                 215                 220
Gln Lys Gly Gln Ser Gly Leu Gln Pro Thr Gly Leu Leu Ser
225                 230                 235

<210> SEQ ID NO 5
<211> LENGTH: 9
<212> TYPE: PRT
<213> ORGANISM: Homo sapiens

<400> SEQUENCE: 5

Trp Lys Ile Asp Gly Ser Glu Arg Gln
1               5

<210> SEQ ID NO 6
<211> LENGTH: 21
<212> TYPE: PRT
<213> ORGANISM: Homo sapiens

<400> SEQUENCE: 6

Phe Asn Asn Phe Thr Val Ser Phe Trp Leu Arg Val Pro Lys Val Ser
1               5                   10                  15

Ala Ser His Leu Glu
            20

<210> SEQ ID NO 7
<211> LENGTH: 11
<212> TYPE: PRT
<213> ORGANISM: Haemophilus influenzae

<400> SEQUENCE: 7

Ser Phe Glu Arg Phe Glu Ile Phe Pro Lys Glu
1               5                   10

<210> SEQ ID NO 8
```

```
<211> LENGTH: 15
<212> TYPE: PRT
<213> ORGANISM: Artificial Sequence
<220> FEATURE:
<223> OTHER INFORMATION: Recombinant

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 6
<212> TYPE: PRT
<213> ORGANISM: Artificial Sequence
<220> FEATURE:
<223> OTHER INFORMATION: Recombinant

<400> SEQUENCE: 9

Gly Ser Gly Ser Gly Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Recombinant

<400> SEQUENCE: 10

Gly Gly Ser Gly Ser Gly Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Recombinant

<400> SEQUENCE: 11

Ser Gly Ser Gly Ser Gly Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Recombinant

<400> SEQUENCE: 12

Ser Gly Gly Ser Gly Ser Gly Ser
1               5

<210> SEQ ID NO 13
<211> LENGTH: 11
<212> TYPE: PRT
<213> ORGANISM: Artificial Sequence
<220> FEATURE:
<223> OTHER INFORMATION: Recombinant

<400> SEQUENCE: 13

Ser Phe Glu Arg Phe Glu Ile Phe Pro Lys Glu
1               5                   10

<210> SEQ ID NO 14
<211> LENGTH: 9
```

```
<212> TYPE: PRT
<213> ORGANISM: Artificial Sequence
<220> FEATURE:
<223> OTHER INFORMATION: Recombinant

<400> SEQUENCE: 14

Trp Lys Ile Asp Gly Ser Glu Arg Gln
1               5

<210> SEQ ID NO 15
<211> LENGTH: 12
<212> TYPE: PRT
<213> ORGANISM: Artificial Sequence
<220> FEATURE:
<223> OTHER INFORMATION: Recombinant

<400> SEQUENCE: 15

Gln Leu Gln Pro Phe Pro Gln Pro Glu Leu Pro Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Recombinant

<400> SEQUENCE: 16

Pro Gln Pro Glu Leu Pro Tyr Pro Gln Pro Glu
1               5                   10

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
tataccatgg ccatcaaaga ggaacacacc atcatccagg                            40

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
tataactagt cattactccc agtgcttccg cagag                                 35

<210> SEQ ID NO 19
<211> LENGTH: 35
<212> TYPE: DNA
<213> ORGANISM: Artificial Sequence
<220> FEATURE:
<223> OTHER INFORMATION: Primer

<400> SEQUENCE: 19
tataacgcgt cagagacacc agaccacggt ttttg                                 35

<210> SEQ ID NO 20
<211> LENGTH: 42
<212> TYPE: DNA
<213> ORGANISM: Artificial Sequence
<220> FEATURE:
<223> OTHER INFORMATION: Primer
```

<400> SEQUENCE: 20
tataggccgc agcggcccct ttccactcga ccgtgacagg gt                42

<210> SEQ ID NO 21
<211> LENGTH: 75
<212> TYPE: DNA
<213> ORGANISM: Artificial Sequence
<220> FEATURE:
<223> OTHER INFORMATION: Sequence for recombinant linker

<400> SEQUENCE: 21
aaaggaagga ggtggtggct ccggtggagg gggaagtgga ggtggagggt ctgtcagaga    60
caccagacca cggtt                                                    75

<210> SEQ ID NO 22
<211> LENGTH: 65
<212> TYPE: DNA
<213> ORGANISM: Artificial Sequence
<220> FEATURE:
<223> OTHER INFORMATION: Sequence for recombinant linker

<400> SEQUENCE: 22
ggagccacca cctccttcct ttgggaagat ctcgaaccttt cgaatgata cgcgtgccat    60 cgccg                                                               65

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
tggacacgta ctgtagacac aactatgaga t                                  31

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24
atctcatagt tgtgtctaca gtacgtgtcc a                                  31

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
gactgtactc tcctgtagcc ctgtgaacc                                     29

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
ggttcacagg gctacaggag agtacagtc                                    29

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
cctggtccga tgtggagact ggaccttc                                     28

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
gaaggtccag tctccacatc ggaccagg                                     28

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
actctccaga tgccctgtga ac                                           22

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
gttcacaggg catctggaga gt                                           22

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
gtctgctctg tgtgtgactt ctac                                         24

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
gtagaagtca cacacagagc agac                                         24

<210> SEQ ID NO 33
<211> LENGTH: 22
<212> TYPE: DNA
<213> ORGANISM: Artificial Sequence

```
<220> FEATURE:
<223> OTHER INFORMATION: Primer

<400> SEQUENCE: 33
cagaagctgt gtgaacctgg ga                                              22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
tcccaggttc acacagcttc tg                                              22

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
cctggtctgc tgtgtgagtg ac                                              22

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
gtcactcaca cagcagacca gg                                              22

<210> SEQ ID NO 37
<211> LENGTH: 35
<212> TYPE: DNA
<213> ORGANISM: Artificial Sequence
<220> FEATURE:
<223> OTHER INFORMATION: Primer Sense

<400> SEQUENCE: 37
gaccgtgttt cccaagtgcc ctgtggagct gggcc                                35

<210> SEQ ID NO 38
<211> LENGTH: 35
<212> TYPE: DNA
<213> ORGANISM: Artificial Sequence
<220> FEATURE:
<223> OTHER INFORMATION: Primer Antisense

<400> SEQUENCE: 38
ggcccagctc cacagggcac ttgggaaaca cggtc                                35

<210> SEQ ID NO 39
<211> LENGTH: 29
<212> TYPE: DNA
<213> ORGANISM: Artificial Sequence
<220> FEATURE:
<223> OTHER INFORMATION: Primer Sense

<400> SEQUENCE: 39
ctgtgctcac gaactgccct gtggaactg                                       29
```

<210> SEQ ID NO 40
<211> LENGTH: 29
<212> TYPE: DNA
<213> ORGANISM: Artificial Sequence
<220> FEATURE:
<223> OTHER INFORMATION: Primer Antisense

<400> SEQUENCE: 40
cagttccaca gggcagttcg tgagcacag                              29

<210> SEQ ID NO 41
<211> LENGTH: 37
<212> TYPE: DNA
<213> ORGANISM: Artificial Sequence
<220> FEATURE:
<223> OTHER INFORMATION: Primer Sense

<400> SEQUENCE: 41
tgaggtcaca gtgttttcca agtgccccgt gacactg                     37

<210> SEQ ID NO 42
<211> LENGTH: 37
<212> TYPE: DNA
<213> ORGANISM: Artificial Sequence
<220> FEATURE:
<223> OTHER INFORMATION: Primer Antisense

<400> SEQUENCE: 42
cagtgtcacg gggcacttgg aaaacactgt gacctca                     37

<210> SEQ ID NO 43
<211> LENGTH: 37
<212> TYPE: DNA
<213> ORGANISM: Artificial Sequence
<220> FEATURE:
<223> OTHER INFORMATION: Primer Sense

<400> SEQUENCE: 43
tgcttgtctg ccacgtgtgc gatttctacc caggcag                     37

<210> SEQ ID NO 44
<211> LENGTH: 37
<212> TYPE: DNA
<213> ORGANISM: Artificial Sequence
<220> FEATURE:
<223> OTHER INFORMATION: Primer Antisense

<400> SEQUENCE: 44
ctgcctgggt agaaatcgca cacgtggcag acaagca                     37

<210> SEQ ID NO 45
<211> LENGTH: 37
<212> TYPE: DNA
<213> ORGANISM: Artificial Sequence
<220> FEATURE:
<223> OTHER INFORMATION: Primer Sense

<400> SEQUENCE: 45
tcctggtctg ttctgtgtgc ggtttctatc caggcag                     37

<210> SEQ ID NO 46
<211> LENGTH: 37
<212> TYPE: DNA
<213> ORGANISM: Artificial Sequence
<220> FEATURE:
<223> OTHER INFORMATION: Primer Antisense

```
<400> SEQUENCE: 46
ctgcctggat agaaaccgca cacagaacag accagga                                    37

<210> SEQ ID NO 47
<211> LENGTH: 39
<212> TYPE: DNA
<213> ORGANISM: Artificial Sequence
<220> FEATURE:
<223> OTHER INFORMATION: Primer Sense

<400> SEQUENCE: 47
ctgctggtct gctcagtgtg cgatttctat ccagcccag                                  39

<210> SEQ ID NO 48
<211> LENGTH: 39
<212> TYPE: DNA
<213> ORGANISM: Artificial Sequence
<220> FEATURE:
<223> OTHER INFORMATION: Primer Antisense

<400> SEQUENCE: 48
ctgggctgga tagaaatcgc acactgagca gaccagcag                                  39

<210> SEQ ID NO 49
<211> LENGTH: 255
<212> TYPE: PRT
<213> ORGANISM: Mus musculus

<400> SEQUENCE: 49

Met Ala Thr Ile Gly Ala Leu Leu Leu Arg Phe Phe Phe Ile Ala Val
1               5                   10                  15

Leu Met Ser Ser Gln Lys Ser Trp Ala Ile Lys Glu Glu His Thr Ile
            20                  25                  30

Ile Gln Ala Glu Phe Tyr Leu Leu Pro Asp Lys Arg Gly Glu Phe Met
        35                  40                  45

Phe Asp Phe Asp Gly Asp Glu Ile Phe His Val Asp Ile Glu Lys Ser
    50                  55                  60

Glu Thr Ile Trp Arg Leu Glu Glu Phe Ala Lys Phe Ala Ser Phe Glu
65                  70                  75                  80

Ala Gln Gly Ala Leu Ala Asn Ile Ala Val Asp Lys Ala Asn Leu Asp
                85                  90                  95

Val Met Lys Glu Arg Ser Asn Asn Thr Pro Asp Ala Asn Val Ala Pro
            100                 105                 110

Glu Val Thr Val Leu Ser Arg Ser Pro Val Asn Leu Gly Glu Pro Asn
        115                 120                 125

Ile Leu Ile Cys Phe Ile Asp Lys Phe Ser Pro Pro Val Val Asn Val
    130                 135                 140

Thr Trp Phe Arg Asn Gly Arg Pro Val Thr Glu Gly Val Ser Glu Thr
145                 150                 155                 160

Val Phe Leu Pro Arg Asp Asp His Leu Phe Arg Lys Phe His Tyr Leu
                165                 170                 175

Thr Phe Leu Pro Ser Thr Asp Asp Phe Tyr Asp Cys Glu Val Asp His
            180                 185                 190

Trp Gly Leu Glu Glu Pro Leu Arg Lys His Trp Glu Phe Glu Glu Lys
        195                 200                 205

Thr Leu Leu Pro Glu Thr Thr Glu Asn Val Val Cys Ala Leu Gly Leu
    210                 215                 220
```

```
Phe Val Gly Leu Val Gly Ile Val Val Gly Ile Leu Ile Met Lys
225                 230                 235                 240

Gly Ile Lys Lys Arg Asn Val Val Glu Arg Arg Gln Gly Ala Leu
            245                 250                 255
```

<210> SEQ ID NO 50
<211> LENGTH: 182
<212> TYPE: PRT
<213> ORGANISM: Artificial Sequence
<220> FEATURE:
<223> OTHER INFORMATION: Recombinant

<400> SEQUENCE: 50

```
Ile Lys Glu Glu His Thr Ile Ile Gln Ala Glu Phe Tyr Leu Leu Pro
1               5                   10                  15

Asp Lys Arg Gly Glu Phe Met Phe Asp Phe Asp Gly Asp Glu Ile Phe
            20                  25                  30

His Val Asp Ile Glu Lys Ser Glu Thr Ile Trp Arg Leu Glu Glu Phe
        35                  40                  45

Ala Lys Phe Ala Ser Phe Glu Ala Gln Gly Ala Leu Ala Asn Ile Ala
    50                  55                  60

Val Asp Lys Ala Asn Leu Asp Val Met Lys Glu Arg Ser Asn Asn Thr
65                  70                  75                  80

Pro Asp Ala Asn Val Ala Pro Glu Val Thr Val Leu Ser Arg Ser Pro
                85                  90                  95

Val Asn Leu Gly Glu Pro Asn Ile Leu Ile Cys Phe Ile Asp Lys Phe
            100                 105                 110

Ser Pro Pro Val Val Asn Val Thr Trp Leu Arg Asn Gly Arg Pro Val
        115                 120                 125

Thr Glu Gly Val Ser Glu Thr Val Phe Leu Pro Arg Asp Asp His Leu
130                 135                 140

Phe Arg Lys Phe His Tyr Leu Thr Phe Leu Pro Ser Thr Asp Asp Phe
145                 150                 155                 160

Tyr Asp Cys Glu Val Asp His Trp Gly Leu Glu Glu Pro Leu Arg Lys
                165                 170                 175

His Trp Glu Phe Glu Glu
            180
```

<210> SEQ ID NO 51
<211> LENGTH: 179
<212> TYPE: PRT
<213> ORGANISM: Artificial Sequence
<220> FEATURE:
<223> OTHER INFORMATION: Recombinant

<400> SEQUENCE: 51

```
Ile Lys Glu Glu His Thr Ile Ile Gln Ala Glu Phe Tyr Leu Leu Pro
1               5                   10                  15

Asp Lys Arg Gly Glu Phe Met Phe Asp Phe Asp Gly Asp Glu Ile Phe
            20                  25                  30

His Val Asp Ile Glu Lys Ser Glu Thr Ile Trp Arg Leu Glu Glu Phe
        35                  40                  45

Ala Lys Phe Ala Ser Phe Glu Ala Gln Gly Ala Leu Ala Asn Ile Ala
    50                  55                  60

Val Asp Lys Ala Asn Leu Asp Val Met Lys Glu Arg Ser Asn Asn Thr
65                  70                  75                  80

Pro Asp Ala Asn Val Ala Pro Glu Val Thr Val Leu Ser Arg Ser Pro
                85                  90                  95
```

```
Val Asn Leu Gly Glu Pro Asn Ile Leu Ile Cys Phe Ile Asp Lys Phe
            100                 105                 110

Ser Pro Val Val Asn Val Thr Trp Leu Arg Asn Gly Arg Pro Val
        115                 120                 125

Thr Glu Gly Val Ser Glu Thr Val Phe Leu Pro Arg Asp Asp His Leu
130                 135                 140

Phe Arg Lys Phe His Tyr Leu Thr Phe Leu Pro Ser Thr Asp Phe
145                 150                 155                 160

Tyr Asp Cys Glu Val Asp His Trp Gly Leu Glu Glu Pro Leu Arg Lys
                165                 170                 175

Thr Trp Glu

<210> SEQ ID NO 52
<211> LENGTH: 256
<212> TYPE: PRT
<213> ORGANISM: Mus musculus

<400> SEQUENCE: 52

Met Pro Arg Ser Arg Ala Leu Ile Leu Gly Val Leu Ala Leu Thr Thr
1               5                   10                  15

Met Leu Ser Leu Cys Gly Gly Glu Asp Asp Ile Glu Ala Asp His Val
                20                  25                  30

Gly Ser Tyr Gly Ile Thr Val Tyr Gln Ser Pro Gly Asp Ile Gly Gln
            35                  40                  45

Tyr Thr Phe Glu Phe Asp Gly Asp Glu Leu Phe Tyr Val Asp Leu Asp
    50                  55                  60

Lys Lys Glu Thr Val Trp Met Leu Pro Glu Phe Ala Gln Leu Arg Arg
65                  70                  75                  80

Phe Glu Pro Gln Gly Gly Leu Gln Asn Ile Ala Thr Gly Lys His Asn
                85                  90                  95

Leu Glu Ile Leu Thr Lys Arg Ser Asn Ser Thr Pro Ala Thr Asn Glu
            100                 105                 110

Ala Pro Gln Ala Thr Val Phe Pro Lys Ser Pro Val Leu Leu Gly Gln
        115                 120                 125

Pro Asn Thr Leu Ile Cys Phe Val Asp Asn Ile Phe Pro Pro Val Ile
130                 135                 140

Asn Ile Thr Trp Leu Arg Asn Ser Lys Ser Val Thr Asp Gly Val Tyr
145                 150                 155                 160

Glu Thr Ser Phe Phe Val Asn Arg Asp Tyr Ser Phe His Lys Leu Ser
                165                 170                 175

Tyr Leu Thr Phe Ile Pro Ser Asp Asp Asp Ile Tyr Asp Cys Lys Val
            180                 185                 190

Glu His Trp Gly Leu Glu Glu Pro Val Leu Lys His Trp Glu Pro Glu
        195                 200                 205

Ile Pro Ala Pro Met Ser Glu Leu Thr Glu Thr Val Val Cys Ala Leu
210                 215                 220

Gly Leu Ser Val Gly Leu Val Gly Ile Val Val Gly Thr Ile Phe Ile
225                 230                 235                 240

Ile Gln Gly Leu Arg Ser Gly Gly Thr Ser Arg His Pro Gly Pro Leu
                245                 250                 255

<210> SEQ ID NO 53
<211> LENGTH: 264
<212> TYPE: PRT
<213> ORGANISM: Mus musculus
```

<400> SEQUENCE: 53

Met Val Trp Leu Pro Arg Val Pro Cys Val Ala Val Ile Leu Leu
1               5                   10                  15

Leu Thr Val Leu Ser Pro Val Ala Leu Val Arg Asp Ser Arg Pro
            20                  25                  30

Trp Phe Leu Glu Tyr Cys Lys Ser Glu Cys His Phe Tyr Asn Gly Thr
        35                  40                  45

Gln Arg Val Arg Leu Leu Glu Arg Tyr Phe Tyr Asn Leu Glu Glu Asn
    50                  55                  60

Leu Arg Phe Asp Ser Asp Val Gly Glu Phe Arg Ala Val Thr Glu Leu
65                  70                  75                  80

Gly Arg Pro Asp Ala Glu Asn Trp Asn Ser Gln Pro Glu Phe Leu Glu
                85                  90                  95

Gln Lys Arg Ala Glu Val Asp Thr Val Cys Arg His Asn Tyr Glu Ile
            100                 105                 110

Ser Asp Lys Phe Leu Val Arg Arg Val Glu Pro Thr Val Thr Val
            115                 120                 125

Tyr Pro Thr Lys Thr Gln Pro Leu Glu His His Asn Leu Leu Val Cys
130                 135                 140

Ser Val Ser Asp Phe Tyr Pro Gly Asn Ile Glu Val Arg Trp Phe Arg
145                 150                 155                 160

Asn Gly Lys Glu Glu Lys Thr Gly Ile Val Ser Thr Gly Leu Val Arg
                165                 170                 175

Asn Gly Asp Trp Thr Phe Gln Thr Leu Val Met Leu Glu Thr Val Pro
            180                 185                 190

Gln Ser Gly Glu Val Tyr Thr Cys Gln Val Glu His Pro Ser Leu Thr
        195                 200                 205

Asp Pro Val Thr Val Glu Trp Lys Ala Gln Ser Thr Ser Ala Gln Asn
210                 215                 220

Lys Met Leu Ser Gly Val Gly Gly Phe Val Leu Gly Leu Leu Phe Leu
225                 230                 235                 240

Gly Ala Gly Leu Phe Ile Tyr Phe Arg Asn Gln Lys Gly Gln Ser Gly
                245                 250                 255

Leu Gln Pro Thr Gly Leu Leu Ser
            260

<210> SEQ ID NO 54
<211> LENGTH: 186
<212> TYPE: PRT
<213> ORGANISM: Artificial Sequence
<220> FEATURE:
<223> OTHER INFORMATION: Recombinant

<400> SEQUENCE: 54

Ser Arg Pro Trp Phe Leu Glu Tyr Cys Lys Ser Glu Cys His Phe Tyr
1               5                   10                  15

Asn Gly Thr Gln Arg Val Arg Leu Leu Val Arg Tyr Phe Tyr Asn Leu
            20                  25                  30

Glu Glu Asn Leu Arg Phe Asp Ser Asp Val Gly Glu Phe Arg Ala Val
        35                  40                  45

Thr Glu Leu Gly Arg Pro Asp Ala Glu Asn Trp Asn Ser Gln Pro Glu
    50                  55                  60

Phe Leu Glu Gln Lys Arg Ala Glu Val Asp Thr Val Cys Arg His Asn
65                  70                  75                  80

```
Tyr Glu Ile Phe Asp Asn Phe Leu Val Pro Arg Arg Val Glu Pro Thr
            85                  90                  95

Val Thr Val Tyr Pro Thr Lys Thr Gln Pro Leu Glu His His Asn Leu
        100                 105                 110

Leu Val Cys Ser Val Ser Asp Phe Tyr Pro Gly Asn Ile Glu Val Arg
        115                 120                 125

Trp Phe Arg Asn Gly Lys Glu Glu Lys Thr Gly Ile Val Ser Thr Gly
        130                 135                 140

Leu Val Arg Asn Gly Asp Trp Thr Phe Gln Thr Leu Val Met Leu Glu
145                 150                 155                 160

Thr Val Pro Gln Ser Gly Glu Val Tyr Thr Cys Gln Val Glu His Pro
        165                 170                 175

Ser Leu Thr Asp Pro Val Thr Val Glu Trp
        180                 185

<210> SEQ ID NO 55
<211> LENGTH: 199
<212> TYPE: PRT
<213> ORGANISM: Artificial Sequence
<220> FEATURE:
<223> OTHER INFORMATION: Recombinant

<400> SEQUENCE: 55

Val Arg Asp Thr Arg Pro Arg Phe Leu Glu Tyr Val Thr Ser Glu Cys
1               5                   10                  15

His Phe Tyr Asn Gly Thr Gln His Val Arg Phe Leu Glu Arg Phe Ile
            20                  25                  30

Tyr Asn Arg Glu Glu Asn Leu Arg Phe Asp Ser Asp Val Gly Glu Tyr
        35                  40                  45

Arg Ala Val Thr Glu Leu Gly Arg Pro Asp Ala Glu Asn Trp Asn Ser
    50                  55                  60

Gln Pro Glu Ile Leu Glu Asp Ala Arg Ala Ser Val Asp Thr Tyr Cys
65                  70                  75                  80

Arg His Asn Tyr Glu Ile Ser Asp Lys Phe Leu Val Arg Arg Arg Val
                85                  90                  95

Glu Pro Thr Val Thr Val Tyr Pro Thr Lys Thr Gln Pro Leu Glu His
        100                 105                 110

His Asn Leu Leu Val Cys Ser Val Ser Asp Phe Tyr Pro Gly Asn Ile
        115                 120                 125

Glu Val Arg Trp Phe Arg Asn Gly Lys Glu Glu Glu Thr Gly Ile Val
        130                 135                 140

Ser Thr Gly Leu Val Arg Asn Gly Asp Trp Thr Phe Gln Thr Leu Val
145                 150                 155                 160

Met Leu Glu Thr Val Pro Gln Ser Gly Glu Val Tyr Thr Cys Gln Val
        165                 170                 175

Glu His Pro Ser Leu Thr Asp Pro Val Thr Val Glu Trp Lys Ala Gln
        180                 185                 190

Ser Thr Ser Ala Gln Asn Lys
        195

<210> SEQ ID NO 56
<211> LENGTH: 263
<212> TYPE: PRT
<213> ORGANISM: Mus musculus

<400> SEQUENCE: 56

Met Ala Leu Gln Ile Pro Ser Leu Leu Leu Leu Ala Ala Val Val Val
```

```
1               5                   10                  15
Leu Thr Val Leu Ser Ser Pro Gly Thr Glu Gly Gly Asn Ser Glu Arg
                20                  25                  30

His Phe Val His Gln Phe Gln Pro Phe Cys Tyr Phe Thr Asn Gly Thr
                35                  40                  45

Gln Arg Ile Arg Leu Val Ile Arg Tyr Ile Tyr Asn Arg Glu Glu Tyr
    50                  55                  60

Val Arg Phe Asp Ser Asp Val Gly Glu Tyr Arg Ala Val Thr Glu Leu
65                  70                  75                  80

Gly Arg Pro Asp Ala Glu Tyr Trp Asn Lys Gln Tyr Leu Glu Arg Thr
                85                  90                  95

Arg Ala Glu Leu Asp Thr Val Cys Arg His Asn Tyr Glu Lys Thr Glu
                100                 105                 110

Thr Pro Thr Ser Leu Arg Arg Leu Glu Gln Pro Ser Val Val Ile Ser
                115                 120                 125

Leu Ser Arg Thr Glu Ala Leu Asn His His Asn Thr Leu Val Cys Ser
130                 135                 140

Val Thr Asp Phe Tyr Pro Ala Lys Ile Lys Val Arg Trp Phe Arg Asn
145                 150                 155                 160

Gly Gln Glu Glu Thr Val Gly Val Ser Ser Thr Gln Leu Ile Arg Asn
                165                 170                 175

Gly Asp Trp Thr Phe Gln Val Leu Val Met Leu Glu Met Thr Pro Arg
                180                 185                 190

Arg Gly Glu Val Tyr Thr Cys His Val Glu His Pro Ser Leu Lys Ser
                195                 200                 205

Pro Ile Thr Val Glu Trp Arg Ala Gln Ser Glu Ser Ala Arg Ser Lys
            210                 215                 220

Met Leu Ser Gly Ile Gly Gly Cys Val Leu Gly Val Ile Phe Leu Gly
225                 230                 235                 240

Leu Gly Leu Phe Ile Arg His Arg Ser Gln Lys Gly Pro Arg Gly Pro
                245                 250                 255

Pro Pro Ala Gly Leu Leu Gln
                260

<210> SEQ ID NO 57
<211> LENGTH: 256
<212> TYPE: PRT
<213> ORGANISM: Artificial Sequence
<220> FEATURE:
<223> OTHER INFORMATION: Recombinant

<400> SEQUENCE: 57

Met Pro Arg Ser Arg Ala Leu Ile Leu Gly Val Leu Ala Leu Thr Thr
1               5                   10                  15

Met Leu Ser Leu Cys Gly Gly Glu Asp Asp Ile Glu Ala Asp His Val
                20                  25                  30

Gly Ser Tyr Gly Ile Thr Val Tyr Gln Ser Pro Gly Asp Ile Gly Gln
                35                  40                  45

Tyr Thr Phe Glu Phe Asp Gly Asp Glu Leu Phe Tyr Val Asp Leu Asp
    50                  55                  60

Lys Lys Glu Thr Val Trp Met Leu Pro Glu Phe Ala Gln Leu Arg Arg
65                  70                  75                  80

Phe Glu Pro Gln Gly Gly Leu Gln Asn Ile Ala Thr Gly Lys His Asn
                85                  90                  95

Leu Glu Ile Leu Thr Lys Arg Ser Asn Ser Thr Pro Ala Thr Asn Glu
```

```
                100                 105                 110
Ala Pro Gln Ala Thr Val Phe Pro Lys Ser Pro Val Leu Leu Gly Gln
            115                 120                 125

Pro Asn Thr Leu Ile Cys Phe Val Asp Asn Ile Phe Pro Pro Val Ile
        130                 135                 140

Asn Ile Thr Trp Leu Arg Asn Ser Lys Ser Val Thr Asp Gly Val Tyr
145                 150                 155                 160

Glu Thr Ser Phe Phe Val Asn Arg Asp Tyr Ser Phe His Lys Leu Ser
                165                 170                 175

Tyr Leu Thr Phe Ile Pro Ser Asp Asp Ile Tyr Asp Cys Lys Val
            180                 185                 190

Glu His Trp Gly Leu Glu Glu Pro Val Leu Lys His Trp Glu Pro Glu
                195                 200                 205

Ile Pro Ala Pro Met Ser Glu Leu Thr Glu Thr Val Val Cys Ala Leu
            210                 215                 220

Gly Leu Ser Val Gly Leu Val Gly Ile Val Val Gly Thr Ile Phe Ile
225                 230                 235                 240

Ile Gln Gly Leu Arg Ser Gly Gly Thr Ser Arg His Pro Gly Pro Leu
                245                 250                 255

<210> SEQ ID NO 58
<211> LENGTH: 254
<212> TYPE: PRT
<213> ORGANISM: Artificial Sequence
<220> FEATURE:
<223> OTHER INFORMATION: Recombinant

<400> SEQUENCE: 58

Met Ile Leu Asn Lys Ala Leu Met Leu Gly Ala Leu Ala Leu Thr Thr
1               5                   10                  15

Val Met Ser Pro Cys Gly Gly Glu Asp Ile Val Ala Asp His Val Ala
            20                  25                  30

Ser Tyr Gly Val Asn Leu Tyr Gln Ser Tyr Gly Pro Ser Gly Gln Tyr
        35                  40                  45

Thr His Glu Phe Asp Gly Asp Glu Gln Phe Tyr Val Asp Leu Gly Arg
    50                  55                  60

Lys Glu Thr Val Trp Cys Leu Pro Val Leu Arg Gln Phe Arg Phe Asp
65                  70                  75                  80

Pro Gln Phe Ala Leu Thr Asn Ile Ala Val Leu Lys His Asn Leu Asn
                85                  90                  95

Ser Leu Ile Lys Arg Ser Asn Ser Thr Ala Ala Thr Asn Glu Val Pro
            100                 105                 110

Glu Val Thr Val Phe Ser Lys Ser Pro Val Thr Leu Gly Gln Pro Asn
        115                 120                 125

Ile Leu Ile Cys Leu Val Asp Asn Ile Phe Pro Pro Val Val Asn Ile
    130                 135                 140

Thr Trp Leu Ser Asn Gly His Ser Val Thr Glu Gly Val Ser Glu Thr
145                 150                 155                 160

Ser Phe Leu Ser Lys Ser Asp His Ser Phe Phe Lys Ile Ser Tyr Leu
                165                 170                 175

Thr Leu Leu Pro Ser Ala Glu Glu Ser Tyr Asp Cys Lys Val Glu His
            180                 185                 190

Trp Gly Leu Asp Lys Pro Leu Leu Lys His Trp Glu Pro Glu Ile Pro
        195                 200                 205

Ala Pro Met Ser Glu Leu Thr Glu Thr Val Val Cys Ala Leu Gly Leu
```

```
                210                 215                 220
Ser Val Gly Leu Val Gly Ile Val Gly Thr Val Phe Ile Ile Arg
225                 230                 235                 240

Gly Leu Arg Ser Val Gly Ala Ser Arg His Gln Gly Pro Leu
                245                 250
```

<210> SEQ ID NO 59
<211> LENGTH: 260
<212> TYPE: PRT
<213> ORGANISM: Artificial Sequence
<220> FEATURE:
<223> OTHER INFORMATION: Recombinant

<400> SEQUENCE: 59

```
Met Arg Pro Glu Asp Arg Met Phe His Ile Arg Ala Val Ile Leu Arg
1               5                   10                  15

Ala Leu Ser Leu Ala Phe Leu Leu Ser Leu Arg Gly Ala Gly Ala Ile
                20                  25                  30

Lys Ala Asp His Val Ser Thr Tyr Ala Ala Phe Val Gln Thr His Arg
            35                  40                  45

Pro Thr Gly Glu Phe Met Phe Glu Phe Asp Glu Asp Glu Met Phe Tyr
        50                  55                  60

Val Asp Leu Asp Lys Lys Glu Thr Val Trp His Leu Glu Glu Phe Gly
65                  70                  75                  80

Gln Ala Phe Ser Phe Glu Ala Gln Gly Gly Leu Ala Asn Ile Ala Ile
                85                  90                  95

Leu Asn Asn Asn Leu Asn Thr Leu Ile Gln Arg Ser Asn His Thr Gln
            100                 105                 110

Ala Thr Asn Asp Pro Pro Glu Val Thr Val Phe Pro Lys Glu Pro Val
        115                 120                 125

Glu Leu Gly Gln Pro Asn Thr Leu Ile Cys His Ile Asp Lys Phe Phe
130                 135                 140

Pro Pro Val Leu Asn Val Thr Trp Leu Cys Asn Gly Glu Leu Val Thr
145                 150                 155                 160

Glu Gly Val Ala Glu Ser Leu Phe Leu Pro Arg Thr Asp Tyr Ser Phe
                165                 170                 175

His Lys Phe His Tyr Leu Thr Phe Val Pro Ser Ala Glu Asp Phe Tyr
            180                 185                 190

Asp Cys Arg Val Glu His Trp Gly Leu Asp Gln Pro Leu Leu Lys His
        195                 200                 205

Trp Glu Ala Gln Glu Pro Ile Gln Met Pro Glu Thr Thr Glu Thr Val
210                 215                 220

Leu Cys Ala Leu Gly Leu Val Leu Gly Leu Val Gly Ile Ile Val Gly
225                 230                 235                 240

Thr Val Leu Ile Ile Lys Ser Leu Arg Ser Gly His Asp Pro Arg Ala
                245                 250                 255

Gln Gly Thr Leu
            260
```

<210> SEQ ID NO 60
<211> LENGTH: 255
<212> TYPE: PRT
<213> ORGANISM: Artificial Sequence
<220> FEATURE:
<223> OTHER INFORMATION: Recombinant

<400> SEQUENCE: 60

Met Ala Thr Ile Gly Ala Leu Leu Leu Arg Phe Phe Phe Ile Ala Val
1               5                   10                  15

Leu Met Ser Ser Gln Lys Ser Trp Ala Ile Lys Glu Glu His Thr Ile
            20                  25                  30

Ile Gln Ala Glu Phe Tyr Leu Leu Pro Asp Lys Arg Gly Glu Phe Met
        35                  40                  45

Phe Asp Phe Asp Gly Asp Glu Ile Phe His Val Asp Ile Glu Lys Ser
    50                  55                  60

Glu Thr Ile Trp Arg Leu Glu Glu Phe Ala Lys Phe Ala Ser Phe Glu
65                  70                  75                  80

Ala Gln Gly Ala Leu Ala Asn Ile Ala Val Asp Lys Ala Asn Leu Asp
                85                  90                  95

Val Met Lys Glu Arg Ser Asn Asn Thr Pro Asp Ala Asn Val Ala Pro
            100                 105                 110

Glu Val Thr Val Leu Ser Arg Ser Pro Val Asn Leu Gly Glu Pro Asn
        115                 120                 125

Ile Leu Ile Cys Phe Ile Asp Lys Phe Ser Pro Val Val Asn Val
    130                 135                 140

Thr Trp Phe Arg Asn Gly Arg Pro Val Thr Glu Gly Val Ser Glu Thr
145                 150                 155                 160

Val Phe Leu Pro Arg Asp Asp His Leu Phe Arg Lys Phe His Tyr Leu
                165                 170                 175

Thr Phe Leu Pro Ser Thr Asp Asp Phe Tyr Asp Cys Glu Val Asp His
            180                 185                 190

Trp Gly Leu Glu Glu Pro Leu Arg Lys His Trp Glu Phe Glu Glu Lys
        195                 200                 205

Thr Leu Leu Pro Glu Thr Thr Glu Asn Val Val Cys Ala Leu Gly Leu
    210                 215                 220

Phe Val Gly Leu Val Gly Ile Val Val Gly Ile Ile Leu Ile Met Lys
225                 230                 235                 240

Gly Ile Lys Lys Arg Asn Val Val Glu Arg Arg Gln Gly Ala Leu
                245                 250                 255

<210> SEQ ID NO 61
<211> LENGTH: 254
<212> TYPE: PRT
<213> ORGANISM: Artificial Sequence
<220> FEATURE:
<223> OTHER INFORMATION: Recombinant

<400> SEQUENCE: 61

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

```
Glu Val Thr Val Leu Thr Asn Ser Pro Val Leu Arg Glu Pro Asn
            115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
                180                 185                 190

Trp Gly Leu Asp Glu Pro Leu Leu Lys His Trp Glu Phe Asp Ala Pro
            195                 200                 205

Ser Pro Leu Pro Glu Thr Thr Glu Asn Val Val Cys Ala Leu Gly Leu
    210                 215                 220

Thr Val Gly Leu Val Gly Ile Ile Ile Gly Thr Ile Phe Ile Ile Lys
225                 230                 235                 240

Gly Val Arg Lys Ser Asn Ala Ala Glu Arg Arg Gly Pro Leu
                245                 250

<210> SEQ ID NO 62
<211> LENGTH: 263
<212> TYPE: PRT
<213> ORGANISM: Artificial Sequence
<220> FEATURE:
<223> OTHER INFORMATION: Recombinant

<400> SEQUENCE: 62

Met Ala Leu Gln Ile Pro Ser Leu Leu Leu Ala Ala Val Val Val
1               5                   10                  15

Leu Thr Val Leu Ser Ser Pro Gly Thr Glu Gly Gly Asn Ser Glu Arg
            20                  25                  30

His Phe Val His Gln Phe Gln Pro Phe Cys Tyr Phe Thr Asn Gly Thr
        35                  40                  45

Gln Arg Ile Arg Leu Val Ile Arg Tyr Ile Tyr Asn Arg Glu Glu Tyr
    50                  55                  60

Val Arg Phe Asp Ser Asp Val Gly Glu Tyr Arg Ala Val Thr Glu Leu
65                  70                  75                  80

Gly Arg Pro Asp Ala Glu Tyr Trp Asn Lys Gln Tyr Leu Glu Arg Thr
                85                  90                  95

Arg Ala Glu Leu Asp Thr Val Cys Arg His Asn Tyr Glu Lys Thr Glu
            100                 105                 110

Thr Pro Thr Ser Leu Arg Arg Leu Glu Gln Pro Ser Val Val Ile Ser
        115                 120                 125

Leu Ser Arg Thr Glu Ala Leu Asn His His Asn Thr Leu Val Cys Ser
    130                 135                 140

Val Thr Asp Phe Tyr Pro Ala Lys Ile Lys Val Arg Trp Phe Arg Asn
145                 150                 155                 160

Gly Gln Glu Glu Thr Val Gly Val Ser Ser Thr Gln Leu Ile Arg Asn
                165                 170                 175

Gly Asp Trp Thr Phe Gln Val Leu Val Met Leu Glu Met Thr Pro Arg
            180                 185                 190

Arg Gly Glu Val Tyr Thr Cys His Val Glu His Pro Ser Leu Lys Ser
        195                 200                 205

Pro Ile Thr Val Glu Trp Arg Ala Gln Ser Glu Ser Ala Arg Ser Lys
    210                 215                 220
```

```
Met Leu Ser Gly Ile Gly Gly Cys Val Leu Gly Val Ile Phe Leu Gly
225                 230                 235                 240

Leu Gly Leu Phe Ile Arg His Arg Ser Gln Lys Gly Pro Arg Gly Pro
                245                 250                 255

Pro Pro Ala Gly Leu Leu Gln
            260

<210> SEQ ID NO 63
<211> LENGTH: 261
<212> TYPE: PRT
<213> ORGANISM: Artificial Sequence
<220> FEATURE:
<223> OTHER INFORMATION: Recombinant

<400> SEQUENCE: 63

Met Ser Trp Lys Lys Ala Leu Arg Ile Pro Gly Gly Leu Arg Ala Ala
1               5                   10                  15

Thr Val Thr Leu Met Leu Ser Met Leu Ser Thr Pro Val Ala Glu Gly
            20                  25                  30

Arg Asp Ser Pro Glu Asp Phe Val Tyr Gln Phe Lys Gly Met Cys Tyr
        35                  40                  45

Phe Thr Asn Gly Thr Glu Arg Val Arg Leu Val Ser Arg Ser Ile Tyr
    50                  55                  60

Asn Arg Glu Glu Ile Val Arg Phe Asp Ser Asp Val Gly Glu Phe Arg
65                  70                  75                  80

Ala Val Thr Leu Leu Gly Leu Pro Ala Ala Glu Tyr Trp Asn Ser Gln
                85                  90                  95

Lys Asp Ile Leu Glu Arg Lys Arg Ala Ala Val Asp Arg Val Cys Arg
            100                 105                 110

His Asn Tyr Gln Leu Glu Leu Arg Thr Thr Leu Gln Arg Arg Val Glu
        115                 120                 125

Pro Thr Val Thr Ile Ser Pro Ser Arg Thr Glu Ala Leu Asn His His
    130                 135                 140

Asn Leu Leu Val Cys Ser Val Thr Asp Phe Tyr Pro Ala Gln Ile Lys
145                 150                 155                 160

Val Arg Trp Phe Arg Asn Asp Gln Glu Glu Thr Ala Gly Val Val Ser
                165                 170                 175

Thr Pro Leu Ile Arg Asn Gly Asp Trp Thr Phe Gln Ile Leu Val Met
            180                 185                 190

Leu Glu Met Thr Pro Gln Arg Gly Asp Val Tyr Thr Cys His Val Glu
        195                 200                 205

His Pro Ser Leu Gln Ser Pro Ile Thr Val Glu Trp Arg Ala Gln Ser
    210                 215                 220

Glu Ser Ala Gln Ser Lys Met Leu Ser Gly Ile Gly Gly Phe Val Leu
225                 230                 235                 240

Gly Leu Ile Phe Leu Gly Leu Gly Leu Ile Ile His His Arg Ser Gln
                245                 250                 255

Lys Gly Leu Leu His
            260

<210> SEQ ID NO 64
<211> LENGTH: 258
<212> TYPE: PRT
<213> ORGANISM: Artificial Sequence
<220> FEATURE:
<223> OTHER INFORMATION: Recombinant

<400> SEQUENCE: 64
```

Met Met Val Leu Gln Val Ser Ala Ala Pro Arg Thr Val Ala Leu Thr
1               5                   10                  15

Ala Leu Leu Met Val Leu Leu Thr Ser Val Val Gln Gly Arg Ala Thr
            20                  25                  30

Pro Glu Asn Tyr Leu Phe Gln Gly Arg Gln Glu Cys Tyr Ala Phe Asn
        35                  40                  45

Gly Thr Gln Arg Phe Leu Glu Arg Tyr Ile Tyr Asn Arg Glu Glu Phe
    50                  55                  60

Ala Arg Phe Asp Ser Asp Val Gly Glu Phe Arg Ala Val Thr Glu Leu
65                  70                  75                  80

Gly Arg Pro Ala Ala Glu Tyr Trp Asn Ser Gln Lys Asp Ile Leu Glu
                85                  90                  95

Glu Lys Arg Ala Val Pro Asp Arg Met Cys Arg His Asn Tyr Glu Leu
            100                 105                 110

Gly Gly Pro Met Thr Leu Gln Arg Arg Val Gln Pro Arg Val Asn Val
        115                 120                 125

Ser Pro Ser Lys Lys Gly Pro Leu Gln His His Asn Leu Leu Val Cys
    130                 135                 140

His Val Thr Asp Phe Tyr Pro Gly Ser Ile Gln Val Arg Trp Phe Leu
145                 150                 155                 160

Asn Gly Gln Glu Glu Thr Ala Gly Val Val Ser Thr Asn Leu Ile Arg
                165                 170                 175

Asn Gly Asp Trp Thr Phe Gln Ile Leu Val Met Leu Glu Met Thr Pro
            180                 185                 190

Gln Gln Gly Asp Val Tyr Thr Cys Gln Val Glu His Thr Ser Leu Asp
        195                 200                 205

Ser Pro Val Thr Val Glu Trp Lys Ala Gln Ser Asp Ser Ala Arg Ser
    210                 215                 220

Lys Thr Leu Thr Gly Ala Gly Gly Phe Val Leu Gly Leu Ile Ile Cys
225                 230                 235                 240

Gly Val Gly Ile Phe Met His Arg Arg Ser Lys Lys Val Gln Arg Gly
                245                 250                 255

Ser Ala

<210> SEQ ID NO 65
<211> LENGTH: 264
<212> TYPE: PRT
<213> ORGANISM: Artificial Sequence
<220> FEATURE:
<223> OTHER INFORMATION: Recombinant

<400> SEQUENCE: 65

Met Val Trp Leu Pro Arg Val Pro Cys Val Ala Val Ile Leu Leu
1               5                   10                  15

Leu Thr Val Leu Ser Pro Pro Val Ala Leu Val Arg Asp Ser Arg Pro
            20                  25                  30

Trp Phe Leu Glu Tyr Cys Lys Ser Glu Cys His Phe Tyr Asn Gly Thr
        35                  40                  45

Gln Arg Val Arg Leu Leu Glu Arg Tyr Phe Tyr Asn Leu Glu Glu Asn
    50                  55                  60

Leu Arg Phe Asp Ser Asp Val Gly Glu Phe Arg Ala Val Thr Glu Leu
65                  70                  75                  80

Gly Arg Pro Asp Ala Glu Asn Trp Asn Ser Gln Pro Glu Phe Leu Glu
                85                  90                  95

```
Gln Lys Arg Ala Glu Val Asp Thr Val Cys Arg His Asn Tyr Glu Ile
            100                 105                 110
Ser Asp Lys Phe Leu Val Arg Arg Val Glu Pro Thr Val Thr Val
        115                 120                 125
Tyr Pro Thr Lys Thr Gln Pro Leu Glu His His Asn Leu Leu Val Cys
130                 135                 140
Ser Val Ser Asp Phe Tyr Pro Gly Asn Ile Glu Val Arg Trp Phe Arg
145                 150                 155                 160
Asn Gly Lys Glu Glu Lys Thr Gly Ile Val Ser Thr Gly Leu Val Arg
                165                 170                 175
Asn Gly Asp Trp Thr Phe Gln Thr Leu Val Met Leu Gly Thr Val Pro
            180                 185                 190
Gln Ser Gly Glu Val Tyr Thr Cys Gln Val Glu His Pro Ser Leu Thr
        195                 200                 205
Asp Pro Val Thr Val Glu Trp Lys Ala Gln Ser Thr Ser Ala Gln Asn
        210                 215                 220
Lys Met Leu Ser Gly Val Gly Phe Val Leu Gly Leu Leu Phe Leu
225                 230                 235                 240
Gly Ala Gly Leu Phe Ile Tyr Phe Arg Asn Gln Lys Gly Gln Ser Gly
                245                 250                 255
Leu Gln Pro Thr Gly Leu Leu Ser
            260

<210> SEQ ID NO 66
<211> LENGTH: 264
<212> TYPE: PRT
<213> ORGANISM: Artificial Sequence
<220> FEATURE:
<223> OTHER INFORMATION: Recombinant

<400> SEQUENCE: 66

Met Val Cys Leu Arg Leu Pro Gly Gly Ser Cys Met Ala Val Leu Thr
1               5                   10                  15
Val Thr Leu Met Val Leu Ser Ser Pro Leu Ala Leu Ala Gly Asp Thr
            20                  25                  30
Arg Pro Arg Phe Leu Glu Tyr Ser Thr Ser Glu Cys His Phe Phe Asn
        35                  40                  45
Gly Thr Glu Arg Val Arg Phe Leu Glu Arg Tyr Phe His Asn Gln Glu
    50                  55                  60
Glu Asn Val Arg Phe Asp Ser Asp Val Gly Glu Tyr Arg Ala Val Thr
65                  70                  75                  80
Glu Leu Gly Arg Pro Asp Ala Glu Tyr Trp Asn Ser Gln Lys Asp Leu
                85                  90                  95
Leu Glu Gln Arg Arg Ala Ala Val Asp Thr Tyr Cys Arg His Asn Tyr
            100                 105                 110
Gly Val Gly Glu Ser Phe Thr Val Gln Arg Arg Val His Pro Lys Val
        115                 120                 125
Thr Val Tyr Pro Ser Lys Thr Gln Pro Leu Gln His His Asn Leu Leu
    130                 135                 140
Val Cys Ser Val Ser Gly Phe Tyr Pro Gly Ser Ile Glu Val Arg Trp
145                 150                 155                 160
Phe Arg Asn Gly Gln Glu Glu Lys Thr Gly Val Val Ser Thr Gly Leu
                165                 170                 175
Ile His Asn Gly Asp Trp Thr Phe Gln Thr Leu Val Met Leu Glu Thr
            180                 185                 190
```

```
Val Pro Arg Ser Gly Glu Val Tyr Thr Cys Gln Val Glu His Pro Ser
    195                 200                 205

Val Thr Ser Pro Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
            245                 250                 255

Ser Gly Leu Gln Pro Arg Gly Phe
            260
```

DISULPHIDE BOND-STABILIZED FUNCTIONAL SOLUBLE MHC CLASS II HETERODIMERS

CROSS-REFERENCE TO RELATED APPLICATIONS

The present application is a divisional of U.S. application Ser. No. 13/579,887, filed Dec. 17, 2012, which is a non-provisional application claiming the benefit of International Application No. PCT/GB2011/050325, filed Feb. 18, 2011, which claims the benefit of the earlier filing dates of provisional U.S. Application No. 61/305,728, filed Feb. 18, 2010 and U.S. Application No. 61/316,576, filed Mar. 23, 2010, the entirety of which is incorporated herein by reference.

SEQUENCE LISTING

An electronic copy of the Sequence Listing entitled "P001D_SeqList.txt" is herein incorporated by reference. This Sequence Listing consists of [SEQ. ID NOS: 1-66].

FIELD

The present invention relates to disulphide bond stabilized recombinant MHC class II molecules.

BACKGROUND

The major histocompatibility complex (MHC) molecule is a central component of the vertebrate immune system found on the surface of all nucleated cells. The MHC is found in two major forms, namely as MHC class I and class II. Importantly, both versions form functional complexes with proteolytically processed peptides, denoted T cell epitopes, which takes place within the very same cell that expresses the given MHC. The resulting peptide/MHC (pMHC) complex is subsequently found as a transmembrane complex on the surface of the cell—a phenomenon described as antigen presentation. The cell surface-bound pMHC may then interact with its cognate partner—the T cell receptor (TCR), which is found on the surface of T lymphocytes.

Given its pivotal role in adaptive immunity, basic and applied sciences have a substantial interest in understanding the pMHC-TCR interaction at both the cellular and molecular level and thus to have access to recombinant versions of both molecules. It is also an ever growing understanding that the availability of such recombinant molecules is absolutely critical for being able to study and understand the biology of the system, as well as for developing novel therapeutics and diagnostics.

Many significant medical conditions require therapeutic interventions to modulate the activity of the patient's immune system. In e.g. autoimmune diseases and allergies, the overactive immune system and chronic inflammation needs to be suppressed. In contrast, immunostimulation is an approach relevant for infections and cancers to activate and target the immune cells towards the cancerous cells. In addition, transplant recipients usually require immunosuppression. Together, this has lead to the development of a vast amount of immunomodulators, currently a multi Billion dollar industry.

A key to understanding the immunity component in these diseases, and screen for new treatments, is the interaction between the antigen-presenting cells and the T-cells, or more specifically, the interaction between MHC class I and II molecules and the TCR. The class II MHC specifically binds exogenously derived peptides, and presents them to CD4+ T helper cells (TH cells). The TH cell is then activated and becomes an effector cell that secretes various cytokines. These cytokines activate a wide range of other immune cells involved in taking care of the threat. A failure in this system can lead to e.g. an autoimmune disease or to allow cancer cells to survive and divide. Thus, autoimmune diseases are characterized by a strong MHC association and target organ T cell infiltration.

A platform for immunomodulator screening requires stable, fully functional soluble MHC class II molecules. Importantly, the production of soluble MHC class II molecules is currently hampered by a severe problem, namely lack of molecular stability.

In the last few years the ability to produce soluble MHC class I molecules as tetramers (tetramer technology) has revolutionized basic and applied immunology (Constantin et al., 2002, Biological Research for Nursing, 4: 115-127). The reason for this is that tetramer technology has substantially increased the ability to track the course of an immune response in a specific manner both in terms of the antigen and the T cell response, assessed primarily by flow cytometry. This ability has also translated into a much deeper understanding of the immune system and may indeed also give rise to novel diagnostic tools.

To date, tetramer reagents have to a large extent been limited to the MHC class I molecules, as most technical issues regarding recombinant MHC class I production appear to have been solved. Indeed, with regard to MHC class II molecules, this task has proven significantly more challenging. Thus, no general protocol for the production of MHC class II tetramers is at present available, although stand alone examples appear both in the literature and as commercially available reagents (Vollers, S. and Stern, L., 2008, Immunology 123: 305-313). In the few cases where MHC class II tetramers have been available, they have been used extensively, and have had an enormous impact on the understanding of disease development. Thus, given the impact successful recombinant MHC class I production has already shown, it can be seen that there is a strong and clear cut motivation, both academic and commercial, for putting further efforts into novel MHC class II production avenues. However, given the problems encountered to date, success is uncertain.

Due to partially unknown reasons, the MHC class II molecule has proven especially difficult to produce as a stable recombinant molecule in soluble form. The native molecule is a non-covalent transmembrane heterodimer comprising an α- and a β-chain, both of which have transmembrane regions and belong to the immunoglobulin (Ig) superfamily. The extracellular portion of each chain is composed of two domains, each consisting of approximately 90 amino acid residues, of which the two membrane distal domains, the α1 and β1 domains, form an inter-latticed α/β structure essential for the peptide binding property of the T cell epitopes. The two membrane proximal domains, the α2 and the β2 domains, both form discrete Ig domains. In both the α and the β chain, a stretch of approximately 20 amino acid residues spans the cell membrane and on the cytoplasmic side of the membrane a fairly short peptide segment is located.

The dimerization of the α and the β chain is thought to be caused by (i) the transmembrane segments, (ii) peptide binding and (iii) putative accessory components found in the membrane. Hence, once separated from its native context and produced as a soluble molecule, the MHC class II molecule often suffers from intrinsically low stability and very low production levels. Furthermore, extensive and resource demanding case-dependent optimization must be carried out.

In addition, given the above requirements for dimerization, general methods of production of MHC class II molecules in any non-native context, i.e. in any context other than production in association with a membrane of a cell which cell naturally expresses MHC class II molecules, e.g. production as non-soluble molecules displayed on the surface of other biological entities, cells or particles, e.g. as non-soluble molecules expressed on the surface of a phage by way of fusion to viral capsid proteins, is thought to be far from straightforward.

Thus, there is at present no general strategy which exists which allows the production of a stabilized MHC class II heterodimer. However, a variety of studies have been carried out that all represent case-specific successful examples that rather reflect the complexity of the task. These examples are (i) the ectopic expression of a membrane-bound MHC class II heterodimer on the surface of eukaryotic cells by use of a lipid tether (GPI anchor), see Wettstein et al., 1991, J. of Exp. Medicine, 174: 219-228; (ii) the expression of MHC class II ectodomains in insect cells, see Wallny et al., 1995, Eur. J. Immunology, 25: 1262-1266; (iii) the introduction of heterologous dimerization motifs, such as the leucine zipper, C-terminally into the MHC class II molecules, in combination with insect cell production, see Quarsten et al., 2001, J. Immunol., 167: 4861-4868, and Crawford et al., 2006, Immunological Reviews, 210: 156-170; (iv) the production of antibody/MHC class II chimeras in combination with insect cell production, see Casares et al., 1997, Protein Engineering, 10: 1295-1301; (v) the use of bacterial expression systems that allow formation of functional pMHC trimers through refolding approaches from inclusion bodies, see Arimilli et al., 1995, J. Biol. Chem., 270:971-977; or (vi) the use of a truncated bacterial produced single chain MHC class II format which is comprised of the α1 and β1 domains only, that allows formation of functional MHC molecules through refolding approaches from inclusion bodies, see Burrows et al., 1999, Protein Engineering, 12: 771-778. In addition, Landais et al., 2009, J. Immunol., 183:7949-7957, describes an insect cell expression system which uses internal artificial disulphide bridges in conjunction with exogenous leucine zippers for producing stabilized murine I-A$^d$ OVA MHC class II tetramers. Importantly, and despite increased expression levels due to the modification, none of these apparently stabilized-increased molecules exhibited specific T cell staining.

DETAILED DESCRIPTION

The strategies described herein provide significant advantages over such prior art systems as they not only provide a general strategy which can be applied to all MHC class II molecules but can also be implemented in a prokaryotic expression system and do not require the use of heterologous/exogenous dimerization motifs such as leucine zippers. Moreover, the strategies described herein translate to increase in functionality seen as specific T cell staining, directly attributed to the modifications introduced.

Surprisingly however, the present inventors have identified a general method by which the instability problems associated with recombinant MHC class II molecules can be overcome, or to a large extent alleviated. This strategy involves the production of recombinant MHC class II molecules in which extracellular portions of the α and the β chain are present and the α and β chain heterodimer is stabilized by an engineered/artificial disulphide bridge linking the two chains using the α2-β2 domain interface. The disulphide bond locks the molecule in a stable conformation, where it is fully functional. Importantly, and advantageously, this strategy for stabilizing the MHC class II heterodimer is versatile and not-limited to a single recombinant format, thus avoiding the need for the extensive and resource demanding case-dependent optimization discussed above. In addition, unlike in a number of the existing methods, this strategy can be implemented in a prokaryotic expression system/host which is in itself surprising, given the fact that prokaryotic hosts lack the complex machinery of a eukaryotic cell, which is generally required for correct di-sulphide bridge formation and hence the formation of functional molecules. This invention will not only solve a current issue hampering the field of exploring and developing immunomodulators, but will also be an important tool for developing and modifying T-cells and using these as therapy.

Thus, in one aspect the present invention provides a recombinant MHC class II molecule, which comprises:

(i) all or part of the extracellular portion of an MHC class II α chain;

(ii) all or part of the extracellular portion of an MHC class II β chain; wherein (i) and (ii) provide a functional peptide binding domain and wherein (i) and (ii) are linked by a disulphide bond between cysteine residues located in the α2 domain of said α chain and the β2 domain of said β chain, wherein said cysteine residues are not present in native MHC class II α2 and β2 domains.

As mentioned above, proteins such as MHC class II molecules, which are made up of more than one polypeptide and which have a transmembrane domain, can be difficult to produce outside the context of their native membranes, and in particular in a soluble format, because, in many cases, the protein is stabilized by, amongst other things, its transmembrane region and possibly membrane accessory components. This is the case for MHC class II molecules and is reflected in the literature where MHC class II molecules are reported as being unstable, cannot be produced in a good yield or cannot recognize and bind to peptides. Thus, the molecules of the present invention represent a major advance over the prior art as they are stable and can also recognize and bind to peptides, as well as allowing staining of T cells.

As discussed above, native MHC class II molecules comprise an α- and a β-chain, both of which have transmembrane regions and belong to the immunoglobulin (Ig) superfamily. The extracellular portion of each chain is composed of two domains, each consisting of approximately 90 amino acid residues, of which the two membrane distal domains, the α 1 and β1 domains, form an inter-latticed α/β structure essential for the peptide binding property of the T cell epitopes. The two membrane proximal domains, the α2 and the β2 domains, both form discrete Ig domains. In both the α and the β chain, a stretch of approximately 20 amino acid residues spans the cell membrane and on the cytoplasmic side of the membrane a fairly short peptide segment is located.

The molecules of the present invention comprise all or part of the extracellular portion of an MHC class II α chain and all or part of the extracellular portion of an MHC class II β chain. The extracellular portion of an MHC class II α chain comprises a signal sequence, a membrane distal al domain and a membrane proximal α2 domain (which forms a discrete Ig domain). There is also a spacer region between the transmembrane domain and the α2 domain. Likewise, the extracellular portion of an MHC class II β chain comprises a signal sequence, a membrane distal β1 domain, a membrane proximal β2 domain (which forms a discrete Ig domain) and a spacer region.

The term "extracellular portion of an MHC class II β chain" as used herein thus does not include the transmembrane domain or the cytoplasmic domain of the α chain.

Indeed, in preferred embodiments of the invention the recombinant MHC class II molecules do not include any of the amino acid residues of said transmembrane domain (i.e. the amino acids encoded by the dedicated transmembrane exons) or any of the amino acid residues of said cytoplasmic domains.

Similarly, the term "extracellular portion of an MHC class II β chain" as used herein thus does not include the transmembrane domain or the cytoplasmic domain of the β chain. Indeed, in preferred embodiments of the invention the recombinant MHC class II molecules do not include any of the amino acid residues of said transmembrane domain (i.e. the amino acids encoded by the dedicated transmembrane exons) or any of the amino acid residues of said cytoplasmic domains.

All of said extracellular portions of the α and/or β chain may be present in the recombinant molecules of the invention (i.e. the signal peptide, the α1/β1 domain, the α2/β2 domain and the spacer region). However, alternatively, only part of the extracellular portion of the α and/or β chain need be present in the molecules of the invention providing that the recombinant molecules are still functional in terms of their ability to bind to an appropriate peptide, e.g. a T cell effector peptide, and providing that said molecules contain the artificial (non-native) cysteine residues in a form or configuration such that they can be used to form the disulphide bond which functions to stabilize the recombinant MHC class II molecule.

The signal peptide may be omitted from the α and/or β chains of the recombinant MHC molecules of the invention, in particular if the MHC class II molecule is to be expressed in prokaryotic cells. Such constructs in which the appropriate number of N-terminal amino acid residues are omitted can readily be designed and produced by a person skilled in the art. It can also readily be tested as to whether such omissions have an effect on function, e.g. ability to bind peptide or activate or stain T cells, or on stability of the molecule.

The spacer region can also be omitted in its entirety or can be truncated, for example as shown in the experimental Examples in which none of the α chain spacer and 9 amino acids of the β chain spacer are included. Again, such constructs in which the appropriate number of spacer amino acid residues are omitted can readily be designed and produced by a person skilled in the art. It can also be tested as to whether such omissions have an effect on function, e.g. ability to bind peptide or activate or stain T cells, or on stability of the molecule.

Preferred molecules of the invention comprise at least a part of an α1 domain and at least a part of a β1 domain providing that the function of such domains to bind peptides or other functions as described herein, for example in order to present such peptides to T cell receptors (TCRs), is not effected. In addition, the recombinant MHC class II molecule as a whole must still be functional in terms of ability to bind peptides or other functions as described herein, e.g. in order to present such peptides to T cell receptors (TCRs). Preferably complete or full length α1 and/or β1 domains are present, or essentially complete or essentially full length α1 and/or β1 domains are present, wherein said essentially complete or essentially full length domains contain variations from the native sequence, for example amino acid additions, deletions or substitutions, which do not affect the function of such domains to bind peptides or other functions as described herein, e.g. in order to present such peptides to T cell receptors (TCRs). Determining which amino acid residues can be mutated, modified or deleted without affecting such function would be within the skill of a person skilled in the art. Other preferred functions to be retained by the MHC class II molecules are the ability to activate T cells and more preferably the ability to stain T cells.

Thus, these preferred molecules of the invention comprise sufficient residues of the α1 and β1 domains so as to be able to bind peptides, for example in order to present such peptides to TCRs, to activate T cells or to allow the staining of T cells.

Other preferred molecules of the invention comprise at least a part of an α2 domain and at least a part of a β2 domain providing that the non-native cysteine residues which are used to form the disulphide bond are present. Such cysteine residues need to be present at appropriate orientations and distances from each other such that the disulphide bridge can form between the cysteine residues and can act to stabilize the recombinant MHC class II molecule. In addition, the recombinant MHC class II molecule as a whole must still be functional in terms of ability to bind peptides or other functions as described herein, e.g. in order to present such peptides to T cell receptors (TCRs). Preferably complete or full length α2 and/or β2 domains are present, or essentially complete or essentially full length α2 and/or β2 domains are present, wherein said essentially complete or essentially full length domains contain variations from the native sequence, for example amino acid additions, deletions or substitutions, which do not affect the formation of the disulphide bond between the α2 and β2 domains and the subsequent stabilization of the recombinant MHC class II molecule and do not deleteriously effect the folding of the α2 or β2 domains. Determining which amino acid residues can be mutated, modified or deleted without affecting such function would be within the skill of a person skilled in the art.

The amino acid location of the various structural and functional domains and regions of the α and β MHC class II chains are well known and described in the art, for example Burrows et al, 1999, supra. The location of the various domains is also shown in FIG. 3 and such information can readily be used to design the recombinant molecules of the invention as described herein (see for example FIG. 7).

Appropriate functional tests to assess the ability of the recombinant molecules of the invention to bind peptide, to activate T cells or to stain T cells would also be well known to a person skilled in the art and would include for example surface plasmon resonance (SPR) techniques such as Biacore and flow cytometry techniques such as FACS. The use of flow cytometry is particularly preferred as this can be used in combination with live cells.

The term "disulphide bond" as used herein refers to any disulphide bridge, e.g. an engineered or artificial disulphide bridge, which is formed between cysteine residues located in the α2 domain of the α chain and the β2 domain of the β chain of an MHC class II heterodimer (i.e. is an inter-chain as opposed to an intra-chain disulphide bond). Said disulphide bond forms a covalent linkage between the α chain and the β chain and acts to stabilize the MHC class II heterodimer. Thus, the recombinant molecules of the invention are stable but retain full functionality, for example, they retain their native specificity towards their cognate T cell receptor ligands, and preferably retain their ability to activate T cells or to stain T cells.

The property of an MHC class II molecule of the invention to be stable or stabilized can be assessed by well known methods such as increased resistance to thermal denaturation (measured for example by ELISA, SPR, or circular dichroism). A more preferred test is to assess for preserved heterodimers on an SDS PAGE gel. Intact and stable disulphide bonded heterodimers can readily be seen on an SDS PAGE gel run under non-reducing conditions, where a band at an appropriate molecular weight corresponding to an intact heterodimer can be visualised. An appropriate assay is shown in the Examples, see FIGS. 5 and 10.

Such disulphide bonds are formed between cysteine residues which are not normally present in native MHC class II α2 and β2 domains. Thus, such cysteine residues are engineered or artificially introduced, e.g. by site specific mutation of appropriate non-cysteine residues in the native molecule to cysteine residues, thereby allowing formation of a disulphide bond between the newly introduced cysteine residues in the α2 and β2 domains. Such bonds can also be described as internal disulphide bonds.

Appropriate residues for mutation to cysteine preferably have respective β-carbons which are approximately 6 Å (0.6 nm), 7 Å (0.7 nm) or less apart, for example in the range of 4 Å (0.4 nm) or 5 Å (0.5 nm) to 6.5 Å (0.65 nm) or 7 Å (0.7 nm), preferably in the range of 5 Å (0.5 nm) to 6.5 Å (0.65 nm), most preferably in the range of 4 Å (0.4 nm) or 5 Å (0.5 nm) to 5.6 Å (0.56 nm) or 6 Å (0.6 nm) apart in the native MHC class II heterodimer. Preferred sites for mutation are conserved between species and between isoforms and isotypes within a particular species. In particular, preferred sites for mutation are conserved between mouse and human MHC class II sequences or are conserved between the human MHC class II isotypes such as DP, DQ and DR or between the mouse isotypes such as I-E and I-A.

Alternatively, or in addition, preferred sites for mutation are identified by a structural assessment based on 3D superimposition of crystal structures. In this way, residues forming the interface between the α2 and β2 domains can be examined and side chains with β-carbons at a distance of 7 Å or less apart (or indeed any of the other distances or ranges described above) can be chosen for further analysis or mutation to cysteine residues. Methods for carrying out such a structural assessment would be well known to a person skilled in the art. For example, crystal structures of MHC class II molecules are freely available for this analysis to be carried out, for example from the RCSB PDB Protein Data Bank. Appropriate software or other means for carrying out such a 3D superimposition of crystal structures are also available in the art, for example using freely available software such as PyMOL, MOLMOL, DeepView or dedicated web sites such as iSuperpose.

Especially preferred pairs of sites where cysteines are introduced to form the disulphide bond are one or more of the following pairs, i.e. one or more of Pro $96^{\alpha_2}$-Ser $119^{\beta_2}$ (rank 1), Ser $95^{\alpha_2}$-Ser $121^{\beta_2}$ (rank 2), Arg $94^{\alpha_2}$-Asn $151^{\beta_2}$ (rank 3), Phe $148^{\alpha_2}$-Gly $152^{\beta_2}$ (rank 4), Pro $96^{\alpha_2}$-Thr $101^{\beta_2}$ (rank 5), Pro $96^{\alpha_2}$-Ser $121^{\beta_2}$ (rank 6), Ile $106^{\alpha_2}$-Asn $151^{\beta_2}$ (rank 7) and Ser $95^{\alpha_2}$-Asp $122^{\beta_2}$ (rank 8). The pairs are ranked according to the proximity of the β carbons and although any of these pairs can be used, the pairs ranked 1 to 4 or 1 to 3 are preferred. The rank 1 or rank 2 pair is particularly preferred.

The amino acid location and nature of the native amino acid at that location in the pairs of residues located in the α2 and β2 domains and described above are appropriate for MHC class II molecules of the murine I-E isotype. The amino acid numbering relates to the amino acids of the mature peptide (i.e. the numbering excludes the signal peptide). An exemplary reference sequence which can be used to identify the location of the modified cysteine residues is the I-E sequence given in the IMGT database, which is shown in FIG. 3 (denoted as H-2EA*02 for the α chain (SEQ ID NO:1) and H-2EB*01 for the β chain (SEQ ID NO:2)). Indeed, the residues of the rank 1, rank 2 and rank 3 positions are marked in black shading in FIG. 3, and the positions of the other ranked residues can readily be determined from FIG. 3.

Thus, unless otherwise stated, the numbering and nature of the MHC class II amino acid residues described herein follows the IMGT system described in Lefranc, M-P., et al., 2009 (Nuc. Acids Res., 37: D1006-D1012, database issue) together with the IMGT databases found at the following website references: imgt.cines.fr; world wide web at imgt.org. Relevant GenBank accession numbers are also provided in the Examples. For example, for the H-2E (murine I-E) the relevant accession numbers are K00971 (α-chain) and AF050157 (β-chain).

In preferred embodiments of the invention the disulphide bond is located between cysteine residues positioned at residues corresponding to Pro $96^{\alpha_2}$-Ser $119^{\beta_2}$ (rank 1), Ser $95^{\alpha_2}$-Ser $121^{\beta_2}$ (rank 2) or Arg $94^{\alpha_2}$-Asn $151^{\beta_2}$ (rank 3) of the mature polypeptides of a murine I-E isotype or the equivalent locations in an alternative MHC class II isotype. Reference sequences for determining the location of such cysteine residues are provided herein.

The above discussed preferred pairs of sites are also shown in Table 2 using both 1FNG numbering, i.e. one or more of Pro $96^{\alpha_2}$-Ser $118^{\beta_2}$ (rank 1), Ser $95^{\alpha_2}$-Ser $120^{\beta_2}$ (rank 2), Arg $94^{\alpha_2}$-Asn $150^{\beta_2}$ (rank 3), Phe $148^{\alpha_2}$-Gly $151^{\beta_2}$ (rank 4), Pro $96^{\alpha_2}$-Thr $100^{\beta_2}$ (rank 5), Pro $96^{\alpha_2}$-Ser $120^{\beta_2}$ (rank 6), Ile $106^{\alpha_2}$-Asn $150^{\beta_2}$ (rank 7) and Ser $95^{\alpha_2}$-Asp $121^{\beta_2}$ (rank 8) and IMGT numbering. For the 1FNG numbering, the amino acid numbering of Table 2 corresponds to the numbering in the Protein Data Bank (PDB) database of three dimensional structural information of biological macromolecules, entry number PDB ID: 1FNG, and it can be seen that the location of the appropriate residues in the β chain of this database entry are one amino acid less than the equivalent residues in the IMGT database sequence. Thus, this nomenclature is slightly different.

The equivalent residues to those shown in Table 2 and FIG. 3 can readily be identified in other murine isotypes, e.g. I-A isotypes, or human isotypes, by for example alignment using appropriate software such as Clustal software. Indeed, an alignment with a murine I-A isotype is shown in FIG. 3. In addition, exemplary alignments with human MHC class II allotypes HLA-DP, -DQ and -DR are shown in FIG. 7. The location of the equivalent residues to those of rank 1, 2 and 3 shown in Table 2 and FIG. 3 are marked in black shading on FIG. 7A for the α-chain and on FIG. 7B for the β-chain, and the positions of the other ranked residues can readily be determined from FIG. 7. It can be seen that the α2 and β2 positions shown in Table 2 and FIG. 3 are fully conserved throughout the human HLA repertoire.

Thus, the sequence alignments shown in FIG. 7 together with the information above can be used to readily locate the appropriate residues to mutate to cysteines in the α2 and β2 domains of any human MHC class II allele in order to form the desired rank of disulphide bond. Similar alignment methods can be used to identify the equivalent residues in any other species or isotype.

The disulphide bond stabilizing linkages as discussed herein are compatible with other methods and means of stabilizing MHC class II molecules such as those described in the prior art. For example, the disulphide bonds can be used in conjunction with various dimerization motifs such as leucine zipper motifs (e.g. as described in Quarsten et al., 2001 and Crawford et al., 2006, supra), or in conjunction with Ig fusions (i.e. fusions to an Fc portion of an immunoglobulin, e.g. as described in Casares et al., 1997, supra) and the molecules of the invention, together with the vectors encoding them, can be designed appropriately.

As described elsewhere herein expression or production of the molecules of the invention in prokaryotic, e.g. bacterial, hosts is preferred and in such embodiments, particularly in embodiments where molecules are isolated from inclusion bodies, it is preferred that leucine zipper motifs or other dimerization motifs are not used.

Thus, a preferred aspect of the invention provides a recombinant MHC class II molecule capable of being expressed in a bacterial host, which comprises:

(i) all or part of the extracellular portion of an MHC class II α chain;

(ii) all or part of the extracellular portion of an MHC class II β chain;

wherein (i) and (ii) provide a functional peptide binding domain and wherein (i) and (ii) are linked by a disulphide bond between cysteine residues located in the α2 domain of said α chain and the β2 domain of said β chain, wherein said cysteine residues are not present in native MHC class II α2 and β2 domains.

Another preferred aspect provides a recombinant MHC class II molecule, which comprises:

(i) all or part of the extracellular portion of an MHC class II α chain;

(ii) all or part of the extracellular portion of an MHC class II β chain; wherein (i) and (ii) provide a functional peptide binding domain and wherein (i) and (ii) are linked by a disulphide bond between cysteine residues located in the α2 domain of said α chain and the β2 domain of said β chain, wherein said cysteine residues are not present in native MHC class II α2 and β2 domains, and further wherein said recombinant molecule does not comprise a leucine zipper motif. In other embodiments, no dimerization motif is included. In these embodiments it is preferred that the recombinant MHC class II molecule is capable of being expressed in a prokaryotic, e.g. bacterial, host.

Although the disulphide bond linkages of the invention can be used in conjunction with other methods and means of stabilizing MHC class II molecules, said disulphide bonds can provide the sole means of stabilizing the MHC class II molecules. Indeed, such embodiments are preferred. The term "sole means of stabilizing the MHC class II molecules" as used herein refers to the disulphide bonds providing the sole or only means of stabilizing the molecules beyond any stabilization which exists naturally or inherently in a particular MHC class II molecule, e.g. the disulphide bonds of the invention provide the sole or only artificial or engineered or non-native means of stabilizing the MHC class II molecule. Thus, such embodiments exclude the use of other stabilizing means described in the art such as leucine zippers or other dimerization motifs.

The surprising finding that such disulphide bonds are sufficient to stabilize MHC class II molecules without any additional non-native means of stabilization such as a dimerization motif is elegantly demonstrated in the data provided herein where such molecules are displayed in a stable and functional form on the surface of filamentous phage. This finding was particularly surprising given the facts that the engineered molecules, which are built on the Ig fold topology, were expressed in a prokaryotic host. The Ig fold, which in nature only occurs in the eukaryotic domain of life, requires conserved intradomain S-S bridges to be formed between native cysteines (Halaby, D. M., et al., 1999, Protein Eng., 12 (7): 563)) to reach its functional topology. It is therefore generally accepted that when such molecules are expressed in a prokaryotic host, which inevitably lacks the complex chaperone machinery of the eukaryotic cell required for correct S-S bridge formation, aberrant S-S bridge formation is prominent, resulting in lack of functional expression. Engineering strategies involving an increased number of cysteines, not to say defined artificial S-S bridge formation in these systems, are hence generally considered nonviable. Here, we clearly provide evidence that this is not the case, as functional molecules are displayed on the phage as shown by covalent dimer formation (FIGS. 5 and 10) exhibiting specific binding to the cognate ligand (FIG. 6 and FIG. 9).

In one embodiment, the α and β chains of the MHC class II molecules of the invention also comprise intra-chain disulphide bonds, e.g. naturally occurring intra-chain disulphide bonds which exist between naturally occurring cysteine residues. Such naturally occurring intra-chain disulphide bonds can for example exist in the α2 and β2 domains in order to form the Ig fold topology of these domains. In addition, most MHC class II molecules harbor an intradomain disulphide bridge in the β1 domain connecting the β-sheet floor with the α-helix portion. More importantly, many MHC class II molecules contain an additional free cysteine in the β-sheet floor of the β1 domain, which do not participate in any disulphide bridge formation but which could form erroneous disulphide bonds with the newly introduced non-native cysteine residues. Thus, in preferred embodiments of the invention, in particular in embodiments where prokaryotic expression is used, this residue is removed, for example by mutation to an alternative residue which preserves the overall structure, such as serine or alanine. A skilled person would readily be able to locate this cysteine residue in any MHC class II allele. For example, this cysteine corresponds to the β-chain residue 38 in the full length IMGT reference sequence H-2EB*01 shown in FIG. 3B (SEQ ID NO: 2), or residue 12 in the mature IMGT reference sequence (i.e. without the signal peptide).

The other β1 domain cysteines (which form a bridge) but which also could contribute to erroneous disulphide bond formation with the newly introduced non-native cysteine residues could also readily be located by a skilled person. For example, these are located at residues 42 and 106 in the full length IMGT reference sequence H-2EB*01 shown in FIG. 3B (SEQ ID NO:2), or residues 16 and 80, respectively, of the mature IMGT reference sequence (i.e. without the signal peptide). In alternative and preferred embodiments of the invention one or more of such cysteine residues are not present. This can be achieved by mutating one or more of the appropriate native cysteine residues to another amino acid residue which is not involved in disulphide bond formation in order to prevent the bond forming. Exemplary residues to replace the cysteines would be those that preserved the overall structure of the molecule, e.g. preserved the hydrogen bonding. Either Ser or Ala as discussed above would be preferred choices.

The above discussed removal of one or more native cysteine residues should thus help to prevent erroneous disulphide bond formation between native cysteine residues and the newly engineered non-native cysteine residues of the invention. Thus, in preferred embodiments of the invention, one or more native cysteine residues in the β1 domain are removed. In especially preferred embodiments of the invention, one or more of the cysteine residues corresponding to positions 38, 42 or 106 of the full length reference sequence H-2EB*01 (SEQ ID NO:2) (or the equivalent residues in the mature reference sequence) or one or more cysteine residues at equivalent locations in an alternative MHC class II isotype are removed.

The term "functional peptide binding domain" as used herein refers to a domain in the recombinant MHC class II molecule of the invention which is capable of binding to a peptide, e.g. a T cell effector peptide or an antigenic peptide. Such peptide binding should be at a detectable level and appropriate methods for detecting binding would be well known to a person skilled in the art, e.g. surface plasmon resonance (SPR) techniques or flow cytometry techniques. In some embodiments said peptides are bound in such a way as to enable presentation of said peptide to a TCR, or at least to test whether or not said peptide is capable of being presented to a TCR.

Preferably such peptides are bound or associated with the MHC class II molecule in such a way as to enable binding of a TCR to the pMHC complex. More preferably such an interaction with a TCR allows the T cells which recognise the pMHC complex to be stained or otherwise visualised. Preferably such a peptide binding domain is capable of binding to a peptide and then initiating activation of T cells via the TCR, e.g. is capable of inducing T Helper cells to for example secrete cytokines such as IL-2, or to induce proliferation (measured e.g by BrdU incorporation as cpm). Such peptide binding domains are generally formed by residues from the α1 and β1 domains of the MHC class II molecules.

The MHC class II molecules of the invention may be provided in an empty or unloaded form, i.e. without a peptide bound to the above described peptide binding domain (i.e. peptide free). In this case, the MHC class II molecules can then subsequently be loaded with any appropriate peptide in vitro. Such in vitro loading is advantageous over many prior art MHC class II molecules, which, to help stability of the class II heterodimer, have to be produced with peptides attached, e.g. by way of the peptides being produced as a covalent fusion protein with the MHC β chain via a short linker. In vitro loading allows a truly generic MHC class II molecule to be produced without having to provide a different expression vector for each different MHC-peptide complex.

In some embodiments of the invention, the recombinant MHC class II molecules have peptides bound to or associated with the above described peptide binding domain. Any peptide which is suitable to bind to or associate with the peptide binding domain formed by residues from the α1 and β1 domains of the MHC class II molecules can be used. Generally such peptides are 12-25 mers and usually protrude out at both ends of the groove formed by the α 1 and β1 domains.

In native MHC class II molecules such peptides are derived from exogenous antigens. In the present invention, any such peptides may be used. For example, some specific T cell effector peptides which are presented by MHC class II molecules and result in TCR binding and T cell activation have been identified and documented in the art and any of these may be used in conjunction with the present invention. In particular, certain peptides presented on MHC class II molecules have been identified as being associated with particular diseases and in embodiments of the invention where the recombinant MHC class II molecules are associated with peptide, such disease specific peptides are preferred. Some of these peptides are described in the art and others will be identified in the future; any of these peptides will be suitable for use with the described MHC class II molecules.

Exemplary peptides which associate or bind to the peptide binding domain of MHC class II molecules are human α-II-gliadin (N-PQPELPYPQPE-C, SEQ ID NO:16), which has been found to be presented on HLA-DQ2 MHC class II molecules and which is associated with celiac disease; human $hC_{kappa}^{aa40-48}$ (N-WKIDGSERQ-C, SEQ ID NO:5), which has been found to be presented on HLA-DR4 MHC class II molecules and which is associated with rheumatoid arthritis; human $TT^{a947-967}$ (N-FNNFTVSFWLRVPKVSASHLE-C, SEQ ID NO:6) which has been found to be presented on HLA-DP1 MHC class II molecules and which is associated with tetanus; and a peptide derived from hemaglutinin (HA) from H. influenza (aa110-120: N-SFERFEIFPKE-C, SEQ ID NO:7), which has been found to be presented on mouse I-E$^d$ class II molecules.

Alternatively, other peptides can be used, for example to identify whether such peptides can bind to the peptide binding domain and also whether they can enable T cell binding and preferably T cell staining via the TCR or enable T cell activation. In this way the molecules of the invention can be used to identify new and previously unknown peptides (e.g. antigenic peptides) which act as T cell epitopes.

Alternatively, the recombinant MHC class II molecules can be associated with irrelevant or non-T cell effector peptides (so called "stuffer" peptides) which can be released from the MHC class II molecule through cleavage of a linker attaching it to the MHC molecule and can then be replaced with T cell effector peptides of interest in an in vitro peptide-exchange reaction.

Binding or association of such peptides with the MHC class II molecule can be facilitated in any appropriate way. For example, it is possible to engineer the constructs of the invention such that such peptides are produced in conjunction with the MHC class II molecules (e.g. by encoding them on the same construct, e.g. encoding them covalently linked to the β MHC class II chain or the α MHC class II chain via an appropriate linker sequence, or a different construct in the same host cell) thereby allowing the production of recombinant MHC class II molecules which present or are bound to or associated with said peptide suitable for recognition by appropriate T helper cells. Appropriate methods to produce such peptide associated molecules are described by Kozono et al. 1994 (Nature, 369:151-154). The Kozono methods use an 18 aa residue linker, however in preferred embodiments of the invention a shorter linker such as a 15 aa linker (e.g. Gly-Ser linkers such as $(G_4S)_3$, SEQ ID NO:8) or a 6, 7 or 8 aa residue linker (e.g. Gly-Ser linkers such as GSGSGS (SEQ ID NO:9), GGSGSGS (SEQ ID NO:10), SGSGSGS (SEQ ID NO:11) or SGGSGSGS (SEQ ID NO:12)), most preferably a 6 aa residue linker, are used.

The present invention is generally applicable to any type of MHC class II molecule, for example is applicable to MHC class II molecules from any species and any sub-type of MHC class II molecules within that species. In particular, the residues identified herein for mutation to non-native cysteine residues to allow the formation of one or more inter-chain disulphide bonds are conserved between species, thereby supporting the generality of the approach. The present invention can thus be applied to all mammalian MHC class II molecules, e.g. human, mouse, rat, pig, goat and sheep, in particular human and mouse molecules. For example, the present invention is applicable to DP, DQ and DR human MHC class II molecules (i.e. the three identified functional types of MHC class II molecules in humans) and also to mouse I-A and I-E molecules (for example I-E$^d$ and I-E$^k$ molecules, preferably I-E$^d$). Other examples of I-A and I-E molecules are shown in the Table below.

| MHC alleles expressed by commonly used inbred mouse strains. | | | | | | | |
|---|---|---|---|---|---|---|---|
| | | | H-2 | | | | |
| | | | Class I | | | Class II | |
| Strain | Appearance | Haplotype | K | D | L | IA | IE |
| Balb/c | albino | d | Kd | Dd | Ld | Iad | Ied |
| C3H/He | agouti | k | Kk | Dk | — | Iak | Iek |

-continued

MHC alleles expressed by ccommonly used inbred mouse strains.

| | | | H-2 | | | | |
| --- | --- | --- | --- | --- | --- | --- | --- |
| | | | Class I | | | Class II | |
| Strain | Appearance | Haplotype | K | D | L | IA | IE |
| C57BL/6 | black | b | Kb | Db | — | Iab | — |
| CBA | agouti | k | Kk | Dk | — | Iak | Iek |

Most preferably the MHC class II molecules are human.

As the identified residues for mutation to cysteine are conserved across species a person skilled in the art could readily identify the corresponding, equivalent and appropriate residues for mutation in any MHC class II molecule from any species and thus produce recombinant MHC class II molecules stabilized by one or more appropriate inter-chain disulphide bond.

In one embodiment of the invention the recombinant MHC class II molecule is expressed on the surface of a cell or another biological entity or package, for example on the surface of a filamentous phage. This format may sometimes be referred to herein as "non-soluble" format or "non-soluble" molecules. In such embodiments, either the α chain or the β chain of the MHC class II molecules of the invention are generally engineered as fusion proteins with a protein which is normally expressed on the surface of the entity in question or are otherwise embedded or associated with the surface of the entity in question.

Expression as a fusion to a phage surface protein is preferred and in such embodiments fusion of either the α chain or the β chain of the MHC class II molecules of the invention with any appropriate phage surface protein is envisaged. Preferred examples are fusions to gpIII, gpVIII, gpVII or gpIX, more preferably gpIII. Methodology for the expression of MHC class II molecules of the invention on the surface of phage particles would be within the skill of a person skilled in the art and exemplary techniques and methods are described in the Examples. Preferred methodology is for example described in WO09/024591.

In alternative embodiments of the invention, the recombinant MHC molecules are soluble molecules, for example MHC class II molecules of the invention which are not associated with or expressed on the surface of a cell or other biological entity such as as a fusion to viral capsid protein or other proteins which result in association with or complexing to the surface of the biological entity. Exemplary soluble molecules thus include molecules comprising only the extracellular portions (i) and (ii) of the molecules of the invention, but also include such ectodomains including other short components which do not effect the solubility of the molecules such as short C-terminal extensions such as affinity tags and/or dimerization motifs. Depending on the production system such soluble molecules may be secreted from host cells or obtained from host cells by any other appropriate method. Such soluble molecules may be provided in a substantially pure form or as a purified or isolated preparation. For example such soluble molecules may be produced in a form which is substantially free of other proteins.

In preferred embodiments of the invention, the recombinant MHC class II molecules may be provided in a multimeric form e.g. with multivalent properties. Such multimeric forms are often advantageous to enable binding of MHC class II molecules to T cell receptors as the affinity between a single pMHC complex and a T cell receptor is generally quite low.

Such multimeric forms comprise a plurality (more than one) of the recombinant MHC class II molecules of the invention. Preferably each of the plurality of MHC class II molecules is identical.

Any appropriate method of preparing multimeric forms of the MHC class II molecules may be used, several of which are described in the art (see for example Vollers et al., 2008, supra). A particularly advantageous way of preparing multimeric formats of the MHC class II molecules of the invention is by using display on the surface of filamentous phage. In such methods, the natural architecture of the phage molecules can be harnessed in order to produce multimers by selecting the appropriate phage structural protein to which the MHC class II molecules are fused and associated. For example fusion to the gpIII, gpVII or gpIX, preferably gpIII, can be used to achieve 3 to 5 copies of the MHC class II molecules on the surface of each phage particle. Fusion to gpVIII can be used to achieve many more copies than this (in the wild type phage there are approximately 2700 copies of gpVIII). Thus, importantly, pVIII display increases the MHC valency by at least one order of magnitude as compared to both gpIII display and classical tetramer technology, which results in a great increase in sensitivity. This should open up new and interesting applications.

Known phage display and construct design techniques, for example the use of phagemid constructs and modified types of helper phage, can be used to alter the number of copies of the MHC class II molecules on the surface of the phage. With the ability to make polymeric MHC class II molecules on the surface of phage, advantageously this allows the manufacture or production of a multimeric MHC class II molecule in one single fast, cost effective, process. This is in stark contrast to conventional tetramer technology such as that described in Vollers et al., 2008, where each component is produced separately, mixed, complexed and purified before the reagent is suitable for downstream applications.

Preferred multimers thus comprise two or three or four or five or more recombinant MHC class II molecules associated with one another. Such association can be carried out using methods known and described in the art but is generally mediated via another linkage such as a linker molecule. Suitable linker molecules are well known and described in the art and particularly appropriate linker molecules will have multiple binding sites to which the recombinant molecules can be attached. For example, multiple attachment molecules such as avidin and streptavidin (or any other molecule which binds biotin in a multivalent manner) may be used which each have multiple binding sites for biotin. Thus, incorporation of biotin into the recombinant MHC molecules by methods known in the art (e.g. using AviTag or other BirA substrates to enable enzymatic biotinylation) will allow the formation of multimers, e.g. tetramers of MHC molecules. Labels can also conveniently be incorporated into multimeric forms, e.g. using fluorescent streptavidin or by the fusing of a label to a phage coat protein, for example a different type of coat protein than the one chosen for MHC class II molecule display. Incorporation of such labels allows ready detection of the tetramers by various known techniques. For example use of a fluorescent label allows flow cytometry techniques such as FACS analysis to be used, which is particularly advantageous.

The MHC class II molecules of the invention or mutimers thereof might also be coated onto a solid support such as a planar or particulate solid support, e.g. a membrane, a plate or a bead. Techniques for this are well known and documented in the art.

The MHC class II molecules of the invention and the use of one or more engineered disulphide bonds between the α2 and β2 domains of an MHC class II molecule to stabilize said molecule as described herein are compatible with all prior art methods of MHC class II molecule production. Thus, the invention is compatible with any of the previous formats of MHC class II molecules described in the art and should improve efficiency of production and stability of product. In particular, the invention expands the applicability and versatility of recombinant MHC class II as such molecules now may be produced in a disulphide bond stabilized form for example as (i) functional, soluble molecules in the periplasm of bacteria, (ii) non-functional components of bacterial inclusion bodies which can be solubilised and refolded into functional entities following purification, preferably with substantially higher yields than that yielded by the current standard protocols (which is a maximum of 30% of the starting material, see e.g. Arimilli et al, 1995, supra), (iii) phage displayed components in filamentous phage systems, iv) Ig fusions in eukaryotic cells; and (v) soluble MHC class II molecules in eukaryotic cells.

Advantageously, approaches (ii)—the inclusion body approach, and (iii)—the phage display approach, will immediately allow two very important applications for effective use of recombinant MHC class II molecules, of which approach (iii) is completely novel. In this regard, successful functional display of pMHC class II on filamentous phage virions has never before been achieved and opens up a set of new, or improved, applications such as (a) phage displayed peptide libraries in the context of MHC class II; (b) extremely rapid and easy production of any given pMHC class II combinations; and (c) multivalent filamentous phage display of MHC class II molecules as an alternative to conventional pMHC class II multimers such as tetramers, except that the virions can be produced at a fraction of the cost and at high speed.

The MHC class II molecules of the invention have particular value and use as a research reagent. This is particularly the case for the multivalent forms described herein and for the phage display forms (which can be readily be designed to be multivalent due to the inherent architecture of the phage particles on which the MHC class II molecules are displayed). Tetrameric forms and phage displayed forms of the MHC class II molecules, in particular multivalent phage displayed forms, are thus preferred for this use. Tetrameric forms of the MHC class II molecules of the invention or multivalent phage displayed forms can be used as preferred alternative reagents for any application in which conventional tetramers are used. A preferred application in which the molecules of the invention can be used as an alternative to conventional tetramers is in MHC staining of T cells which generally involves flow cytometry based detection of T cells using pMHC oligomers such as dimers and higher order oligomers. Data presented herein shows that the MHC molecules of the present invention can be used in flow cytometry analysis to stain T cells. This is a highly advantageous and important property as many MHC class II tetramers of the prior art are unable to stain antigen specific TH cells, even if such tetramers can activate T cells. Thus, preferred MHC class II molecules of the invention have the ability to detectably stain T cells, for example using flow cytometry. This property is particularly observed with multimeric or multivalent forms of the molecules, although staining of T cells can be observed using monomeric forms. A further advantage of multimeric phage display forms is that, in general, lower titres of phage can be using to achieve the same result, e.g. T cell staining.

When such MHC class II molecules are provided as reagents, as described above, they can be provided with or without an associated peptide. Such reagents can be provided as proteins, or as nucleic acids encoding such MHC class II molecules, for example in the form of one or more expression vectors.

Such reagents, in particular when used for T cell staining as described above, can be used to study T cell responses to particular peptides, for example to study repertoire and dynamics of T cell response and to allow direct ex vivo analysis of antigen specific CD4+ T cells, e.g. in peripheral blood. The analysis of peripheral blood has to date been a challenge where recombinant MHC class II molecules are concerned. They can also be used to isolate and identify antigen specific T cells both in vivo, in vitro and ex vivo. T cells identified in this way can be subjected to further study, expansion or activation and have potential for use in therapy.

The recombinant MHC class II molecules of the invention can also be used as a platform to screen for immunomodulators. A critical step in diseases which involve the immune system is the interaction between antigen presenting cells and T-cells. In particular the MHC class II complex on antigen presenting cells is critical as it binds exogenously derived peptides and presents them to T helper cells. The T helper cell is then activated and secretes various cytokines which activate a wide range of effector cells.

The provision of stable, fully functional MHC class II molecules such as those described herein, and in particular soluble formats of such molecules, is vital in order to provide a platform for screening for immunomodulators which can modulate, e.g. up or down regulate, the interaction between T helper cells and MHC class II molecules and subsequent activation of T helper cells and effector cells. Until the present invention such screening had been hampered by the difficulty in producing stable MHC class II molecules at high yield and at low cost. The recombinant MHC class II molecules of the invention can thus be used as a screening platform for immunomodulators.

Preferred MHC class II molecules for use in such methods are described elsewhere herein. Preferably said MHC class II molecules are associated with disease specific peptides. Examples of such peptides are described herein and in the prior art and include the human HLA-DQ2 molecule associated with disease specific peptides such as celiac disease or type I diabetes specific peptides, the human HLA-DR4 MHC class II molecule associated with disease specific peptides for rheumatoid arthritis and the human HLA-DP 1 MHC class II molecule associated with specific tetanus peptides. Other peptides associated with MHC class II molecules of the invention can equally be used.

T cells which can specifically recognize such disease associated peptides in the context of MHC class II are then identified, for example using the MHC class II molecules of the invention as described above, or otherwise obtained (for example some such cell lines have already been developed by scientists) after which the ability of one or more compounds to modulate the interaction between T cells and antigen presenting cells or events downstream thereof, such as cytokine secretion and effector cell function can then be assessed.

The recombinant MHC class II molecules of the invention, and in particular the phage displayed format of such molecules, can be used in epitope discovery, e.g. for the identification and characterization of antigenic peptide epitopes recognized by T cells (T cell epitopes). Thus, a further embodiment of the invention provides a method for identifying antigenic peptide epitopes which can be recognized by T cells, wherein said method comprises the steps of contacting a recombinant MHC class II molecule of the invention with a T cell receptor and detecting binding of said recombinant MHC class II molecule to said T cell receptor. Binding of the T cell receptor is indicative of the presence of an antigenic peptide epitope associated with the MHC class II molecule, after which such epitope can be further analysed and characterized.

For example, a library of epitopes can be created by inserting diversity into the antigenic peptide displayed in the context of a fixed MHC. Such libraries can then be screened for example using recombinant, soluble TCRs or phage displayed TCRs, or other T cell populations, e.g. T cells from patients. This will be a major improvement as compared to current methods which are based on low throughput baculovirus libraries and which suffer the further disadvantage of not being able to carry out selection on live cells (Crawford et al., 2004, PLos Biology, 2: 0523-0533).

The recombinant MHC class II molecules of the invention can be used as diagnostic reagents. For example, as described elsewhere herein, disease specific peptides can be complexed to or associated with the MHC class II molecules of the invention and these can be used to detect the presence or absence of disease specific T cells in samples, e.g. blood samples, taken from a patient which potentially has the disease. The presence of disease specific T cells, and in particular significant numbers of disease specific T cells compared for example to the levels seen in a disease free patient, would indicate a positive diagnosis.

Thus, a further aspect of the invention provides a method of detecting antigen specific T cells in a sample, wherein said method comprises the steps of contacting a recombinant MHC class II molecule of the invention with said sample and detecting binding of said recombinant MHC class II molecule to said T cells. Binding of said recombinant MHC class II molecule to T cells is indicative of the presence of antigen specific T cells.

Such methods can be used to detect the presence of disease specific T cells in a sample and to diagnose the presence or absence of disease. Appropriate diseases which can be diagnosed using such methods are those in which MHC class II molecules are associated with disease specific peptides. Exemplary diseases are described elsewhere herein and include celiac disease, rheumatoid arthritis, tetanus and influenza.

The captured disease specific T cells and the interaction between such T cells and the MHC class II molecules of the invention can also be characterized in order to more fully understand the mechanisms behind specific diseases. Thus, this is another example of how the MHC class II molecules of the invention can be used as research reagents, e.g. to monitor and characterize specific T cell responses.

The recombinant MHC class II molecules of the invention, when associated with peptides, can also be used as a target in TCR affinity maturation.

A person skilled in the art will appreciate that the recombinant MHC class II molecules of the invention may be prepared in any of several ways well known and described in the art, but are most preferably prepared using recombinant methods.

Thus, gene cloning techniques may be used to produce an MHC class II molecule of the invention and appropriate techniques are disclosed for example in J. Sambrook et al., Molecular Cloning, 2nd edition, Cold Spring Harbor Laboratory Press, 1989. Thus, nucleic acid molecules comprising a sequence encoding α chain (e.g. an α and/or a β chain) of the MHC class II molecule of the invention, or a sequence complementary thereto form yet further aspects of the invention.

Nucleic acid molecules encoding the α chain (i.e. chain (i)) or the β chain (i.e. chain (ii)) of the MHC class II molecules as described herein can be derived or produced by any appropriate method, e.g., by cloning or synthesis. Such sequences could, for example, be prepared by cloning appropriate sequences from appropriate sources, for example from cells such as leukocytes isolated from standard buffy coats, PCR techniques such as standard RT-PCR, can be used to clone appropriate sequences using appropriate primers designed using the sequences of the particular MHC class II allele concerned, which are available in GenBank, but more easily accessible through the IMGT database. Complete gene synthesis could also be carried out, especially for prokaryotic expression as this would allow codon optimization which can be important to maximize yield.

Once the initial sequences are cloned or synthesised, then any necessary modifications to the sequences to obtain nucleic acid molecules encoding the mutated cysteine residues of the invention can be made using methods well known and described in the art, for example by site directed mutagenesis.

In addition, if desired or necessary, other parts of the α and/or β chains of the MHC class II molecules can be manipulated in order to produce the molecules of the invention. Thus, for example, the nucleotides encoding the transmembrane and cytoplasmic domains may be removed, as may any other regions which are deemed unnecessary for the molecules of the invention to be functional.

Once nucleic acid fragments encoding the two chains of the MHC class II molecules of the invention have been obtained, these fragments can be further manipulated by standard recombinant DNA techniques, for example to include other desired components, regulatory sequences, etc., or to incorporate the non-native cysteine residues or to remove native cysteine residues as described elsewhere herein. Typically, or as part of this further manipulation procedure, the nucleic acid fragments encoding the MHC class II molecules of the invention are incorporated into one or more appropriate expression vectors and said vector(s) is incorporated into a host cell in order to facilitate production of the MHC class II molecules of the invention. Such expression vectors and host cells containing such expression vectors form yet further aspects of the invention.

Thus, a yet further aspect provides an expression construct or expression vector comprising one or more of the nucleic acid molecules of the invention. Preferably the expression constructs or vectors are recombinant. Preferably said constructs or vectors further comprise the necessary regulatory sequences for the transcription and translation of the protein sequence encoded by the nucleic acid molecule of the invention.

A yet further aspect provides a host cell comprising one or more expression constructs or expression vectors of the invention. Also provided are host cells comprising one or more of the nucleic acid molecules of the invention. A host cell expressing an MHC class II molecule of the invention forms a yet further aspect.

A yet further aspect of the invention provides a method of producing an MHC class II molecule of the present invention, e.g. comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the encoded α and β chains of the MHC class II molecules; and optionally (ii) isolating or obtaining the protein from the host cell or from the growth medium/supernatant. Such methods of production may also comprise a step of purification of the protein product. Preferably, such methods of production are carried out in a prokaryotic, e.g. a bacterial, host cell such as those described elsewhere herein.

Thus, a yet further aspect of the invention provides a method of producing a recombinant MHC class II molecule, which comprises:

(i) all or part of the extracellular portion of an MHC class II α chain;

(ii) all or part of the extracellular portion of an MHC class II β chain; wherein (i) and (ii) provide a functional peptide binding domain and wherein (i) and (ii) are linked by a disulphide bond between cysteine residues located in the α2 domain of said α chain and the β2 domain of said β chain, wherein said cysteine residues are not present in native MHC class II α2 and β2 domains, said method comprising expressing said recombinant molecule in a prokaryotic, preferably a bacterial, host.

As discussed above, the fact that prokaryotic host cells can be used to produce functional MHC class II molecules of the invention incorporating di-sulphide bonds is surprising and advantageous.

As the MHC class II molecules of the invention are made up of more than one polypeptide chain (i.e. are heterodimers), then in some embodiments, for example, for embodiments which involve phage display, bacterial periplasmic expression and eukaryotic expression, then all the polypeptides are preferably expressed in the same host cell, either from the same or a different expression vector, so that the complete dimeric proteins can assemble in the host cell and be isolated or purified therefrom. For other embodiments such as bulk production in bacteria by way of deliberate inclusion body production, each chain must be expressed in separate host cells (notably the same type/strain of host cells).

Any appropriate production systems can be used (e.g. prokaryotic and eukaryotic systems can both be used) and the expression vectors are chosen and designed accordingly to ensure compatibility with the host cell used. Thus, the expression vectors are "suitable for transformation of a host cell", means that the expression vectors contain one or more nucleic acid molecules of the invention and regulatory sequences selected on the basis of the host cells to be used for expression, which are operatively linked to the nucleic acid molecules. Operatively linked is intended to mean that the nucleic acid is linked to regulatory sequences in a manner that allows expression of the nucleic acid.

In embodiments of the invention where the MHC class II molecules are in a non-soluble format, e.g. displayed on the surface of another biological particle or membrane, the display of the MHC molecules of the invention can be achieved by methods which are described in the art. For example, in preferred embodiments of the invention where the MHC class II molecules are displayed on the surface of a filamentous phage, any appropriate art described methods can be used. For example, standard texts such as "Phage Display in Biotechnology and Drug Discovery" by Sachdev S. Sidhu, 1995, or "Phage Display: A Laboratory Manual" by Barbas et al., 1994 can be referred to. Exemplary methods and systems are for example described in WO09/024591 or are as shown in the experimental Examples.

In general, the use of phagemid vectors is preferred for the phage display aspects of the invention and these require the use of appropriate helper strains which can readily be selected by a person skilled in the art. Many appropriate helper phage strains are commercially available such as for example VCSM13 helper phage (Stratagene) and HyperPhage™ (Progen Biotechnik GmbH) and any of these may conveniently be used. Conveniently one chain of the MHC class II heterodimer, i.e. either the α chain or the β chain, is incorporated in the vector as a fusion to the chosen coat protein, e.g. gpIII or one of the other coat proteins as discussed elsewhere herein, whilst the other chain is produced as a soluble molecule, i.e. not as a fusion to a coat protein. Fusion to a coat protein is generally carried out at the N-terminus of said coat protein. In the attached Examples, the β chain is produced as a fusion to the coat protein and the α chain is produced in a soluble form.

Other appropriate components can also be present in the constructs/phagemid vectors, many of which are standard in such vectors. For example, signal sequences such as pelB to direct the proteins to the periplasmic space are generally incorporated, together with for example appropriate promoter/operator sequences, ribosome binding sites, origins of replication, transcription terminators, etc. An exemplary phagemid vector and components is shown in FIG. 2 and one or more of these components can be incorporated into the expression vectors of the present invention.

In embodiments of the invention where a peptide for binding to the peptide binding domain of the recombinant MHC class II molecule is to be provided then conveniently these can also be incorporated into the constructs/expression vectors in an appropriate position. Generally these are produced as covalent fusions to the α or β chain, for example to the N-terminus of the β chain, by way of a linker peptide, examples of which are described elsewhere herein.

In embodiments of the invention where the MHC class II molecules are in a soluble format, such molecules may be obtained by expression as inclusion bodies in a bacterial host cell such as E. coli., and subsequent refolding in vitro. Such refolding in vitro can take place under suitable refolding conditions using standard protocols (e.g. as described in Qoronfleh et al., 2007, Protein Expression and Purification 55: 209-224) and appropriate modifications thereof.

Alternatively, soluble MHC class II molecules of the invention may be obtained by expression in a bacterial host cell such as E. coli, wherein said molecules are produced in the periplasm of such hosts. Production in the periplasm can be achieved by use of an appropriate expression vector, for example incorporating a signal peptide such as pelB which directs the protein to the periplasmic space.

Production of the MHC class II molecules of the invention in a prokaryotic host, in particular a bacterial host, is a preferred embodiment of the invention. Such methods of production are compatible with both the phage display and soluble formats of the MHC class II molecules described herein and can be used to provide large quantities of highly purified protein. Production as soluble molecules from inclusion bodies is particularly preferred in order to obtain large quantities of highly purified protein. The recombinant MHC class II molecules of the invention, which have increased stability by the inclusion of engineered disulphide bonds, are particularly suited for high yield inclusion body production and preferably enable a higher yield production of functional MHC class II molecules from inclusion bodies than can presently be achieved (presently yields in the range of less than 10% of the starting material are quite normal).

Any appropriate prokaryotic or bacterial host can be used for such production. Preferred host cells would be Gram negative host cells, more preferably E. coli. Appropriate E. coli hosts for phage display formats would be well known to a person skilled in the art and include for example XL1-Blue™. Preferred E. coli hosts for the production of soluble formats, in particular, where purification from inclusion bodies is concerned are E. coli K12 derivatives, most preferably those with the BL21 phenotype and derivatives thereof (Terpe, K., Appl Microbiol Biotechnol. 2006 September; 72(2):211-22).

Appropriate bacterial hosts for soluble periplasmic expression would be well known to a person skilled in the art (see for example the review by Terpe, K., Appl Microbiol Biotechnol. 2006 September; 72(2):211-22).

Alternatively, soluble MHC class II molecules of the invention may be obtained by expression in a eukaryotic cell system, such as yeast (including pichia), mammalian or insect cells. Appropriate host cells for such production techniques would be well known to a person skilled in the art. A preferred embodiment of the invention using eukaryotic host cells is to produce the recombinant MHC class II molecules of the invention as a fusion to an Fc portion of an immunoglobulin (Ig), i.e. as an Ig fusion, for example as described in Casares et al., 1997, supra. In such embodiments, an Fc portion of an immunoglobulin molecule, e.g. the Fc portion of an IgG2a molecule, can be fused to the α or the γ MHC class II chain (typically to the C-terminus of the β chain) and used to achieve dimerization of the α and β chains of the recombinant MHC class II molecules of the invention (i.e. molecules containing the artificial disulphide bonds of the invention). Such molecules can be expressed in an insect cell system (or another appropriate system), e.g. by infecting insect cells with baculovirus, whereby secreted di-sulphide bond stabilized MHC class II molecules can be produced.

Suitable regulatory sequences for use in the expression vectors of the invention may be derived from a variety of sources, including bacterial, fungal, viral, mammalian, or insect genes (for example, see the regulatory sequences described in Goeddel, 1990, Gene Expression Technology: Methods in Enzymology 185, Academic Press, San Diego, Calif., 1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The expression vectors of the invention may also contain a selectable marker gene that facilitates the selection of host cells transformed or transfected with a recombinant molecule of the invention. Examples of selectable marker genes are genes encoding a protein such as neomycin and hygromycin that confer resistance to certain drugs, β-galactosidase, chloramphenicol acetyltransferase, firefly luciferase, or an immunoglobulin or portion thereof such as the Fc portion of an immunoglobulin preferably IgG. It will be appreciated that selectable markers can be introduced on a separate vector from the nucleic acid of interest.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags, HA tags, FLAG tags or myc tags). For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Other optional components of the expression vectors include biotinylation sequences (in particular for embodiments involving multimeric formats) such as AviTag or another BirA substrate, labels for detection, e.g. fluorescent labels to enable flow cytometry techniques to be carried out.

Expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofection, electroporation or microinjection. Suitable methods for transforming and transfecting host cells can be found in Sambrook et al., 1989, and other laboratory textbooks. For aspects of the invention involving phage display, a general purpose phage display textbook such as "Phage Display in Biotechnology and Drug Discovery" by Sachdev S. Sidhu, 1995, or "Phage Display: A Laboratory Manual" by Barbas et al., 1994 can be referred to for relevant techniques.

N-terminal or C-terminal fusion proteins comprising the proteins of the invention conjugated to other molecules may be prepared by fusing through recombinant techniques. The resultant fusion proteins contain a protein of the invention fused to a further selected protein, e.g. a marker protein or tag protein as described herein. The proteins of the invention may also be conjugated to other proteins by other known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins that may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Irrespective of the manner of preparation of nucleic acid molecules encoding a first MHC class II molecule of the invention, further suitable variant nucleic acid molecules may be readily prepared by standard molecular biological techniques. In order to confirm that any variant, mutant or second generation nucleic acid molecule encoding an MHC class II molecule of the invention is suitable for use in the present invention, the nucleic acid molecule will be tested to confirm functionality as described elsewhere herein. Preferably, the variant, mutant or second generation nucleic acid segment will also be tested to confirm hybridization under standard, more preferably, standard stringent hybridization conditions. Exemplary suitable hybridization conditions include hybridization in about 7% sodium dodecyl sulfate (SDS), about 0.5 M $NaPO_4$, about 1 mM EDTA at about 50° C.; and washing with about 1% SDS at about 42° C.

As used herein and in the appended claims, the singular forms "a," "an," and "the" include plural reference unless the context clearly dictates otherwise.

BRIEF DESCRIPTION OF THE DRAWINGS

The invention will be further described with reference to the following non-limiting Examples with reference to the following drawings in which:

FIG. 3 shows ClustalW2.02 multiple sequence alignments comparing the IMGT reference α-(A) and β-chain (B) sequences of the murine MHC class II molecule I-E and I-A with those of the cloned I-E$^d$ (marked_EL) and I-E$^k$ (marked 1FNG). The positions chosen for cysteine substitutions are highlighted in black shading (numbered according to Table 2/mature IMGT I-E seq.): rank 1 (α96-β118/α96-β119), rank 2 (α95-β120/α95-β121) and rank 3 (α94-β150/α94-β151). The full length IMGT sequence of the α chain is shown (H-2EA*02) and is sometimes referred to herein as SEQ ID NO:1. The full length IMGT sequence of the β chain is shown (H-2EB1*01) and is sometimes referred to herein as SEQ ID NO:2. The mature IMGT sequence of the α chain, i.e. the full length sequence excluding the signal peptide, is sometimes referred to herein as SEQ ID NO:3 (H-2EA*02 excluding the signal peptide). The mature IMGT sequence of the β chain, i.e. the full length sequence excluding the signal peptide, is sometimes referred to herein as SEQ ID NO:4 (H-2EB1*01 excluding the signal peptide). The α-chain sequence of the cloned I-E$^k$ (H-2EA__1 FNG) has the sequence identifier of SEQ ID NO:50. The α-chain sequence of the cloned I-E$^d$ (H-2EA_EL) has the sequence identifier of SEQ ID NO:51. The α-chain sequence of the murine MHC class II molecule I-A (H-2AA*02) has the sequence identifier of SEQ ID NO:52. The β-chain sequence of the cloned I-E$^k$ (H-2EB__1 FNG) has the sequence identifier of SEQ ID NO:54. The β-chain sequence of the cloned I-E$^d$ (H-2EB_EL) has the sequence identifier of SEQ ID NO:55. The β-chain sequence of the murine MHC class II molecule I-A (H-2AB*02) has the sequence identifier of SEQ ID NO:56. The annotation above each sequence is done in reference to PDB ID: 1FNG and Burrows et al., 1999, Protein Engineering, 12: 771-778.

FIG. 7 shows ClustalW2.02 multiple sequence alignments of the IMGT representative murine and human MHC class II allotypes I-E, I-A, HLA-DP, -DQ and -DR sequences. The α-chain alignment is shown in A and the β-chain alignment is shown in B, respectively. The positions identified for cysteine substitutions as shown in Table 2, FIG. 1 and FIG. 3, is highlighted in black shading. The positions identified are all located in the conserved α2/β2 domains. The α-chain of MHC class II allotype I-A (H-2AA) has the sequence identifier SEQ ID NO:57. The α-chain of MHC class II allotype HLA-DQ (HLA-DQA) has the sequence identifier SEQ ID NO:58. The α-chain of MHC class II allotype HLA-DP (HLA-DPA) has the sequence identifier SEQ ID NO:59. The α-chain of MHC class II allotype I-E (H-2EA) has the sequence identifier SEQ ID NO:60. The α-chain of MHC class II allotype HLA-DR (HLA-DRA) has the sequence identifier SEQ ID NO:61. The β-chain of MHC class II allotype I-A (H-2AB) has the sequence identifier SEQ ID NO:62. The β-chain of MHC class II allotype HLA-DQ (HLA-DQB) has the sequence identifier SEQ ID NO:63. The β-chain of MHC class II allotype HLA-DP (HLA-DPB) has the sequence identifier SEQ ID NO:64. The β-chain of MHC class II allotype I-E (H-2EB) has the sequence identifier SEQ ID NO:65. The β-chain of MHC class II allotype HLA-DR (HLA-DRB) has the sequence identifier SEQ ID NO:66.

FIG. 8 shows that superimposing 8 different human HLA class II structures shows that the quaternary structure of the molecules is highly conserved despite extensive genetic polymorphism; hence validating the alignments in FIG. 7 at the structural level (FIG. 8A). Focusing in on e.g. the R94$^{α2}$-N150$^{β2}$ residue pair (rank 3, Table 2) in the globally superimposed structures in A, reveals a highly conserved positioning with a global RMSD variation from 0.29 to 1.18 Å (FIG. 8B). These structures can thus be regarded as virtually identical at the topological level as the differences observed are merely within the experimental variation expected for independent structures of a single molecule.

EXAMPLES

Example 1

Materials and Methods

Figure 1:
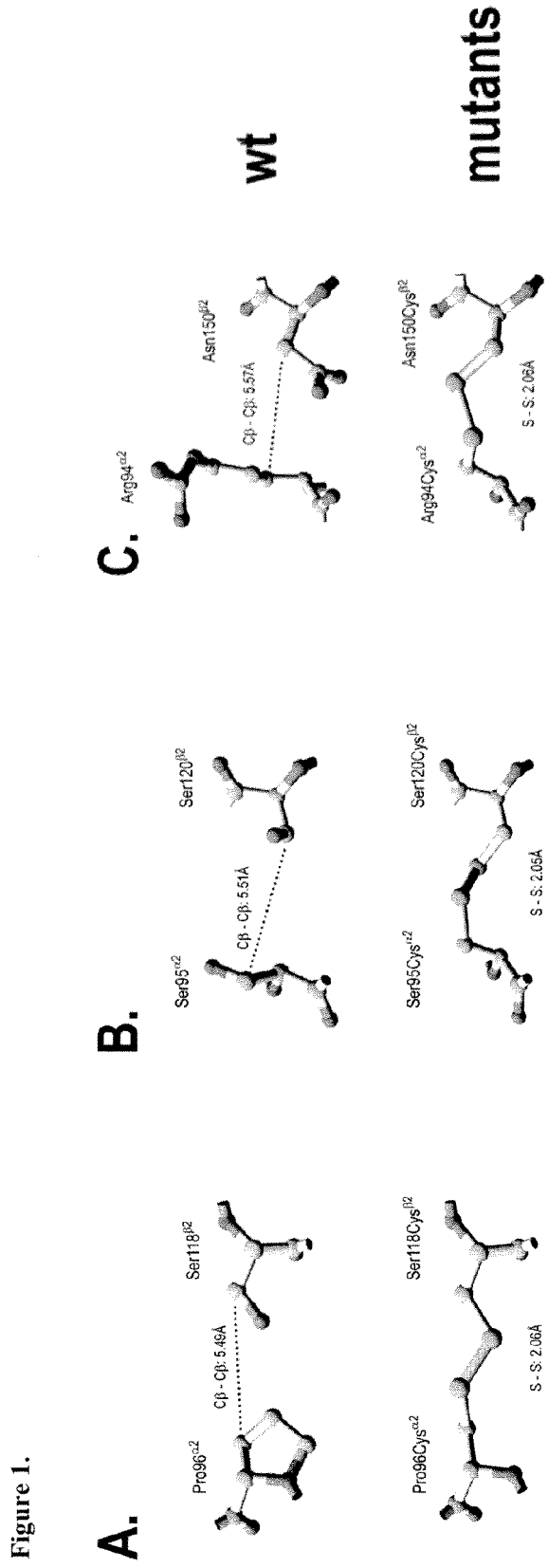
FIG. 1 shows in silico modelling of putative disulphide bridges connecting the α2-β2 domains of the murine MHC class II molecule I-E$^k$ (PDB: 1FNG). Both the wt (upper panel) and the corresponding mutant residues (lower panel) of the top three ranking aa pairs in Table 2 are shown: rank 1 (A), rank 2 (B) and rank 3 (C) including the relevant atomic distances.

Structural Assessment, Molecular Modelling and Sequence Analysis

The 1.9 Å resolution crystal structure (PDB ID: 1FNG) of the murine MHC class II molecule I-E$^k$ in complex with Hemoglobin (Hb)-derived peptide (Hb$^{aa65-76}$)[1] was used for initial disulphide bond predictions. Residues forming the interface between the α2-β2 constant domains were examined and side chains whose β-carbons were in a distance less than 7 Å were chosen for further analysis. First, the selected side chains were changed to cysteines by in silico mutagenesis whereby the optimal rotamers were chosen by a rotamer library scan. In cases where the thiol-groups of the chosen residue pair were in sub-optimal position for disulphide bond formation, the χ1 dihedral angle of the side chains was manually rotated to a favourable position. Local geometries where then optimized by a constrained energy minimization using the Gromos96 force field.

The translated murine IMGT reference sequences for H-2E (GenBank accession no: K00971 and AF050157) and H-2A GenBank accession no: V00832 and M13538), our cloned H-2E$^d$ (see below) and the PDB: 1FNG H-2E sequences were aligned with ClustalW2.02 (world wide web at ebi.ac.uk/) and manually annotated. The representative murine H-2A and E, as well as human HLA-DP, DQ and DR was downloaded from IMGT (imgt.cines.fr/textes/IMGTrepertoireMHC/LocusGenes/RepresentativeMHCgc.html) translated and aligned with ClustalW2.02 (world wide web at ebi.ac.uk/). The IMGT reference sequences used were (GenBank accession codes (α-chain/β-chain)): I-A (V00832/M13538), I-E (K00971/AF050157), HLA-DP (X03100/M23907), HLA-DQ (M23907/U92032) and HLA-DR (J00204/AJ297583). The alignment was manually shaded according to H-2E and the structural analysis of PDB ID: 1FNG. This sequence alignment was validated by structural alignment and simultaneous structural superposition of representative PDB entries: 1FNG (I-E$^k$), 1S9V (HLA-DQ2), 1JK8 (HLA-DQ8), 1DLH (HLA-DR1), 1BX2 (HLA-DR2), 1HQR (HLA-DR2a), 1A6A (HLA-DR3), 1D6E (HLA-DR4) and 2Q6W (HLA-DR52a). The spdb viewer 3.7SP5 software[2] was used for all molecular visualization and manipulation operations.

Bacterial Strains, Helper Phages and Plasmids

The E. coli strain XL1-Blue™ and VCSM13 helper phage were purchased from Stratagene (LaJolla, Calif., USA). HyperPhage™ helper phages were purchased from Progen Biotechnik GmbH (Heidelberg, Germany). The pIII display phagemid pSEX81[3] harbouring a single chain Fv (scFv) with specificity against phOx-BSA was kindly provided by Affitech AS (Oslo, Norway) and is also available through PROGEN Biotechnik GmbH (Heidelberg, Germany). The pSEX81-based pFAB-Display and pFABDFN phagemids harbouring the phOx-BSA specificity has been described previously[4].

Cell Lines

The T-cell hybridoma LD1[5] is specific for an influenza hemagglutinin derived peptide (amino acids 110-120; N-SFERFEIFPKE-C, SEQ ID NO:13) when presented on the murine MHC class II molecule I-E$^d$. The human CD4$^+$ T cell clone T18 is specific for mouse Ig C kappa (amino acids 40-48; N-WKIDGSERQ-C, SEQ ID NO:14) and restricted by HLA-DR4 (DRA1,B1*0401) (PMID: 12456590). The human T cell clones, TCC 820.26 and TCC 820.88, recognize the DQ2-αI-epitope (amino acids 57-68; N-QLQPF-PQPELPY-C, SEQ ID NO:15) and DQ2-αII-epitope (amino acids 62-72; N-PQPELPYPQPE-C, SEQ ID NO:16), respectively. The cells were kindly provided by Dr. S.-W. Qiao (Institute of Immunology, University of Oslo, Oslo, Norway). All cells were maintained in RPMI 1640 supplemented with 10% FCS, 0.1 mM non-essential amino acids, 1 mM Sodium Pyruvate, 50 μM Monothioglycerol, and 12 μg/ml gentamicin sulphate.

Abs and Additional Reagents

All media and buffers were prepared essentially as described in Sambrook et al[6]. The mouse anti-pIII, rabbit anti-fd, rabbit anti-fd biotin conjugate, sheep anti-M13-HRP, and sheep anti-mouse-HRP antibodies were purchased from MoBiTec (Goettingen, Germany), Sigma-Aldrich (Oslo, Norway) and Amersham Biosciences (Uppsala, Sweden), respectively. The anti-I-E/I-A antibody 2G9 and streptavidin-PE and streptavidin-APC conjugates were purchased from BD Pharmingen (San Jose, Calif., USA). The rat anti-mouse CD32 antibody 2.4G2 (ATCC® number HB-197™) was produced in-house. The hapten 2-phenyloxazol-5-one (phOx) conjugated to bovine serum albumin (BSA) was prepared essentially as described. Restriction enzymes (RE) were purchased from New England Biolabs (Ipswich, Mass., USA) with the exception of DpnI, which was obtained from Stratagene (LaJolla, Calif., USA). DNA oligos were purchased from MWG Biotech AG (Ebersberg, Germany), DNA Technology (Aarhus, Denmark), or Sigma-Aldrich. BSA and Tween 20 was purchased form Sigma-Aldrich (Oslo, Norway). Pfu Turbo DNA polymerase was purchased from Stratagene (LaJolla, Calif., USA). Trypsin/EDTA was purchased from BioWhittaker (Lonza Group Ltd., Visp, Switzerland).

Construction of an I-E$^d$-pIII Display Phagemid

Figure 2:
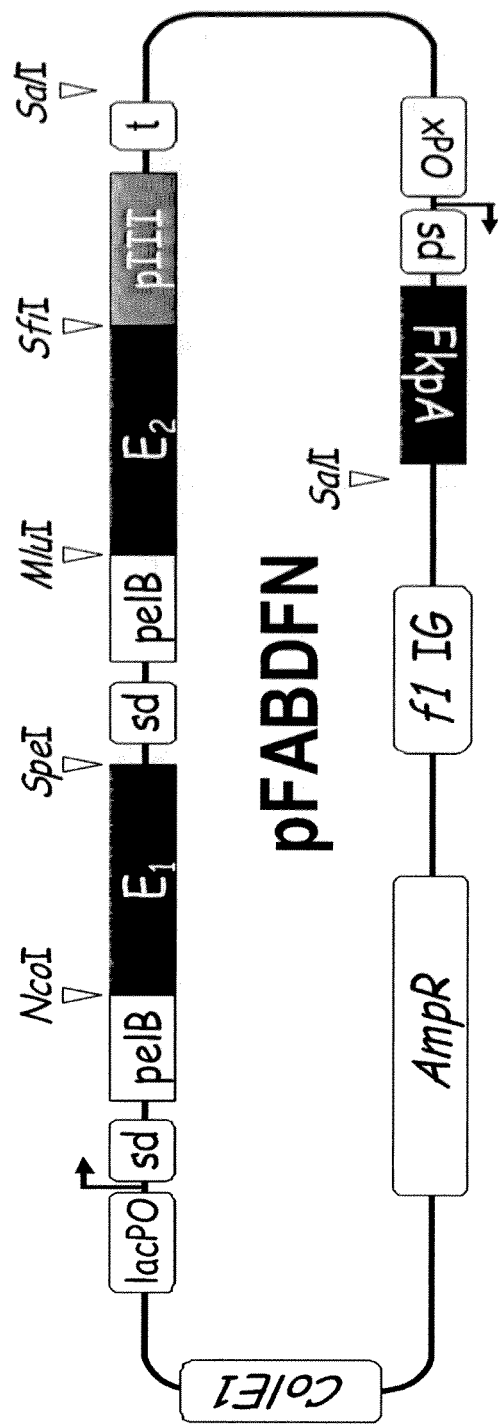
FIG. 2 shows the vector backbone of the pFABDFN phagemid is based on the pIII display phagemid pSEX81 (GenBank accession no.: Y14584). The phagemid can accommodate segments of in frame exogenous sequences (termed $E_1$ and $E_2$) through cassette exchange of the NcoI/SpeI and MluI/SfiI portions respectively. The I-E$^d$ α-chain (aa 26-204) and β-chains (aa 27-216) were inserted in $E_1$ and $E_2$, respectively. Abbreviations: lacPO, lac promoter; sd, Shine-Dalgarno sequence; pelB, signal sequence of bacterial pectate lyase; t, T7 transcriptional terminator; xPO, native promoter of fkpA; FkpA, open reading frame of fkpA; f1 IG, intergenic region of phage f1; AmpR, β-lactamase encoding region; ColE1, origin of replication.

The H-2E genes from A20 BALB/c B lymphoma cells were retrieved by RT-PCR and cloned separately into the eukaryotic pLNOH2 vector, creating I-E$^d$-Ig fusions essentially as described by Casares et al[8]. Genes encoding I-E$^d$α and I-E$^d$β were amplified from these vectors using the following primer pairs: pFAB I-Eda fw (5'-TATACCATGGC-CATCAAAGAGGAACACACCATCATCCAGG-3', SEQ ID NO:17) and pFAB I-Eda rv (5'-TATAACTAGTCAT-TACTCCCAGTG CTTCCGCAGAG-3', SEQ ID NO:18) for I-E$^d$α, and pFAB I-Edb fw (5'-TATAACGCGTCAGAGA-CACCAGACCACGGTTTTTG-3', SEQ ID NO:19) and pFAB I-Edb rv (5'-TATAGGCCGCAGCGGCCCCTTTC-CACTCGACCGTGA CAGGGT-3', SEQ ID NO:20) for I-E$^d$β. I-E$^d$ genes were cloned into the pFABDFN phagemid such that the I-E$^d$α gene was fused to the M13 pIII surface protein whereas the I-E$^d$α chain would be produced as a soluble entity (FIG. 2). DNA encoding an influenza hemagglutinin derived peptide (aa 110-120) and a 15 aa linker (G$_4$S)$_3$ was inserted N-terminally to the I-E$^d$β chain using gene splicing by overlap extension as described[9] and the following primers: pMHCHA SOEing fw (5'-AAAGGAAG- GAGGTGGTGGCTCCGGTGGAGGGG-GAAGTGGAGGTG GAGGGTCTGTCAGAGACACCA-GACCACGGTT-3', SEQ ID NO:21) and pMHCHA SOEing rv (5'-GGAGCCACCACCTCCTTCCTTTGGGAA-GATCTCG AACCTTTCGAATGATACGCGTGC-CATCGCCG-3', SEQ ID NO:22). For cloning purposes, a PstI restriction site in the I-E$^d$β gene was removed by QuikChange™ site directed mutagenesis according to the manufacturers protocol (Stratagene, LaJolla, Calif., USA) using the primers QCIEdbPstI fw (5'-TGGACACGTACTG-TAGACACAACTATGAGAT-3', SEQ ID NO:23) and QCIEdbPstI rv (5'-ATCTCATAGTTGTGTCTACAG-TACGTGTCCA-3', SEQ ID NO:24). Point mutations to introduce disulfide bonds were introduced by QuikChange™ site directed mutagenesis according to the manufacturers protocol (Stratagene, LaJolla, Calif., USA). Primers used were Mut R94C I-Ed alfa fw (5'-GACTGTACTCTCCTGTAGC-CCTGTGAACC-3', SEQ ID NO:25) and Mut R94C I-Ed alfa rv (5'-GGTTCACAGGGCTACAGGAGAGTACAGTC-3', SEQ ID NO:26) for R94C mutation in I-E$^d$α, Mut N151C I-Ed beta fw (5'-CCTGGTCCGATGTGGAGACTGGAC-CTTC-3', SEQ ID NO:27) and Mut N151C I-Ed beta rv (5'-GAAGGTCCAGTCTCCACATCGGACCAGG-3', SEQ ID NO:28) for N150C mutation in I-E$^d$α, QCIEdaS95C fw (5'-ACTCTCCAGATGCCCTGTGAAC-3', SEQ ID NO:29) and QCIEdaS95C rv (5'-GTTCACAGGGCATCTG-GAGAGT-3', SEQ ID NO:30) for S95C mutation in I-E$^d$α, QCIEdbS120C fw (5'-GTCTGCTCTGTGTGTGACTTC-TAC-3', SEQ ID NO:31) and QCIEdbS120C rv (5'-GTA-GAAGTCACACACAGAGCAGAC-3', SEQ ID NO:32) for S120C mutation in I-E$^d$β, QCIEdaP96C fw (5'-CA-GAAGCTGTGTGAACCTGGGA-3', SEQ ID NO:33) and QCIEdaP96C rv (5'-TCCCAGGTTCACACAGCTTCTG-3', SEQ ID NO:34) for P96C mutation in I-E$^d$α, and QCIEdbS118C fw (5'-CCTGGTCTGCTGTGTGAGTGAC-3', SEQ ID NO:35) and QCIEdbS118C rv (5'-GTCACTCA-CACAGCAGACCAGG-3', SEQ ID NO:36) for S118C mutation in I-E$^d$β.

Preparation of MHC II-Displaying Bacteriophage

Phagemid rescue from *E. coli* XL1-Blue™ using VCSM13 or HyperPhage™ helper phages and virion assembly was monitored by spot titration as described[10].

Phage Capture ELISAs

The capturing Abs and phOx-BSA were absorbed to Max-iSorp™ microtiter plate wells (Nunc, Roskilde, Denmark) in concentrations from 2.5 to 5 µg/ml in PBS, pH 7.4 overnight at 4° C. The wells were blocked with PBS™ (PBS supplemented with 0.05% v/v Tween 20 and 4% w/v skim milk) for 1 h at RT. Normalized amounts of virion preparations (VCSM13-rescued samples: 1×10$^{10}$ cfu$^{ampR}$/well; HyperPhage-rescued samples: 1×10$^8$ cfu$^{ampR}$/well) were then added and allowed to react for 1 to 2 h at RT before captured virions were detected with anti-M13-HRP (1:5,000) for 1 h at RT. The wells were developed with TMB soluble substrate (Merck KGaA, Darmstadt, Germany), stopped with 1M HCl after 30 min and the absorbance read at $A_{450\,nm}$.

SDS-PAGE and Western Blotting

Virions (10$^8$ cfu$^{ampR}$/lane) were separated by non-reducing and reducing 4-12% Bis/Tris XT Criterion precast SDS-PAGE (Bio-Rad, Hercules, Calif., USA), and blotted onto a polyvinylidene fluoride membrane (Millipore, Madison, USA) in Tris/glycine buffer (25 mM Tris, 192 mM glycine, and 20% methanol, pH 8.3) at 25 V for 30 min using a semi-dry blotting apparatus (Bio-Rad, Hercules, Calif., USA). The membrane was blocked in PBS™ before pIII-fusions were detected with mouse anti-pIII MAb (1:4,000) followed by sheep anti-mouse-HRP (1:10,000). The membrane was washed and developed with SuperSignal™ West Femto substrate (Pierce, Rockford, Ill., USA) and exposed to BioMax™ MR film (Kodak, Fernwald, Germany).

Construction of HLA-DP, -DR and DQ Containing Artificial S-S Bridges

Genes encoding the representative HLA-DR (DRA*0101/DRB1*1402) and -DQ (DQA1*0501/DQB1*0301), as defined by IMGT (imgt.cines.fr/), were chemically synthesized (Genscript, Piscataway, N.J.). The DNA sequences were optimized by correcting for *E. coli* codon bias, and point mutations to introduce the rank 2 α2-β2 cysteine pair were incorporated (Table 2). The DNA fragments were cloned into the pFABDFN phagemid as described above.

Alternatively, genes encoding the representative HLA-DP (DPA1*0103/DPB1*0401), -DR (DRA*0101/DRB1*1402) and DQ (DQA1*0501/DQB1*0301), as defined by IMGT (imgt.cines.fr/), are amplified by RT-PCR from freshly isolated human PBMC and cloned into the pFABDFN phagemid as described above. Point mutations to introduce the rank 2 (Table 2) α2-β2 cysteine pair are incorporated by QuikChange™ site directed mutagenesis according to the manufacturers protocol (Stratagene, LaJolla, Calif., USA). Primers used (listed in Table 1) are DPA_S95C_sense and DPA_S95C_antisense for the S95C mutation in the HLA-DPA α2-domain, DPB_S121C_sense and DPB_S121C_antisense for the S121C mutation in the HLA-DPB β2-domain, DRA_S95C_sense and DRA_S95C_antisense for the S95C mutation in the HLA-DRA α2-domain, DRB_S121C_sense and DRB_S121C_antisense for the S121C mutation in the HLA-DRB β2-domain, DQA_S95C_sense and DQA_S95C_antisense for the S95C mutation in the HLA-DQA α2-domain, DQB_S121C_sense and DQB_S121C_antisense for the S121C mutation in the HLA-DQB β2-domain.

TABLE 1

| | | |
|---|---|---|
| DPA_E95C_sense | SEQ ID NO: 37 | 5'-GACCGTGTTTCC CAAGT<u>GC</u>CCTGTGGA GCTGGGCC-3' |
| DPA_E95C_antisense | SEQ ID NO: 38 | 5'-GGCCCAGCTCCA CAGG<u>GC</u>ACTTGGGAA ACACGGTC-3' |
| DRA_S95C_sense | SEQ ID NO: 39 | 5'-CTGTGCTCACGA ACT<u>GC</u>CCTGTGGAAC TG-3' |
| DRA_S95C_antisense | SEQ ID NO: 40 | 5'-CAGTTCCACAGG G<u>CA</u>GTTCGTGAGCAC AG-3' |
| DQA_S95C_sense | SEQ ID NO: 41 | 5'-TGAGGTCACAGT GTTTTCCAAGT<u>GC</u>CC CGTGACACTG-3' |
| DQA_S95C_antisense | SEQ ID NO: 42 | 5'-CAGTGTCACGGG <u>GC</u>ACTTGGAAAACAC TGTGACCTCA-3' |
| DPB_T121C_sense | SEQ ID NO: 43 | 5'-TGCTTGTCTGCC ACGT<u>GT</u>GCGATTTCT ACCCAGGCAG-3' |
| DPB_T121C_antisense | SEQ ID NO: 44 | 5'-CTGCCTGGGTAG AAATC<u>GCA</u>CACGTGG CAGACAAGCA-3' |
| DRB_S121C_sense | SEQ ID NO: 45 | 5'-TCCTGGTCTGTT CTGT<u>GT</u>GCGGTTTCT ATCCAGGCAG-3' |

TABLE 1-continued

| | | |
|---|---|---|
| DRB_S121C_antisense | SEQ ID NO: 46 | 5'-CTGCCTGGATAG AAACCGACACAGAA CAGACCAGGA-3' |
| DQB_T121C_sense | SEQ ID NO: 47 | 5'-CTGCTGGTCTGC TCAGTGTGCGATTTC TATCCAGCCCAG-3' |
| DQB_T121C_antisense | SEQ ID NO: 48 | 5'-CTGGGCTGGATA GAAATCGCACACTGA GCAGACCAGCAG-3' |

Flow Cytometry

Figure 6A:
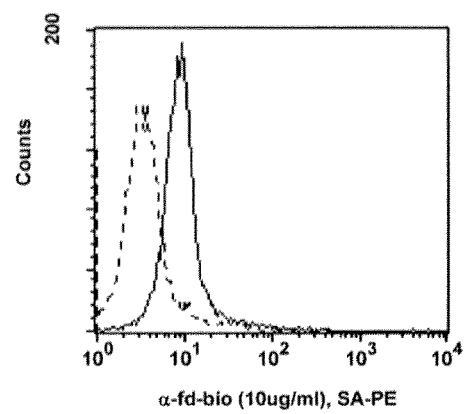
FIG. 6a shows that phages displaying P96C$^{α2}$-S119C$^{α2}$ (rank 1, Table 2) stabilized I-E$^d$ specifically stain LD1 T-cell hybridoma cells. LD1 cells were blocked and stained with I-E$^d$-pIII displaying phagemids for 2 hours on ice followed by incubations with biotinylated rabbit anti-fd biotin conjugate and streptavidin PE. The solid line represents HA$^{aa110-120}$/I-E$^d$ pIII display and the dashed line represents I-E$^d$-pIII display. Notably, specific staining is achieved even at a very low titer ($5 \times 10^9$ phages/ml), whereas the maximum titer achievable is $\sim 10^{13}$ phages/ml.
Figure 6B:
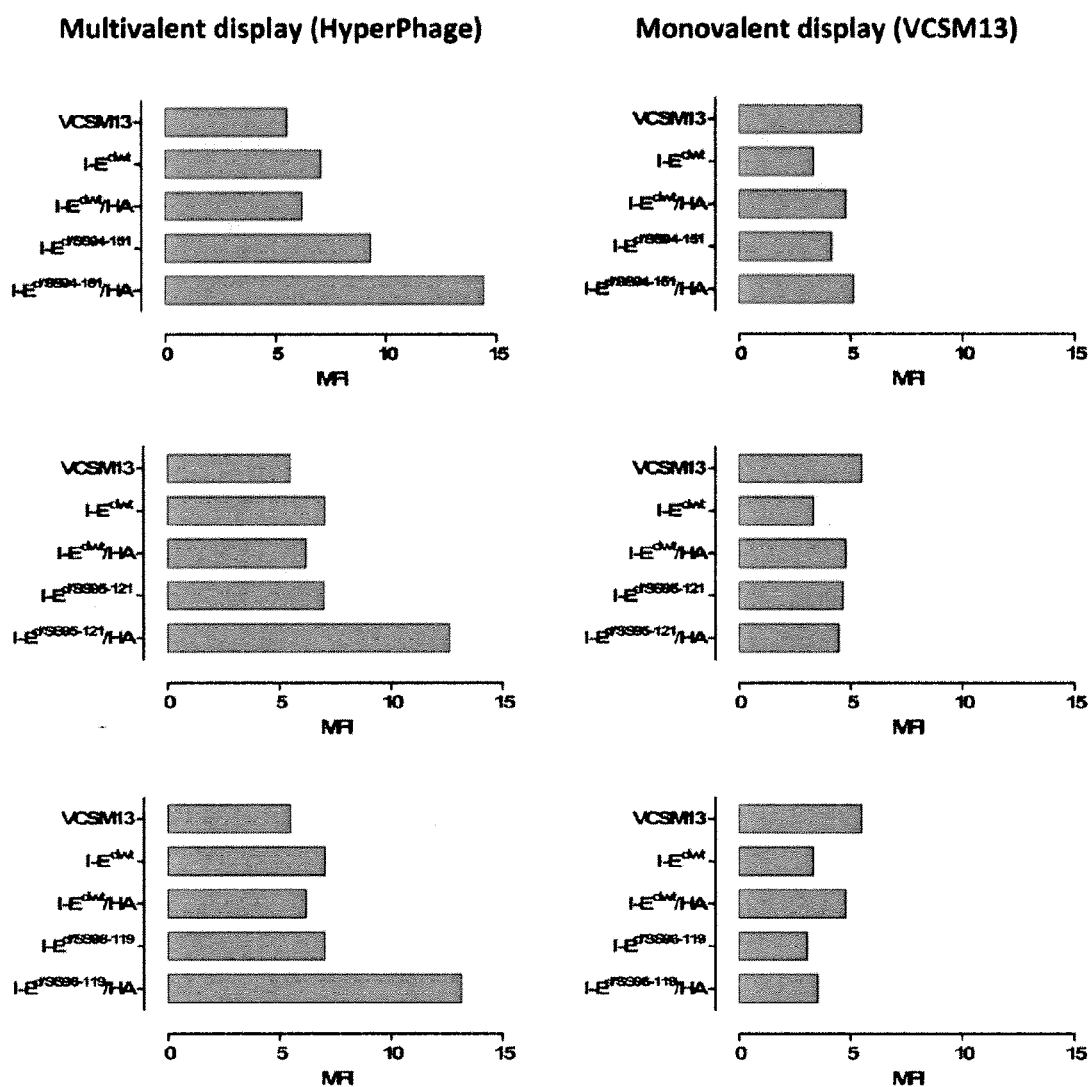
FIG. 6b shows that phages displaying either R94C$^{α2}$-N151C$^{β2}$ (rank 3, Table 2), S95C$^{α2}$-S121C$^{β2}$ (rank 2, Table 2), or P96C$^{β2}$-S119C$^{β2}$ (rank 1, Table 2) stabilized I-E$^d$ specifically stain LD1 T-cell hybridoma cells. LD1 cells were stained with I-E$^d$-pIII displaying phagemids for 30 minutes at RT followed by incubations with biotinylated rabbit anti-fd biotin conjugate and streptavidin APC. Mean Fluorescence Intensity (MFI) for each phage preparation is represented as bar graphs. Notably, specific staining is achieved even at a very low titer ($2 \times 10^9$ phages/ml), whereas the maximum titer achievable is $\sim 10^{13}$ phages/ml.

Single cell suspensions of LD1 cells were either blocked 15 min on ice with 60% heat inactivated rat serum and 200 μg/ml anti-CD32 mAb (HB197) in 1×PBS (FIG. 6a), or not blocked (FIG. 6b). HyperPhage-packaged I-E$^d$-pIII display staining was performed on ice for 2 h in staining buffer (1×PBS with 0.5% BSA) (FIG. 6a), or for 30 min at RT in 1×PBS with 1% BSA (FIG. 6b). The phage in-put used in FIG. 6a was 5×10$^9$ cfu$^{ampR}$ for HA$^{aa110-120}$-I-E$^d$ display, and 1.6×10$^{10}$ cfu$^{ampR}$ for I-E$^d$ display. Phage in-put in FIG. 6b was 2×10$^9$ cfu$^{ampR}$ for all preparations except VCSM13 helper phage (negative control, 1×10$^{11}$ cfU$^{kanR}$/ml). Samples were then incubated 1 hour (FIG. 6a) or 30 min (FIG. 6b) on ice with 10 μg/ml biotinylated rabbit anti-fd followed by 15 min on ice with 2 μg/ml streptavidin PE.

Figure 9:
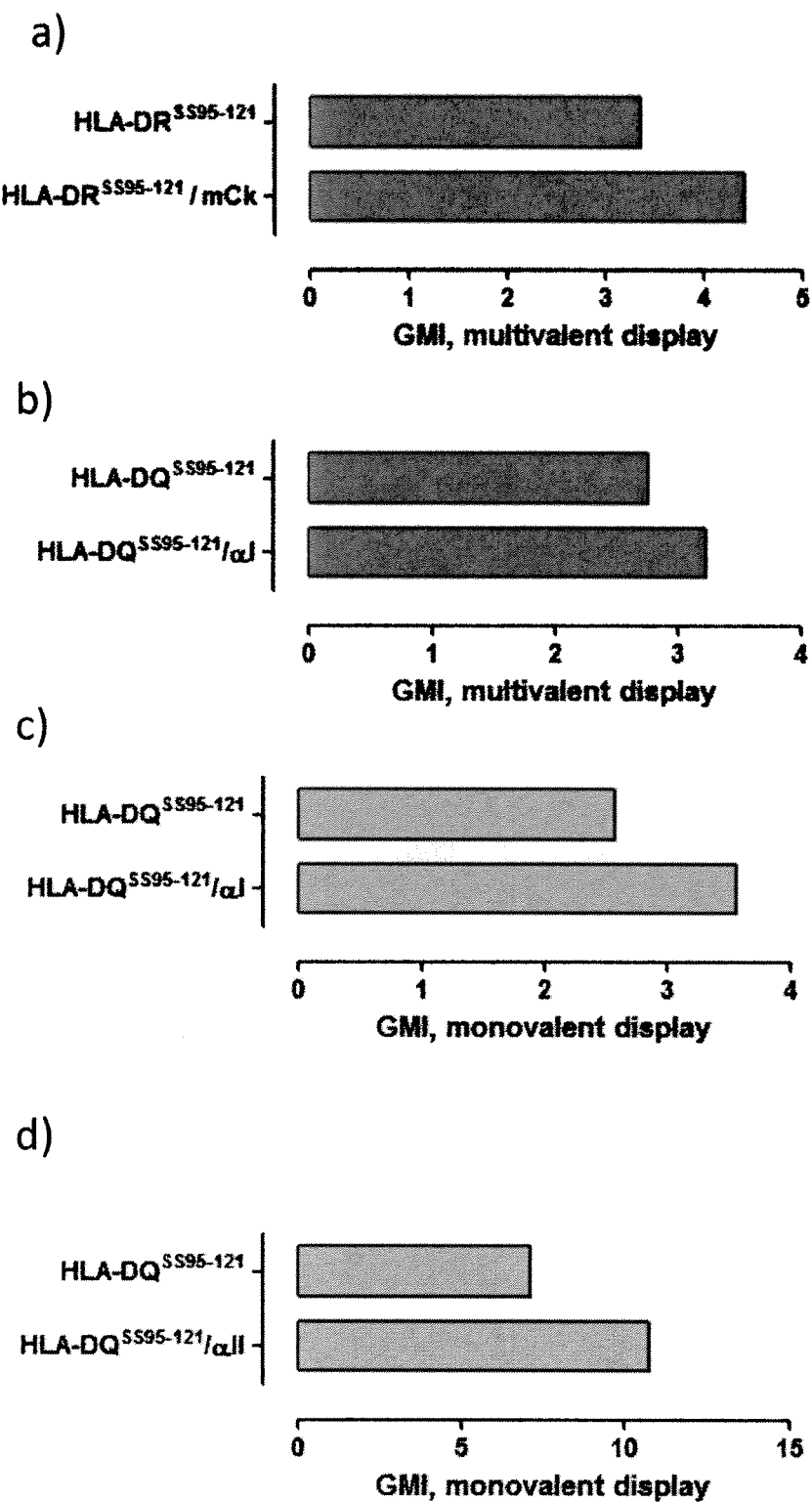
FIG. 9 shows that phages displaying S95C$^{α2}$-S121C$^{β2}$ (rank 2, Table 2) stabilized HLA-DR or HLA-DQ2.5 specifically stain human T-cell clones. T18, TCC 820.26, and TCC 820.88 cells were blocked and stained with HLA class II-pIII displaying phagemids for 1 hour at RT followed by incubations on ice with biotinylated rabbit anti-fd biotin conjugate and streptavidin-PE. Geometric Mean Intensity (GMI) for each phage preparation is represented as bar graphs.

Single cell suspensions in staining buffer (1×PBS with 0.5% BSA) were prepared of the three T cell clones T18, TCC 820.26, or TCC 820.88, respectively. The cells were stained at RT for 1 h with phages either multivalently (HyperPhage-packaged) or monovalently (VCSM13-packaged) displaying HLA class II-pIII fusions (FIG. 9). The phage in-puts used were ~1×10$^9$ cfu$^{ampR}$ (FIG. 9a), ~2×10$^9$ cfu$^{ampR}$ (FIG. 9b) and ~2×10$^{12}$ cfu$^{ampR}$ (FIGS. 9c and d), respectively. Samples were then incubated 1 hour on ice with 10 μg/ml biotinylated rabbit anti-fd followed by 30 min on ice with 2 μg/ml streptavidin-PE. Events were acquired on a FACSCalibur flow cytometer (BD Biosciences) and analyzed using CellQuest PRO software (BD Biosciences).

Results

Molecular Modelling

Table 2 (1FNG numbering) shows the β-carbon side chain distances for selected pairs of residues in the α2/β2 constant domain interface in the I-E$^{dα}$/I-E$^{kβ}$ structure (PDB ID: 1FNG). Indeed, in silico mutagenesis and side chain optimisation of the rank 1 to 3 residues pairs to cysteines yielded disulphide bond distances between 2.03 and 2.07 Å without perturbing the tertiary structure of the protein (FIG. 1). This result strongly indicated that these amino acid substitutions would be allowed and were likely to form disulphide bridges in the mutant polypeptides and hence were chosen for further analysis. Notably, the aa numbering deposited with the PDB ID 1FNG deviates from the IMGT sequence numbering of the β-chain (see FIG. 3B).

TABLE 2

α2-β2 aa pairs arranged by Cβ-Cβ distance

| | aa pairs | | |
|---|---|---|---|
| Rank | 1FNG numbering* | IMGT numbering** | Cβ-Cβ |
| 1 | Pro96$^{α2}$-Ser118$^{β2}$ | Pro96$^{α2}$-Ser119$^{β2}$ | 5.49 |
| 2 | Ser95$^{α2}$-Ser120$^{β2}$ | Ser95$^{α2}$-Ser121$^{β2}$ | 5.51 |
| 3 | Arg94$^{α2}$-Asn150$^{β2}$ | Arg94$^{α2}$-Asn151$^{β2}$ | 5.57 |
| 4 | Phe148$^{α2}$-Gly151$^{β2}$ | Phe148$^{α2}$-Gly152$^{β2}$ | 5.71 |
| 5 | Pro96$^{α2}$-Thr100$^{β2}$ | Pro96$^{α2}$-Thr101$^{β2}$ | 6.11 |
| 6 | Pro96$^{α2}$-Ser120$^{β2}$ | Pro96$^{α2}$-Ser121$^{β2}$ | 6.16 |
| 7 | Ile106$^{α2}$-Asn150$^{β2}$ | Ile106$^{α2}$-Asn151$^{β2}$ | 6.16 |
| 8 | Ser95$^{α2}$-Asp121$^{β2}$ | Ser95$^{α2}$-Asp122$^{β2}$ | 6.30 |

*aa numbering according to PDB ID: 1FNG.
**aa numbering according to the mature IMGT reference sequences H-2EA*02 and H-2EB1*01.

Design of the MHC-pIII Fusions

The I-E$^d$ gene segments were inserted into the pFABDFN phagemid such that the α- and β-chains were translated as two separate polypeptides and of which the β-chain was directly fused in-frame to the N-terminus of the viral capsid protein pIII (FIG. 2). Both chains contained an N-terminal signal sequence (pelB) for periplasmic targeting. The α-chain portion inserted (FIG. 3A, H-2EA_EL) corresponds to amino acids 26-204 of the IMGT H-2EA*02 reference sequence (GenBank accession code: K00971, SEQ ID NO:1) shown in FIG. 3A. Likewise, the β-chain portion corresponding to amino acids 27-216 of the IMGT H-2EB1*01 reference sequence (GenBank accession code: AF050157, SEQ ID NO:2) shown in FIG. 3B was utilized (FIG. 3B, H-2EB_EL). Hence, the positions for the cysteine substitutions rank 1 to 3 in Table 2 correspond to the α-chain positions 94-96 (FIG. 3A), and β-chain positions 119, 121 and 151 (FIG. 3B) of the mature peptides (i.e. the peptides without the signal peptides), respectively, based on the I-E IMGT reference sequences. Notably, this β-chain residue numbering deviates from those deposited with the 1 FNG template file.

Analysis of Phagemid-Derived MHC II-pIII Display

Figure 4:
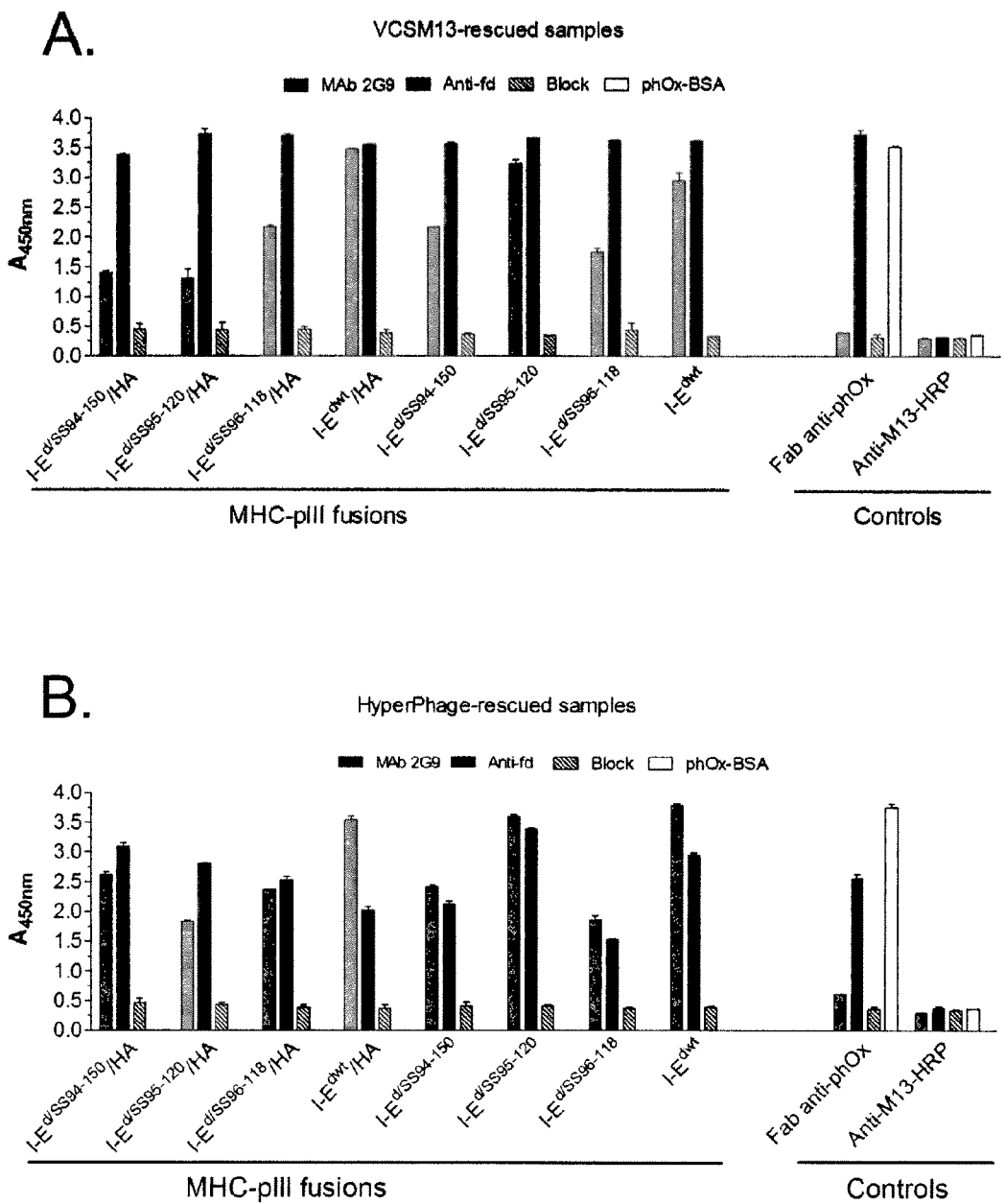
FIG. 4 shows analysis of I-E$^d$-pIII integrity by phage ELISA. The antibodies in question were immobilized and normalized amounts of virions were allowed to react. Captured virions were detected with an anti-M13$^{HRP}$ conjugate and the ELISA was developed with TMB read at $A_{450nm}$. A phOx-BSA specific Fab displayed antibody was included as control.
Figure 5:
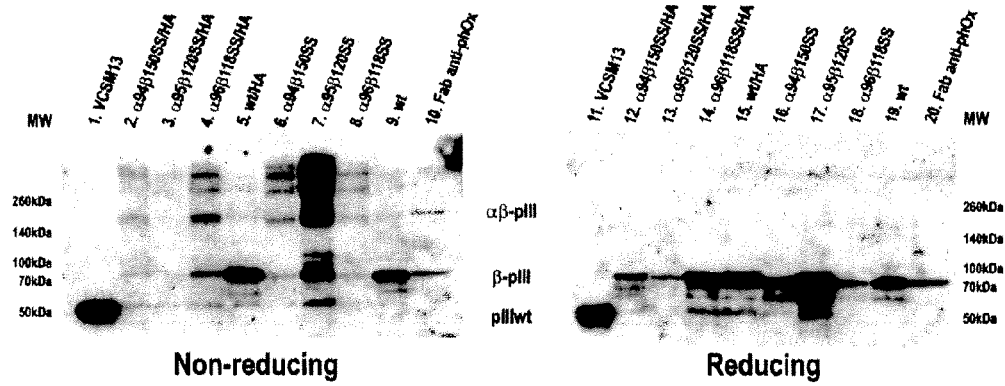
FIG. 5 shows analysis of multivalent I-E$^d$-pIII display levels by SDS PAGE/western blotting developed with anti-pIII. Residue numbering according to PDB ID: 1FNG (see Table 2).

To compare the display propensity and integrity of the pMHC moieties, a phage ELISA was conducted by capturing normalized amounts of virions on an I-E specific monoclonal antibody (MAb), 2G9. The results showed that all samples were recognized by MAb 2G9 both at high and low valence display (FIG. 4), indicating an overall retained structural integrity. MAb 2G9 binds to the I-E β-chain, which was directly fused to pIII. To evaluate whether or not any covalent covalent α-chain heterodimerization was present on the phages, normalized amount of virions were analyzed by non-reducing and reducing SDS PAGE followed by anti-pIII western blot detection (FIG. 5). The results showed that a significant proportion of covalent heterodimers were present in all samples, with two exceptions, the wt (FIG. 5, lane 5) and the α95/β3120 mutant carrying the HA peptide (FIG. 5, lane 3). However, the latter sample did unexpectedly show a very low sample loading hindering a proper resolution. Upon reduction of the samples all the covalent complex formation was abolished (FIG. 5, lanes 11-20). Moreover, as for the antibody Fab control (FIG. 5 lanes 10 and 20), only one covalent heterodimer species was expected for the modified pMHC moieties, Clearly, this was not the case, as multiple such species were observed in all relevant samples. This phenomenon is most likely explained by aberrant disulphide bridge formation between native cysteine residues as well as the introduced mutations. Therefore, only a fraction of the actually displayed protein is found as chains harboring the native disulphide bridges in addition to the artificially introduced bridges in the α2-β2 domains.

Figure 10:
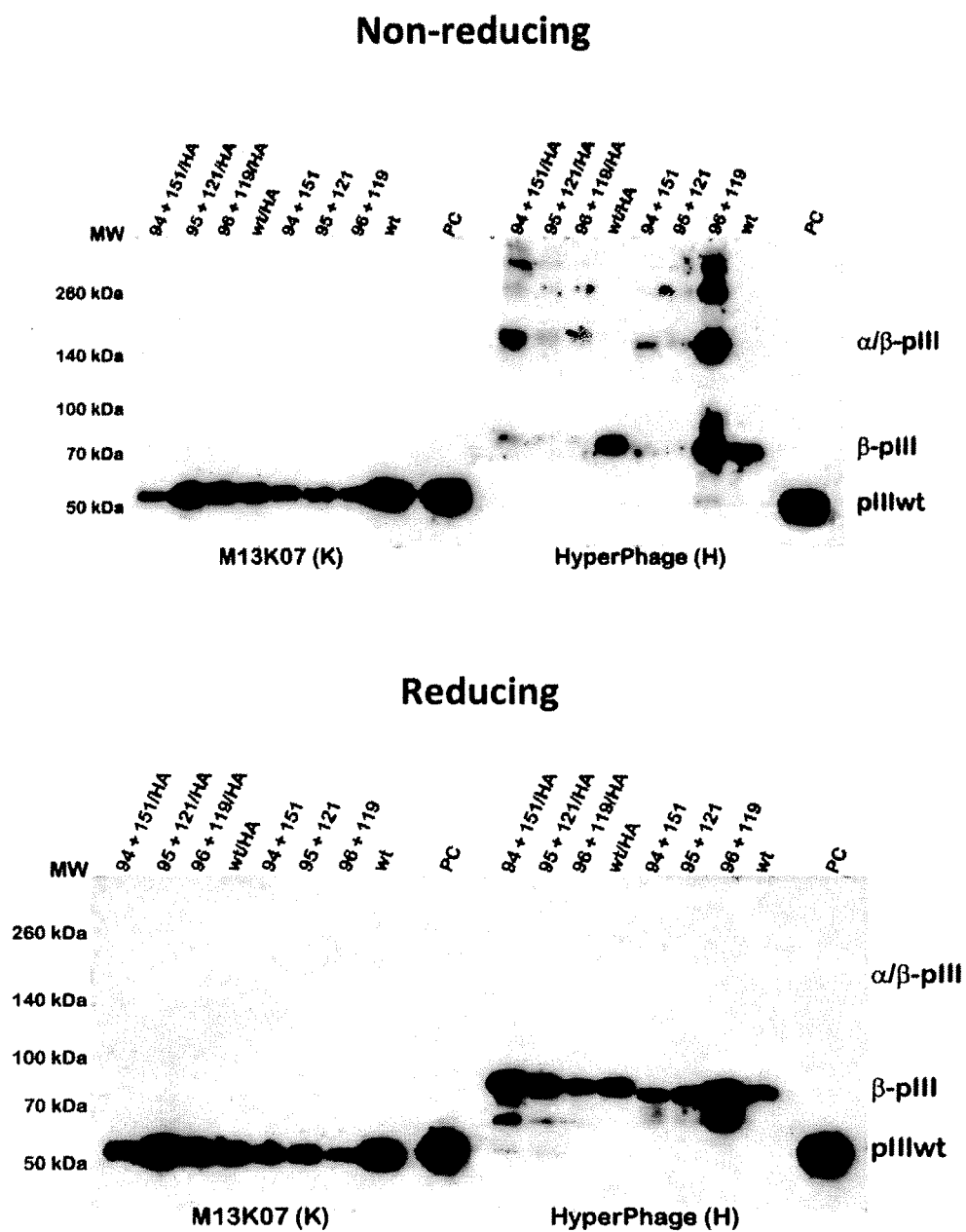
FIG. 10 shows analysis of monovalent (M13K07) and multivalent (HyperPhage) I-E$^d$-pIII display levels by non-reducing or reducing SDS PAGE followed by western blotting detected with anti-pIII. Residue numbering according to IMGT (see Table 2).

A similar experiment was carried out in which monovalent and multivalent display of I-E$^d$-pIII constructs was analysed in parallel. These results are shown in FIG. 10. At low level phagemid display (monovalent), approximately 1-10% of the virions carry a fusion protein (Bradbury and Marks, J Immunol Methods. 2004, 290 (1-2):29.). No apparent fusion protein is therefore seen in these samples (M13K07 samples), despite the fusion being readily detected in a much more sensitive ELISA assay (FIG. 4).

pMHC pIII as Cell Surface Staining Reagents

To investigate whether peptide-MHC class II displayed as fusions to pIII on bacteriophage could be used as staining reagents similar to conventional pMHC II tetramers, we stained LD1 cells with HA$^{aa110-120}$/I-E$^d$-pIII or I-E$^d$-pIII without fused peptide. As seen in FIG. 6a, no staining was observed with I-E$^d$-pIII fusions on bacteriophages produced without the relevant peptide, whereas HA$^{aa110-120}$/I-E$^d$-pIII stained cells with approximately 0.8 log brighter intensity. As seen in FIG. 6b, the peptide specific staining is observed for all three investigated disulfide bridges. The positive staining was only observed with the disulfide stabilized I-E$^d$-pIII versions and only with the versions harbouring the antigenic peptide (HA$^{aa110-120}$). No apparent difference between the three engineered disulfide bridges was seen; hence they appear to work with similar efficiency.

To further address the functionality of pMHC-pIII, mCκ$^{aa40-48}$/HLA-DR4-pIII αI$^{aa57-68}$/HLA-DQ2.5, or αII$^{aa62-72}$/HLA-DQ2.5 displaying virions were prepared by phagemid rescue using either VCSM13 or HyperPhage™. All pMHC-pIII fusions were also made without antigenic peptide fusions as controls. These virions were then tested in flow cytometry experiments as described. As seen in FIG. 9a, the peptide specific staining was observed for mCκ$^{aa40-48}$/HLA-DR4-pIII stained cells. In FIGS. 9b and c, both multivalent and monovalent display of αI$^{aa57-68}$/HLA-DQ2.5 exhibit peptide specific staining. Notably, the phage in-put was $10^{12}$ cfu$^{ampR}$ of VCSM13-packaged αI$^{aa57-68}$/HLA-DQ2.5 display. Peptide specific staining for αII$^{aa62-72}$-HLA-DQ2.5 is demonstrated in FIG. 9d.

Discussion

The main obstacle for effective use of soluble, recombinant MHC class II molecules is caused by inherent stability problems of such engineered molecules. Though a variety of engineered approaches have been adopted to overcome this limitation, no generic approach exists as of today[11]. Moreover, all currently used avenues represents costly and labour intensive procedures effectively undermining any high-throughput approaches. The present inventors have found an attractive solution to this problem by merging recombinant MHC class II production with phage display technology[12]. Not only is this a very fast and inexpensive technology platform, but it also possesses the inherent property of allowing highly diverse combinatorial screening approaches to be used. Given the immense antigenic proteome space presented by the MHC molecules would strongly benefit from this combinatorial feature in e.g. epitope discovery. However, as of yet such discovery has been limited to cumbersome and low-throughput technology based on baculoviruses[13].

By using phage display, repertoire sizes orders of magnitude larger would easily be at hand in a well documented and easy format[12]. Although such display has been explored for the MHC class I molecule[14-16], none of the MHC class I phage displayed approaches have as of yet proven functional as a substitute to soluble tetramers, as cell specific staining remains to be obtained[16]. In contrast to the MHC class I molecule, which can be effectively produced as a single polypeptide[18], the production of MHC class II is complicated by the fact that it is a heterodimer of equally contributing, separate chains[11]. Being built on the Ig fold topology, the functional fold of both MHC class I and II also requires the formation of intra-domain disulphide bridges[19].

A key aspect of the native interaction between the MHC class II and its cognate ligand, the T cell receptor, is the inherent weak affinity[20]. To overcome this limitation in sensitivity when recombinant MHC class II molecules are used as detection reagent, polymerization of the molecules into tetramers or pentamers have been necessary[11]. The production of such polymers involves a multi-step protocol with substantial handling. The use of phage display here very easily allows such polymerization by the use of already available technology that allow multimeric display on the phage[21].

The inventors here present a strategy to obtain functionally displayed MHC class II molecules by pIII phagemid display. To achieve this, the two α- and β-chains are expressed as two separate polypeptide chains in E. coli, of which one is fused to the pIII capsid, and targeted to the periplasm. In the oxidizing periplasm, the two chains form stable heterodimers by harnessing a novel artificial disulphide bridge forcing the association of the α2 and β2 domains. Multiple positions in the conserved α2-β2 interface of the murine MHC class II molecule I-E$^d$ can be targeted for aa substitutions allowing the engineering of an artificial inter-chain disulphide bridge (FIGS. 1 and 3). By displaying such artificial MHC molecules on pIII using standard phagemid-based phage display, covalent heterodimers are indeed displayed on the virions (FIGS. 5 and 10). The overall molecular integrity appears to be retained as all molecules, both wt and mutants, are reactive to a monoclonal antibody (MAB 2G9) specific for the murine MHC class II I-E molecule (FIG. 4). The I-E$^d$ molecules were engineered to display the well characterized HA$^{aa110-120}$ antigenic peptide[22] as a covalent tether to the β-chain essentially as described[23]. Using phages displaying these disulphide bridge stabilized recombinant molecules in flow cytometry, specific staining of the LD1 T cell hybridoma[5], which harbours a T cell receptor specific for the I-E$^d$/HA$^{aa110-120}$ complex, was obtained (FIGS. 6a and b). Importantly, specific staining was only seen with disulfide stabilized I-E$^d$-pIII fusions harbouring the antigenic peptide, truly showing the functionality of the approach. Moreover, multivalent display of the MHC moiety appeared essential for staining, as no such staining was seen with monovalent display (data not shown), underscoring the need to raise the functional affinity above that of the native interaction. This represents the first example to date where a phage displayed MHC molecule has been used for direct visualization of specific T cells complementary to classical MHC tetramer technology.

The key to the success is the introduction of the artificial disulphide bridge stabilizing the α2-β2 interface of the MHC class II molecule. This appears to be a generic approach, as the identified positions are highly conserved among MHC class II molecules, including HLA (FIGS. 7 and 8). This generic nature is strongly supported by the fact that also the three other MHC class II complexes tested, namely mCκ$^{aa40-48}$/HLA-DR4, αI$^{aa57-68}$/HLA-DQ2.5 and αII$^{aa\ 62-72}$/HLA-DQ2.5, all as pIII fusions, showed specific cell staining in flow cytometry in an antigenic peptide-specific manner (FIG. 9). As expected, staining performance and dependency of a multivalent interaction varied among the specific pMHC II complexes and the T cell clones they reacted with. Thus, the dependency of multivalency was not an all or nothing event, shown by specific cell staining by both the αII$^{aa57-68}$/HLA-DQ2.5 and αII$^{aa\ 62-72}$/HLA-DQ2.5 in monovalent versions.

The ability to specifically stain positive in flow cytometry will depend on parameters such as the intrinsic affinity of the particular T cell receptor towards the pMHC, the receptor density on the T cell and the ability of receptor clustering in the membrane. Noteworthy, the multivalent (FIG. 9b) and monovalent (FIG. 9c) staining with the $\alpha I^{aa57-68}$/HLA-DQ2.5 was nearly identical despite a 1000-fold lower phage input with the multivalent version.

REFERENCES

1. Kersh, G. J. et al. Structural and Functional Consequences of Altering a Peptide MHC Anchor Residue. *Journal of Immunology* 166, 3345-3354 (2001).
2. Guex, N. & Peitsch, M. C. SWISS-MODEL and the Swiss-PdbViewer: an environment for comparative protein modeling. *Electrophoresis* 18, 2714-2723 (1997).
3. Welschof, M. et al. The antigen-binding domain of a human IgG-anti-F(ab') 2 autoantibody. *PNAS* 94, 1902-1907 (1997).
4. Løset, G. Å., Lunde, E., Bogen, B., Brekke, O. H. & Sandlie, I. Functional phage display of two murine α/β T-cell receptors is strongly dependent on fusion format, mode and periplasmic folding assistance. *Protein Eng Des Sel.* 20, 461-472 (2007).
5. Taylor, A. H., Haberman, A. M., Gerhard, W. & Caton, A. J. Structure-function relationships among highly diverse T cells that recognize a determinant from influenza virus hemagglutinin. *J Exp Med* 172, 1643-1651 (1990).
6. Sambrook, J. & Russell, D. W. Molecular Cloning: A Laboratory Manual, Edn. 3. (Cold Spring Harbor Laboratory Press, Cold Spring Harbor, N. Y.; 2001).
7. Makela, O., Kaartinen, M., Pelkonen, J. L. & Karjalainen, K. Inheritance of antibody specificity V. Anti-2-phenyloxazolone in the mouse. *J Exp Med* 148, 1644-1660 (1978).
8. Casares, S., Bona, C. A. & Brumeanu, T. D. Engineering and characterization of a murine MHC class II-immunoglobulin chimera expressing an immunodominant CD4 T viral epitope. *Protein Eng* 10, 1295-1301 (1997).
9. Horton, R. M., Cai, Z. L., Ho, S. N. & Pease, L. R. Gene splicing by overlap extension: tailor-made genes using the polymerase chain reaction. *Biotechniques* 8, 528-535 (1990).
10. Løset, G. Å., Kristinsson, S. G. & Sandlie, I. Reliable titration of filamentous bacteriophages independent of pIII fusion moiety and genome size by using trypsin to restore wild-type pIII phenotype. *BioTechniques* 44, 551-554 (2008).
11. Vollers, S. S. & Stern, L. J. Class II major histocompatibility complex tetramer staining: progress, problems, and prospects. *Immunology* 123, 305-313 (2008).
12. Bratkovic, T. Progress in phage display: evolution of the technique and its applications. *Cell Mol Life Sci* (2009).
13. Crawford, F. et al. Use of baculovirus MHC/peptide display libraries to characterize T-cell receptor ligands. *Immunol Rev* 210, 156-170 (2006).
14. Le Doussal, J., Piqueras, B., Dogan, I., Debre, P. & Gorochov, G. Phage display of peptide/major histocompatibility complex. *J Immunol Methods* 241, 147-158. (2000).
15. Kurokawa, M. S. et al. Expression of MHC class I molecules together with antigenic peptides on filamentous phages. *Immunol Lett* 80, 163-168 (2002).
16. Vest Hansen, N., Ostergaard Pedersen, L., Stryhn, A. & Buus, S. Phage display of peptide/major histocompatibility class I complexes. *Eur J Immunol* 31, 32-38 (2001).
17. Constantin, C. M., Bonney, E. E., Altman, J. D. & Strickland, O. L. Major histocompatibility complex (MHC) tetramer technology: an evaluation. *Biol Res Nurs* 4, 115-127 (2002).
18. Leisner, C. et al. One-Pot, Mix-and-Read Peptide-MHC Tetramers. *PLoS ONE* 3, e1678 (2008).
19. Halaby, D. M., Poupon, A. & Mornon, J. The immunoglobulin fold family: sequence analysis and 3D structure comparisons. *Protein Eng* 12, 563-571 (1999).
20. Rudolph, M. G., Stanfield, R. L. & Wilson, I. A. How TCRs bind MHCs, peptides, and co-receptors. *Annu Rev Immunol* 24, 419-466 (2006).
21. Soltes, G. et al. On the influence of vector design on antibody phage display. *Journal of Biotechnology* 127, 626-637 (2007).
22. Schild, H. et al. Natural ligand motifs of H-2E molecules are allele specific and illustrate homology to HLA-DR molecules. *Int Immunol* 7, 1957-1965 (1995).
23. Kozono, H., White, J., Clements, J., Marrack, P. & Kappler, J. Production of soluble MHC class II proteins with covalently bound single peptides. *Nature* 369, 151-154 (1994).

The invention claimed is:

1. A recombinant MHC class II molecule, which comprises:
   (i) all or part of the extracellular portion of an MHC class II α chain;
   (ii) all or part of the extracellular portion of an MHC class II β chain;
   wherein (i) and (ii) provide a functional peptide binding domain and wherein (i) and (ii) are linked by a disulphide bond between cysteine residues located in the α2 domain of said α chain and the β2 domain of said β chain, wherein said cysteine residues are not present in native MHC class II α2 and β2 domains, and wherein said recombinant molecule does not comprise a leucine zipper motif.

2. The recombinant MHC class II molecule of claim 1, wherein said disulphide bond is located between cysteine residues positioned at Pro $96^{α2}$-Ser $119^{β2}$ (rank 1), Ser $95^{α2}$-Ser $121^{β2}$ (rank 2) or Arg $94^{α2}$-Asn $151^{β2}$ (rank 3) of a murine I-E isotype or the equivalent locations in an alternative MHC class II isotype.

3. The recombinant MHC class II molecule of claim 2, wherein said disulphide bond is located between cysteine residues positioned at $95^{α2}$-Ser $121^{β2}$ (rank 2) of a murine I-E isotype or the equivalent locations in an alternative MHC class II isotype.

4. The recombinant MHC class II molecule of claim 1, further wherein one or more of the cysteine residues corresponding to positions 38, 42 or 106 of the reference sequence H-2EB*01 (SEQ ID NO:2) or one or more of the cysteine residues at equivalent locations in an alternative MHC class II isotype are removed.

5. The recombinant MHC class II molecule of claim 1, wherein said molecule is a soluble molecule.

6. The recombinant MHC class II molecule of claim 5, wherein (i) or (ii) of said molecule is fused to an Fc portion of an immunoglobulin.

7. The recombinant MHC class II molecule of claim 1, wherein said molecule is multimeric.

8. The recombinant MHC class II molecule of claim 1, wherein (i) and (ii) of said molecule are derived from mouse or human MHC class II molecules.

9. The recombinant MHC class II molecule of claim 1, wherein said molecule is produced by a bacterial host.

10. The recombinant MHC class II molecule of claim 9, wherein said bacterial host is E. coli.

11. The recombinant MHC class II molecule of claim 1, wherein said disulphide bond provides the sole means of stabilization of the MHC class II molecule.

12. The recombinant MHC class II molecule of claim 1, wherein said molecule is capable of staining T cells.

13. The recombinant MHC class II molecule of claim 1, wherein said molecule further comprises a peptide bound to said peptide binding domain.

14. A method of producing a recombinant MHC class II molecule, which comprises:
   (i) all or part of the extracellular portion of an MHC class II α chain;
   (ii) all or part of the extracellular portion of an MHC class II β chain;
   wherein (i) and (ii) provide a functional peptide binding domain and wherein (i) and (ii) are linked by a disulphide bond between cysteine residues located in the α2 domain of said α chain and the β2 domain of said β chain, wherein said cysteine residues are not present in native MHC class II α2 and β2 domains, and wherein said recombinant molecule does not comprise a leucine zipper motif,
   said method comprising expressing said recombinant molecule in a prokaryotic host.

15. A method for identifying an antigenic peptide epitope which can be recognized by a T cell having a T cell receptor specific for said antigenic peptide bound to a MHC class II molecule, wherein said method comprises the steps of:
   (i) contacting the recombinant MHC class II molecule of claim 13 with said T cell receptor; and
   (ii) detecting binding of said recombinant MHC class II molecule to said T cell receptor.

16. A method of detecting an antigen specific T cell in a sample, wherein said T cell has a T cell receptor specific for an antigenic peptide bound to a MHC class II molecule, and wherein said method comprises the steps of:
   (i) contacting a recombinant MHC class II molecule of claim 13 with said sample; and
   (ii) detecting binding of said recombinant MHC class II molecule to said T cell.

* * * * *